US012667352B2

(12) United States Patent (10) Patent No.: US 12,667,352 B2
Rajek et al. (45) Date of Patent: Jun. 30, 2026

(54) SURGICAL RETRACTORS AND METHODS OF USING THE SAME

(71) Applicant: Alphatec Spine, Inc., Carlsbad, CA (US)

(72) Inventors: Andrew W. Rajek, Escondido, CA (US); Stephen Vidmar, Carlsbad, CA (US); James Lee, Vista, CA (US); David Considine, Torrington, CT (US); Graham Witherby, Dana Point, CA (US); Maximilian Garcia, Encinitas, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 98 days.

(21) Appl. No.: 18/759,418

(22) Filed: Jun. 28, 2024

(65) Prior Publication Data

US 2025/0000502 A1 Jan. 2, 2025

Related U.S. Application Data

(63) Continuation-in-part of application No. 17/738,998, filed on May 6, 2022, now Pat. No. 12,369,897.
(Continued)

(51) Int. Cl.
*A61B 17/02* (2006.01)
*A61B 17/00* (2006.01)

(52) U.S. Cl.
CPC .. *A61B 17/025* (2013.01); *A61B 2017/00367* (2013.01); *A61B 2017/0256* (2013.01)

(58) Field of Classification Search
None
See application file for complete search history.

(56) References Cited

U.S. PATENT DOCUMENTS 4,834,112 A 5/1989 Machek et al.
5,667,481 A * 9/1997 Villalta ................. A61B 17/02
600/219
(Continued)

FOREIGN PATENT DOCUMENTS

DE 202009005768 U1 6/2009
DE 202020003344 U1 8/2020
(Continued)

OTHER PUBLICATIONS

International Preliminary Report on Patenability from related pending international application PCT/US2022/028132, dated Oct. 24, 2023.
(Continued)

*Primary Examiner* — Eduardo C Robert
*Assistant Examiner* — Anna V. Little
(74) *Attorney, Agent, or Firm* — Dentons Durham Jones Pinegar; Sarah W. Matthews; Lilly Godfrey

(57) ABSTRACT

This disclosure relates generally to surgical retractors and surgical retractor systems configured to provide access to a surgical site, such as a portion of a patient's spine. Also disclosed are retractor blades or blade assemblies connectable to surgical retractors. A self-adjusting retractor blade includes a sheath extending from a proximal end to a distal end, with the sheath having an engagement portion at the proximal end configured for releasable engagement with a surgical retractor system, a channel extending to the distal end, and a blade tip at least partially contained within the channel, the blade tip configured to slide within the channel. The blade tip may be biased in a first position relative to the sheath. Methods of assembling and using the surgical retractors and surgical systems are also disclosed.

28 Claims, 46 Drawing Sheets

Related U.S. Application Data

(60) Provisional application No. 63/186,008, filed on May 7, 2021.

(56) References Cited

U.S. PATENT DOCUMENTS

| | | | |
|---|---|---|---|
| 5,795,291 A | 8/1998 | Koros et al. | |
| 5,882,298 A | 3/1999 | Sharratt | |
| 5,902,233 A * | 5/1999 | Farley | A61B 17/0206 600/215 |
| 5,928,139 A | 7/1999 | Koros et al. | |
| 6,342,036 B1 | 1/2002 | Cooper et al. | |
| 6,945,933 B2 | 9/2005 | Branch et al. | |
| 7,582,058 B1 | 9/2009 | Miles et al. | |
| 7,785,253 B1 | 8/2010 | Arambula et al. | |
| 8,137,284 B2 | 3/2012 | Miles et al. | |
| 8,876,709 B2 | 11/2014 | Vayser et al. | |
| 8,900,137 B1 | 12/2014 | Lovell et al. | |
| 8,974,381 B1 | 3/2015 | Lovell et al. | |
| 9,028,522 B1 | 5/2015 | Prado | |
| 9,113,853 B1 | 8/2015 | Casey et al. | |
| 9,277,906 B2 | 3/2016 | White | |
| 9,414,828 B2 | 8/2016 | Abidin et al. | |
| 10,426,454 B2 | 10/2019 | Ponmudi et al. | |
| 10,448,941 B2 | 10/2019 | Daavettila et al. | |
| 2004/0059192 A1* | 3/2004 | Cartier | A61B 17/0206 600/210 |
| 2004/0087833 A1 | 5/2004 | Bauer et al. | |
| 2005/0096508 A1* | 5/2005 | Valentini | A61B 17/0206 600/210 |
| 2006/0052671 A1* | 3/2006 | McCarthy | A61B 17/0206 600/232 |
| 2007/0038216 A1* | 2/2007 | Hamada | A61B 17/02 606/53 |
| 2008/0097164 A1* | 4/2008 | Miles | A61B 17/025 600/219 |
| 2008/0114208 A1* | 5/2008 | Hutton | A61B 17/02 600/210 |
| 2010/0081885 A1 | 4/2010 | Wing et al. | |
| 2010/0222644 A1 | 9/2010 | Sebastian et al. | |
| 2011/0034781 A1* | 2/2011 | Loftus | A61B 17/7076 600/215 |
| 2012/0323080 A1 | 12/2012 | Deridder et al. | |
| 2013/0261401 A1 | 10/2013 | Hawkins et al. | |
| 2014/0172002 A1 | 6/2014 | Predick | |
| 2014/0336471 A1 | 11/2014 | Pfabe et al. | |
| 2015/0351738 A1 | 12/2015 | Perrow | |
| 2016/0192922 A1 | 7/2016 | Friedrich et al. | |
| 2016/0317137 A1 | 11/2016 | Predick et al. | |
| 2017/0143325 A1 | 5/2017 | Lynn et al. | |
| 2017/0231613 A1 | 8/2017 | Casey et al. | |
| 2017/0238918 A1 | 8/2017 | Predick et al. | |
| 2017/0311941 A1 | 11/2017 | Daavettila et al. | |
| 2017/0333023 A1 | 11/2017 | Adams | |
| 2019/0015089 A1* | 1/2019 | Rosenbaum | A61B 17/0206 |
| 2019/0021715 A1 | 1/2019 | O'Connell et al. | |
| 2019/0090864 A1* | 3/2019 | Medeiros | A61B 90/60 |
| 2019/0142480 A1 | 5/2019 | Woolley et al. | |
| 2019/0216450 A1* | 7/2019 | Bjork | A61B 17/0206 |
| 2019/0298328 A1 | 10/2019 | Popejoy et al. | |
| 2019/0307439 A1 | 10/2019 | Chhit et al. | |
| 2020/0015799 A1 | 1/2020 | Tsubouchi | |
| 2021/0085306 A1 | 3/2021 | Clauss et al. | |

FOREIGN PATENT DOCUMENTS

| | | |
|---|---|---|
| WO | 2016153942 A1 | 9/2016 |
| WO | 2019055173 A1 | 3/2019 |

OTHER PUBLICATIONS

Search Report of the International Searching Authority from related pending international application PCT/US2022/028132, dated Oct. 24, 2023.

Written Opinion of the International Searching Authority from related pending international application PCT/US2022/028132, dated Oct. 24, 2023.

* cited by examiner

3105

3109

3107

3131

3108

3130

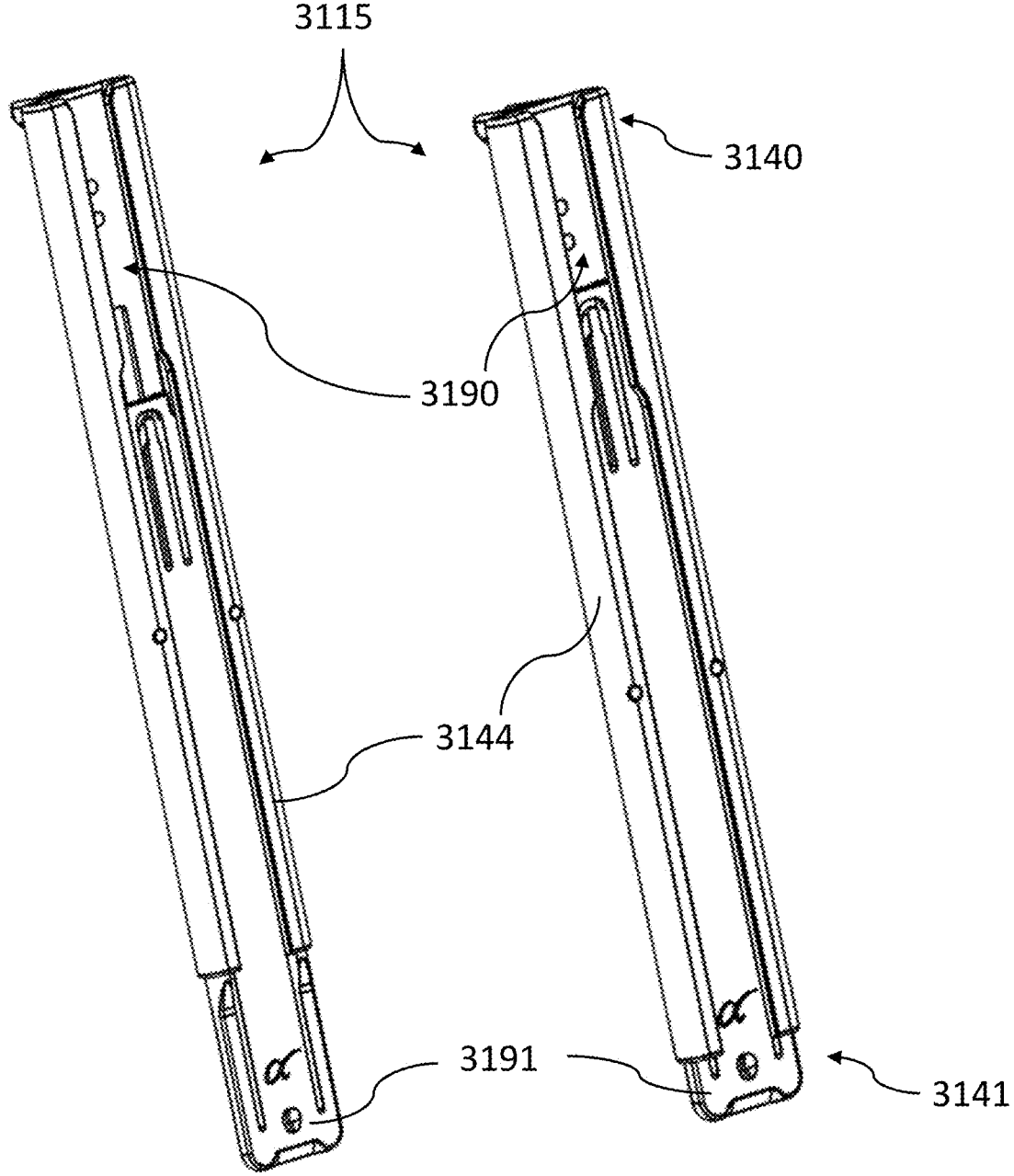
FIG. 34A                    FIG. 34B

Attaching An Anterior Cabin To An Anterior Arm Of A Base Retractor, The Anterior Arm Having An Anterior Blade, <u>5005</u>

↓

Attaching A Posterior Cabin To A Posterior Arm Of The Base Retractor, The Posterior Arm Having A Posterior Blade, The Posterior Blade Being Substantially Parallel To The Anterior Blade, <u>5010</u>

↓

Securing A First Auxiliary Blade To The Anterior Cabin, The First Auxiliary Blade Oriented Orthogonal To The Anterior Blade And Having An Outward Bias Relative To The Anterior Blade, <u>5015</u>

↓

Securing A Second Auxiliary Blade To The Posterior Cabin, The Second Auxiliary Blade Oriented Orthogonal To The Posterior Blade And Having An Outward Bias Relative To The Posterior Blade, <u>5020</u>

↓

Each Of The First Auxiliary Blade And The Second Auxiliary Blade Being Independently Moveable Relative To The Anterior Blade, The Posterior Blade, And Each Other

Positioning A Patient In A Prone Position, A Lateral Decubitus Position, A Supine Position, Or Any Other Suitable Patient Position, <u>6005</u>

Identifying An Incision Point For Accessing A Desired Surgical Site, Creating An Incision, And Advancing An Instrument Guide—such As A Guide Wire Or A K-wire—to The Surgical Site, <u>6010</u>

Advancing One Or More Sequential Dilators Along The Instrument Guide Through The Incision And Down To The Surgical Site, <u>6015</u>

Advancing A Surgical Retractor Along The Instrument Guide Through The Incision And Down To The Surgical Site, <u>6020</u>

Creating A Surgical Corridor Within The Surgical Site, <u>6025</u>

FIG. 46

SURGICAL RETRACTORS AND METHODS OF USING THE SAME

RELATED APPLICATIONS

This application is a continuation-in-part of U.S. patent application Ser. No. 17/738,998 filed on May 6, 2022 and entitled "SURGICAL RETRACTORS AND METHODS OF USING THE SAME," which claims priority to the May 7, 2021 filing date of U.S. Provisional Application No. 63/186,008 and titled "SURGICAL RETRACTORS AND METHODS OF USING THE SAME," the entire contents of which are herein incorporated by reference.

TECHNICAL FIELD

This disclosure relates generally to surgical retractors configured to provide access to a surgical site, such as a portion of a patient's spine. Also disclosed herein are methods of using such surgical retractors in surgical procedures, such as a spinal surgery.

SUMMARY

Disclosed herein are surgical retractors and methods of using such surgical retractors where the surgical retractors include a base portion and two retractor blades. The base portion has (a) two extensions, each extension having a receiving area, and (b) and one or more engagement portions. Each retractor blade includes both a blade portion with proximal and distal ends and an arm portion extending from the proximal end of the blade portion. Each arm portion is received by a respective receiving area.

Each receiving area may include a ratchet mechanism that engages with and locks the arm portion relative to the base portion. In some embodiments, the arm portion includes ratchet teeth to engage the ratchet mechanism. In some embodiments, the receiving areas can include an advancement mechanism that when rotated adjusts the position of the arm portion relative to the base portion.

According to some embodiments, the retractor blades consist of a unitary piece. In some embodiments, the retractor blades are functionally integral. In some embodiments, the blade portion is orthogonal to the arm portion, each blade portion is parallel to the other blade portion, and the arm portions are parallel to the base portion. In some embodiments, the retractor is configured to maintain such orthogonality and parallel orientation even as the two retractor blades are adjusted relative to the base portion.

Some embodiments include an alignment feature to indicate whether the retractor is properly oriented relative to a target site, such as a patient's disc space. In some embodiments, a proper orientation is lateral approach that is orthogonal to the disc space. In some embodiments, the alignment feature is radiographically identifiable and is positioned at a proximal end of one or both of the blade portions.

Some embodiments of surgical retractors are configured for use when the patient is in the prone position. Some embodiments allow for use when the patient is in the supine or lateral decubitus position.

According to some embodiments, one or both blade portions include a central channel in order to secure to the blade portion a light cable, anchoring mechanism, blade extender, or other useful tool. Some embodiments include at least one lateral channel that may be used in conjunction with a bone anchor.

According to some embodiments, the cross section of the retractor blades when together is generally circular. In some embodiments, the cross section is general oval-shaped. Whether circular-shaped or oval-shaped, the blades may be configured to slide over a dilator when being advanced toward the surgical site.

Also disclosed herein are methods of using a surgical retractor. Some methods include making an incision in a patient's skin at a position lateral to the patient's spine, locating a surgical site on the spine, inserting the posterior and anterior retractor blades of a two-bladed surgical retractor—which may be a surgical retractor according to the present disclosure—advancing the surgical retractor toward the surgical site, positioning the distal end of the posterior retractor blade at a posterior position of the surgical site, anchoring the posterior retractor blade at the posterior position, and enlarging the surgical corridor.

In some embodiments, locating the surgical site on the spine includes advancing a K-wire toward the surgical site and embedding a distal end of the K-wire into a tissue at the surgical site, and sequentially advancing at least an inner dilator and at least an outer dilator—both of which may have a cross section that is circular or oval in shape—over the K-wire toward the surgical site. In some embodiments, at least one of the inner and outer dilators comprises at least one electrode and is configured to provide neural monitoring, such as plexus mapping, as the dilator is advanced toward the surgical site.

In various aspects, a retractor for use in a surgical procedure includes a base having (i) an anterior arm connectable to an anterior end of the base and having an anterior blade, and (ii) a posterior arm connectable to a posterior end of the base and having a posterior blade. The retractor may also include an anterior cabin or base portion connectable to the anterior arm, where the anterior cabin is for receiving a first auxiliary blade. The first auxiliary blade may include a sheath extending from a proximal end to a distal end, a blade tip at least partially within the sheath and slidable within the sheath, and a spring in connection with the blade tip, with the spring biasing the blade tip distally relative to the sheath. The retractor may further include a posterior cabin or base portion connectable to the posterior arm, where the posterior cabin is for receiving a second auxiliary blade. The posterior cabin may have an extension, such that the second auxiliary blade is positionable anterior to the posterior blade. The second auxiliary blade may be substantially identical to the first auxiliary blade. Each of the first auxiliary blade and the second auxiliary blade may be adjustable in length and in angle in at least two planes. The distal ends of the first auxiliary blade and the second auxiliary blade may be angled outwardly relative to each other.

In various aspects, a retractor for use in a surgical procedure includes a base retractor having a rack, an anterior arm connectable to the rack and having an anterior blade, and a posterior arm connectable to the rack and having a posterior blade. The retractor may also include a first cabin connectable to the anterior arm, where the first cabin is for receiving a first auxiliary blade defining a first axis. The retractor may further include a second auxiliary blade connectable to the posterior arm, the second auxiliary blade defining a second axis. Each of the first auxiliary blade and the second auxiliary blade may be adjustable in length and angulation, and the first and second axes are not parallel to each other so that each of the first auxiliary blade and the second auxiliary blade has an outward bias relative to the anterior blade and posterior blade, respectively.

In various aspects, a method of creating and/or maintaining an exposure in a surgical procedure includes attaching an anterior cabin to an anterior arm of a base retractor, with the anterior arm having an anterior blade, and attaching a posterior cabin to a posterior arm of the base retractor, with the posterior arm having a posterior blade, the posterior blade being substantially parallel to the anterior blade. The method may also include securing a first auxiliary blade to the anterior cabin, the first auxiliary blade oriented orthogonal to the anterior blade and having an outward bias relative to the anterior blade. Additionally, the method may include securing a second auxiliary blade to the posterior cabin, the second auxiliary blade oriented orthogonal to the posterior blade and having an outward bias relative to the posterior blade. Each of the first auxiliary blade and the second auxiliary blade may be independently moveable relative to the anterior blade, the posterior blade, and each other.

In various aspects, a retractor for use in a surgical procedure includes a base retractor having a rack, an anterior arm connectable to the rack and having an anterior blade, and a posterior arm connectable to the rack and having a posterior blade. The retractor may also include a first cabin connectable to the anterior arm, where the first cabin is for receiving a first auxiliary blade. The first auxiliary blade may include a sheath extending from a proximal end to a distal end and a blade tip in connection with the sheath, the blade tip being biased in a first position.

In various aspects, a self-adjusting retractor blade includes a sheath extending from a proximal end to a distal end, with the sheath having an engagement portion at the proximal end configured for releasable engagement with a surgical retractor system, a channel extending to the distal end, and a blade tip at least partially contained within the channel, the blade tip configured to slide within the channel. The blade tip may be biased in a first position relative to the sheath.

In various aspects, a surgical retractor system includes a base having (i) a first retractor arm mechanically engaged to the base and (ii) a second retractor arm mechanically engaged to the base, with the first and second retractor arms independently adjustable relative to the base. The system may also include a first self-adjusting retractor blade releasably secured to the first or second retractor arms.

Other aspects of the disclosed subject matter, as well as features and advantages of various aspects of the disclosed subject matter, should be apparent to those of ordinary skill in the art through consideration of the ensuing description, the accompanying drawings, and the appended claims.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings wherein like structure is indicated with like reference numerals and in which:

FIGS. 34A and 34B illustrates the auxiliary blade of FIG. 33A in two different states of use;

FIGS. 45 and 46 are flowcharts of example methods of using or assembling any one of the surgical retractors of FIGS. 1 through 40.

DETAILED DESCRIPTION

The present disclosure relates to surgical retractors and specifically retractors configured for use in spinal surgeries. Retractors are designed to not simply allow access to a surgical site, but they are further designed to accommodate the particular issues encountered when accessing those surgical sites. To that end, the surgical retractors disclosed herein as well as the methods for using them are particularly suited to accessing the spine of a patient using a lateral approach. Some embodiments are more particularly suited a lateral approach with the patient in a prone position. Some embodiments are more particularly suited a lateral approach with the patient in a lateral decubitus position. Some embodiments are more particularly suited a lateral approach with the patient in a supine position. Although some embodiments are suited for a lateral approach, other approached are also contemplated because the advantageous features of the disclosed retractors lend themselves to other approaches.

Figure 1:
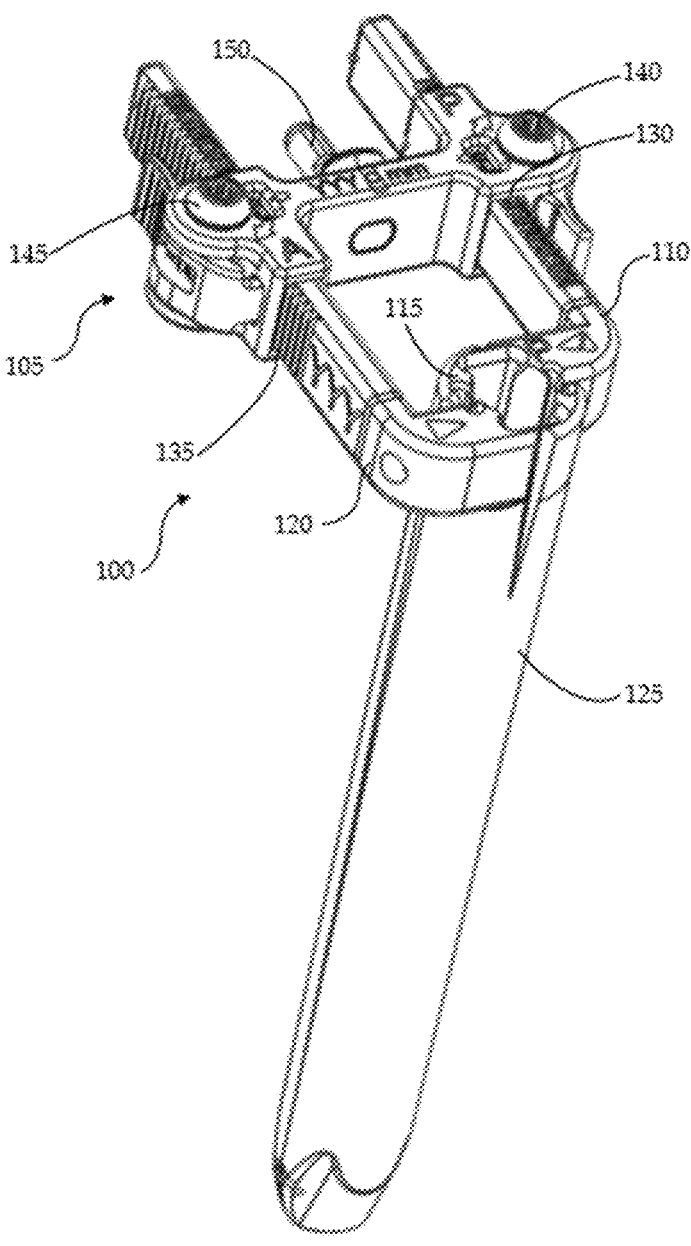
FIG. 1 illustrates a perspective view of a surgical retractor according to the present disclosure.

FIG. 1 illustrates one embodiment of a retractor 100 that includes a base portion 105 having two extensions, a posterior retractor arm 110, a posterior retractor blade 115, an anterior retractor arm 120, and an anterior retractor blade 125. Base portion 105 includes two receiving areas 130, 135—one on each extension. Receiving areas 130, 135 are configured to receive each of the retractor arms. Receiving area 130 is configured to receive posterior retractor arm 110, and receiving area 135 is configured to receive anterior retractor arm 120. Each retractor arm 110, 120 may be removably received by each receiving area 130, 135, or they may include a pin at their respective ends (or some other retaining means) to prevent the arms from being separated from base portion 105. Removability may be desired in order to have the option of quickly opting for a different retractor blade in the posterior and/or anterior position. Base portion 105 is illustrated in greater detail in FIG. 5.

According to some embodiments, retractor 100 is positioned for use in a lateral approach of the lumbar spine during which the patient may be in a prone position, lateral decubitus position, or supine position. In some embodiments, retractor 100 will be positioned with retractor blades 115, 125 forming an orthogonal corridor to the patient's disc space—with posterior blade 115 being posterior to the disc space and anterior blade 125 being anterior to the disc space—in which case base portion 105 will be positioned outside the patient and posterior to the disc space. Other configurations and arrangements are possible, though it has been found that this arrangement provides desired stability with limited interference to the surgical corridor.

Each receiving area includes an adjustment mechanism—140 and 145, respectively—configured to both hold each retractor arm in a fixed position relative to base portion 105 and to allow for incremental adjustment of each retractor arm. Adjustment mechanisms 140, 145 are configured to operate independently of each other. In some embodiments, the two mechanisms are configured to at least partially operate in conjunction by either simultaneously adjusting the two retractor arms and/or by simultaneously releasing each retractor arm so they can freely move relative to base portion 105. Adjustment mechanisms 140, 145 may take the form of any suitable mechanism capable of maintaining the position of retractor arms 110 and 120 fixed relative to base portion 105. In some embodiments, adjustment mechanisms 140, 145 are additionally capable of adjusting the position of retractor arms 110 and 120 fixed relative to base portion 105. In the illustrated embodiment, adjustment mechanisms 140, 145 are ratchet mechanisms that engage corresponding ratchet teeth on each retractor arm.

Base portion 105 further includes an engagement portion 150 extending from base portion 105, which is configured to allow retractor 100 to be releasably secured to a support structure, such as an A-arm that is itself secured to another support structure, such as a bed frame or patient support structure.

Each retractor arm and its associated retractor blade may comprise a unitary piece, may be secured or attached to each to functionally achieve a unitary piece, or be releasably secured to each other. In this embodiment, each retractor arm and its blade is manufactured to be unitary. One advantage of being unitary or functionally unitary is added strength and stability. Such stability is needed to maintain the position of the retractor arm and prevent unwanted movement.

In this illustrated embodiment, various components are configured to be generally orthogonal or generally parallel to each other. For example, base portion 105 can be described as having two extensions along a first plane with each retractor arm located also in the first plane and configured to be maintained in the first plane even as they are adjusted relative to base portion with each are retractor being parallel to the other retractor arm. Similarly, engagement portion 150 extends from base portion 105 in the first plane. Posterior blade 115 and anterior blade 125 are each orthogonal to the first plane and are parallel to each other. The respective orientations are maintained even while adjusting or enlarging the surgical corridor, which requires that one or both of the retractor blades be adjusted relative to base portion 105.

In the illustrated embodiment, engagement portion 150 is shown as extending orthogonally from base portion 105; however, in some embodiments, engagement portion 150 extends at an angle. For example, if engagement portion 150 defines an axis, and if base portion defines a plane, the angle between the axis and the plane is 0° in the illustrated embodiment but may be any suitable angle from about –45° to about 90°, such as about –30°, about –15°, about 0°, about 15°, about 30°, or about 45°.

Figure 2:
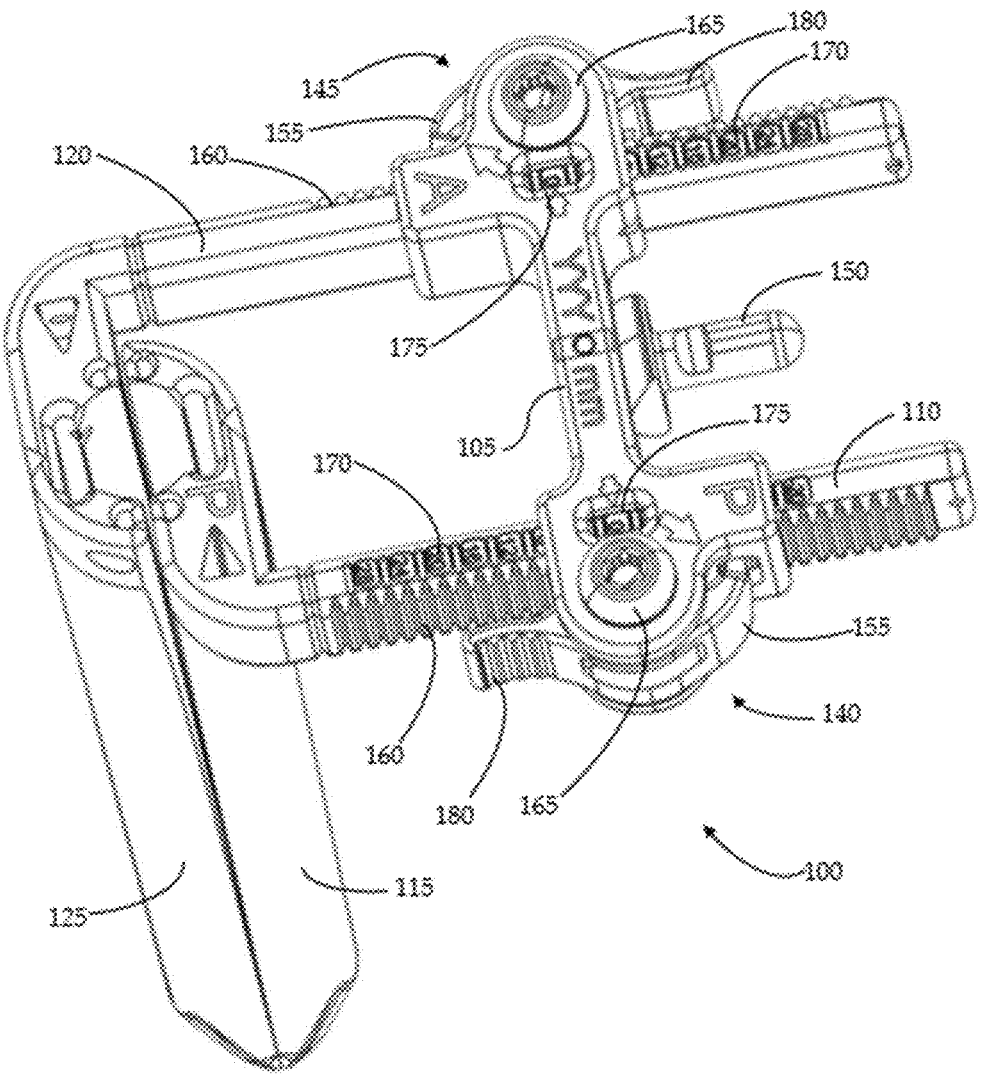
FIG. 2 illustrates another perspective view of the embodiment shown in FIG. 1.

FIG. 2 illustrates retractor 100 at a slightly different angle to better illustrate adjustment mechanisms 140, 145 each of which includes a pawl 155 configured to engage a set of teeth 160 on each retractor arm. Each adjustment mechanism further includes a toothed shaft 165 (at least partially visible in FIG. 5) that when rotated clockwise moves the retractor arm either proximally (as is the case with proximal retractor arm 110) or anteriorly (as is the case with anterior retractor arm 120). As retractor arms 110, 120 are advanced relative to base portion 105, markings 170 on each retractor arm are visible through indicator windows 175. In some embodiments, markings 170 are placed at increments of 0.5 mm, 1 mm, 2 mm, 3 mm, 4 mm, or some value between those values. Markings 170 correlate to the size and spacing of teeth 160 along retractor arms 110, 120 and indicate the displacement of each retractor arm from a "zero" position.

Advancing retractor arms 110, 120 expands the surgical corridor. Retractor arms 110, 120 may also be released or allowed to return to their original positions as to allow adjustment of the surgical corridor or removal of retractor blades 115, 125 from the surgical site by pressing one or both of levers 180, which disengages pawls 155 from teeth 160. By holding down one lever (either on the posterior or anterior side) while rotating the toothed shaft on the other side, a user can translate both anterior arm 120 and posterior arm 110 in unison. This may be desirable when a user desires to move retractor 100 to improve its positioning but where the user does not want to adjust the surgical support to which retractor 100 is clamped or secured.

Figure 3:
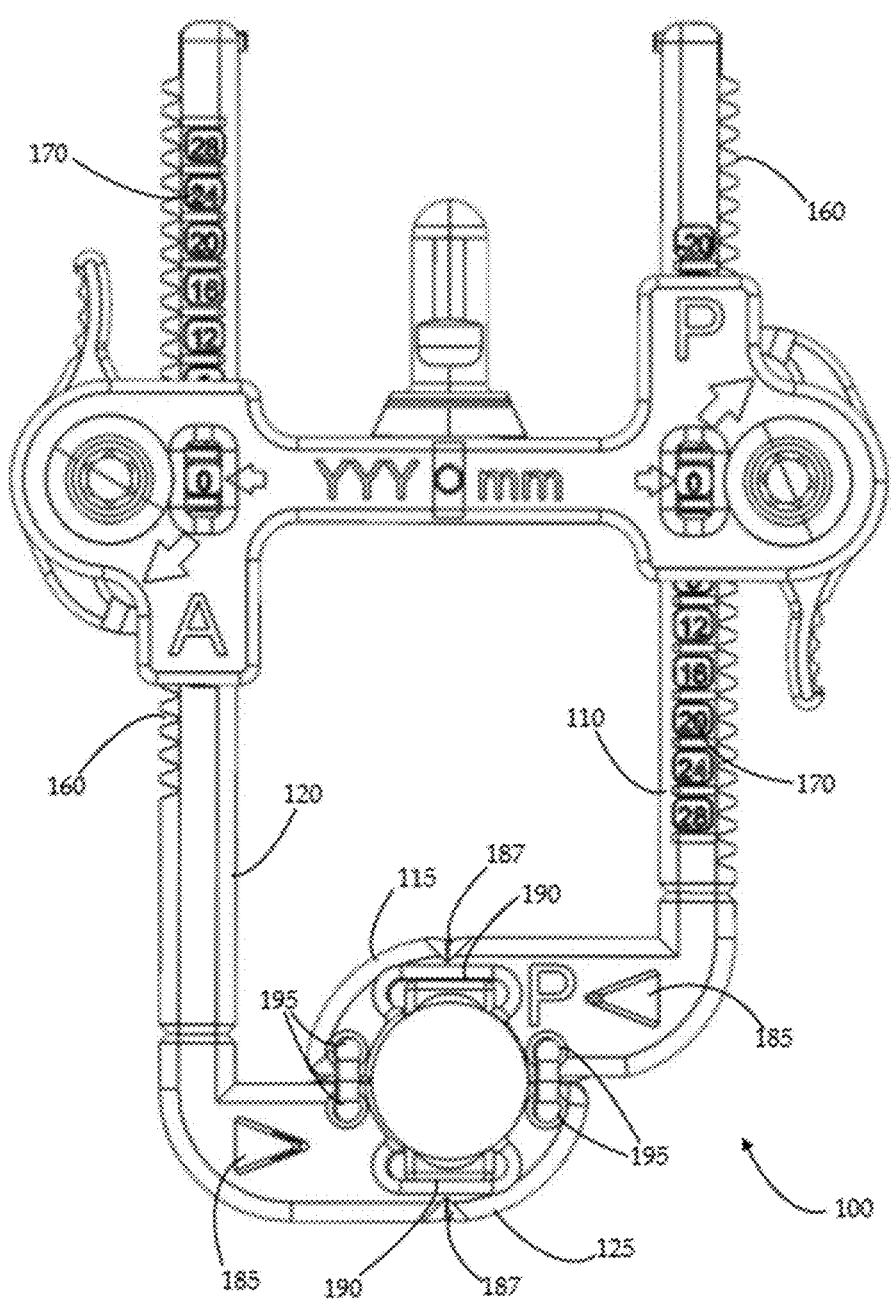
FIG. 3 illustrates a top down view of the surgical retractor shown in FIG. 1.

FIG. 3 illustrates retractor 100 from above or, in other words, along the surgical corridor created by posterior retractor blade 115 and anterior retractor blade 125. This perspective also illustrates that posterior retractor arm 110 and anterior retractor arm 120 each include an alignment feature 185 and that the respective proximal ends of posterior blade 115 and anterior blade 125 each include additional alignment feature 187. In this embodiment, alignment feature 185 is a triangular bore that extends from a top surface of each retractor arm to a bottom surface. Additional alignment feature 187 is an angled cut on the outer surface of each blade. Both alignment feature 185 and additional alignment feature 187 are configured to provide a surgeon with an indication of the orthogonality of retractor 100 relative to the patient's disc space. Such orthogonality is achieved by creating an incision in a patient to access the disc space from a lateral approach, positioning retractor 100 in the incision, and then confirming the position of retractor 100 using radiographic images of the disc space. The indication of orthogonality is achieved when the alignment features 185 are fully visible in the radiographic image, which image has been arranged to look directly at the target space along a perspective orthogonal to that disc space.

Although illustrated as triangular in shape, alignment features 185 may be formed using any other suitable shape, such as a circle, a square, etc. And although alignment features 185 in this embodiment are bores that extend from a top surface to a bottom surface, partial bores may provide the desired amount of radiolucency. Alternatively, if retractor arms 110, 120 are somewhat radiolucent themselves, alignment features 185 may comprise radiopaque markers, such as a radiopaque material embedded or applied to retractor arms 110, 120.

FIG. 3 also illustrates that retractor blades 115, 125 each include a central channel 190 as well as two lateral channels 195. In some embodiments, central channel is configured to receive at least one of a light cable, a tissue shim, an intradiscal shim, an anchoring shim, a blade extender, or any other suitable device. In some embodiments, at least one of lateral channels 195 is configured to receive an anchor device, such as a bone screw the head of which mates with lateral channel 195, a light cable, tissue shim, auxiliary retraction device, etc.

Looking down the opening created between retractor blades 115, 125 highlights the circular shape of the opening. In some embodiments, however, the opening will have other shapes, such as oval or oblong. Although not illustrated, such non-circular shapes are achieved in some embodiments by expanding the width of retractor blades 115, 125 compared to their depth or thickness.

In some embodiments, the shape of the opening between retractor blades 115, 125 may be determined by the shape of the type of implant intended to be surgically implanted in a patient's body. For example, wider implants may require a wider surgical corridor, but rather than simply expanding the corridor in all directions, using oval-shaped blades will enlarge the corridor in one direction without requiring a larger corridor in all directions thereby reducing trauma to surrounding tissue and nerves.

In some embodiments, the shape of the opening is determined by the shape of dilators that are used to chart the path toward the surgical site and create the surgical corridor. For example, where cylindrical dilators are used, using a retractor with circular-shaped blades may provide the best engagement to allow for a working corridor to be created, whereas oval-shaped dilators may require or at least suggest the use of a retractor whose blades together form an oval-shaped opening or corridor.

Figure 4:
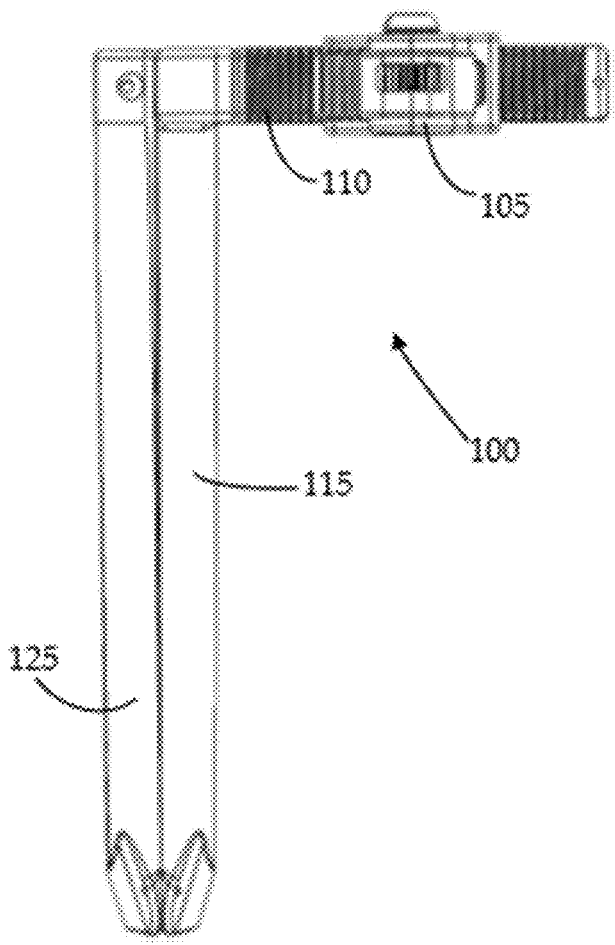
FIG. 4 illustrates a side view of the surgical retractor shown in FIG. 1.

FIG. 4 is a side or lateral view of retractor 100 and illustrates the desired orthogonality between retractor arms 110, 120 and retractor blades 115, 125, which is achieved in part by securely maintaining retractor arms 110, 120 in line with base portion 105. FIG. 4 also illustrates the generally cylindrical shape of retractor blades 115, 125 especially when blades 115, 125 are positioned to abut each other; however, and as illustrated, some embodiments include retractor blades that taper toward the distal end. In some embodiments, such tapering is limited to the outside surfaces of the retractor blade. In other words, the inside surfaces of the retractor blades together maintain a consistent cylindrical path along their respective lengths.

Figure 5:
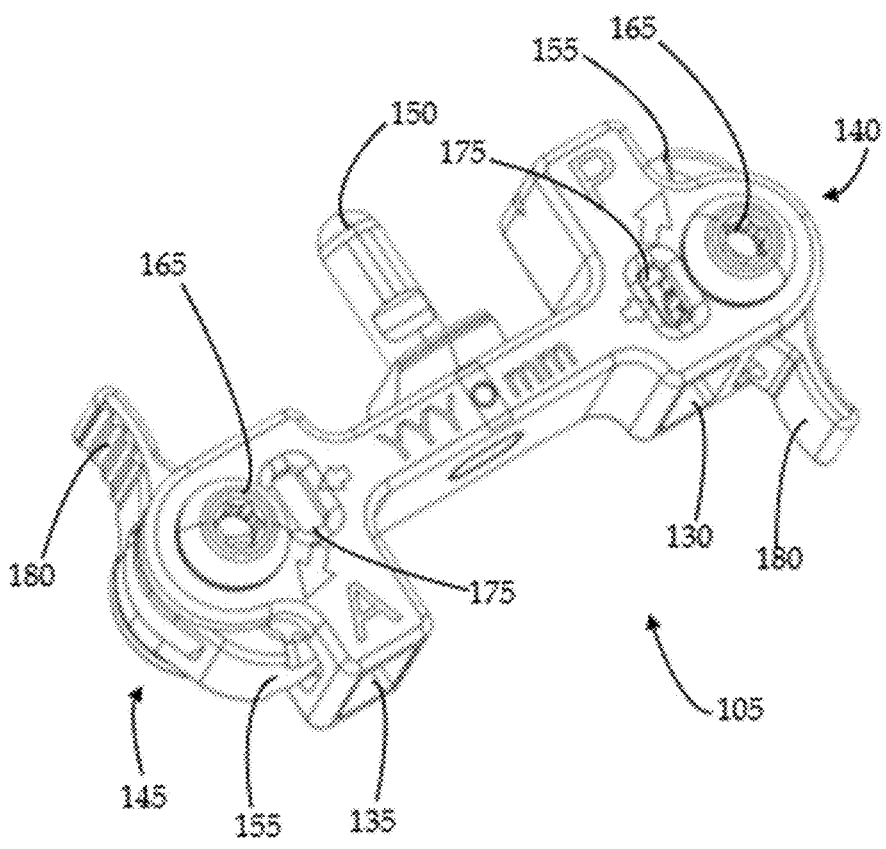
FIG. 5 illustrates a perspective view of a base portion, which is a component of the surgical retractor shown in FIG. 1.

FIG. 5 illustrates base portion 105 in isolation. Without retractor arm 110 inserted through receiving area 130, it is possible to see the toothed portion of toothed shaft 165 through indicator window 175. For ease of use, each end or extension of base portion is labeled with either an "A" for "anterior" or a "P" for posterior, which indicates not only which retractor arm to insert into which receiving area but also provides a ready reminder for how to position retractor 100 relative to the patient and, in particular, the disc space to be accessed.

Figure 6:
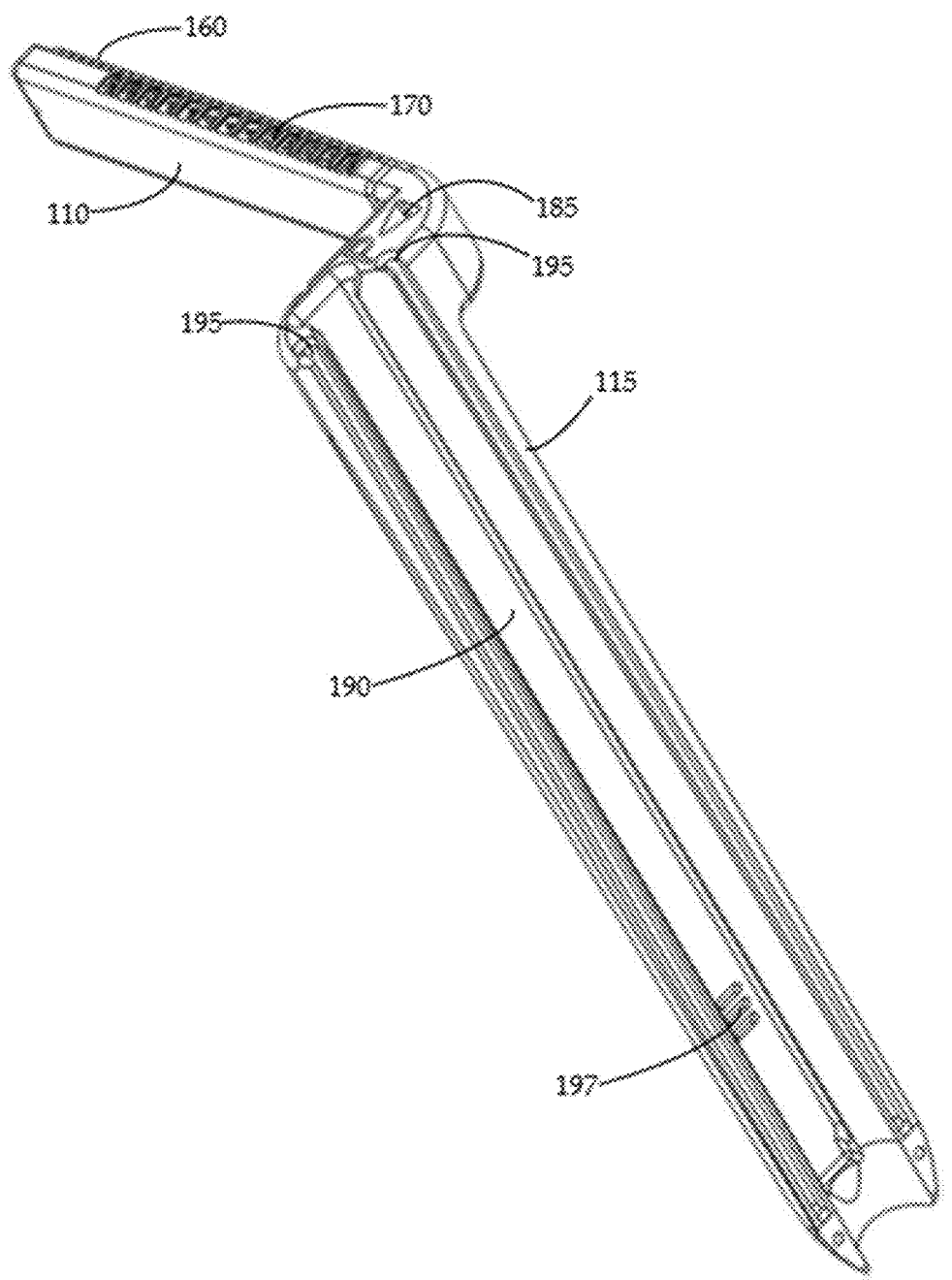
FIG. 6 illustrates a perspective view of a surgical arm and blade, which is a component of the surgical retractor shown in FIG. 1.

FIG. 6 illustrates posterior retractor arm 110 and posterior retractor blade 115, which in this embodiment are constructed to form a unitary piece. In some embodiments, the retractor arm and blade consist of a single unit. In some embodiments, the arm and blade are irreversibly secured to each other to essentially form a single unit. In some embodiments, the blade and arm are reversibly attached to each other.

Central channel 190 is shown as extending almost the entire length of blade 115 with one opening at the proximal end of blade 115. In some embodiments, central channel 190 extends the full length of blade 115 meaning that it opens at both the proximal and distal ends of blade 115. In this illustrated embodiment, central channel 190 includes depressions 197 that are configured to provide various locking or stopping points for tools that are inserted into the surgical corridor along central channel 190. For example, an intradiscal shim may be locked in position relative blade 115 when an extension or tab on the shim is able to extend into one of depressions 197. Although not illustrated in FIG. 7, similar depressions may be incorporated into the central channel of anterior retractor blade 125.

Figure 7:
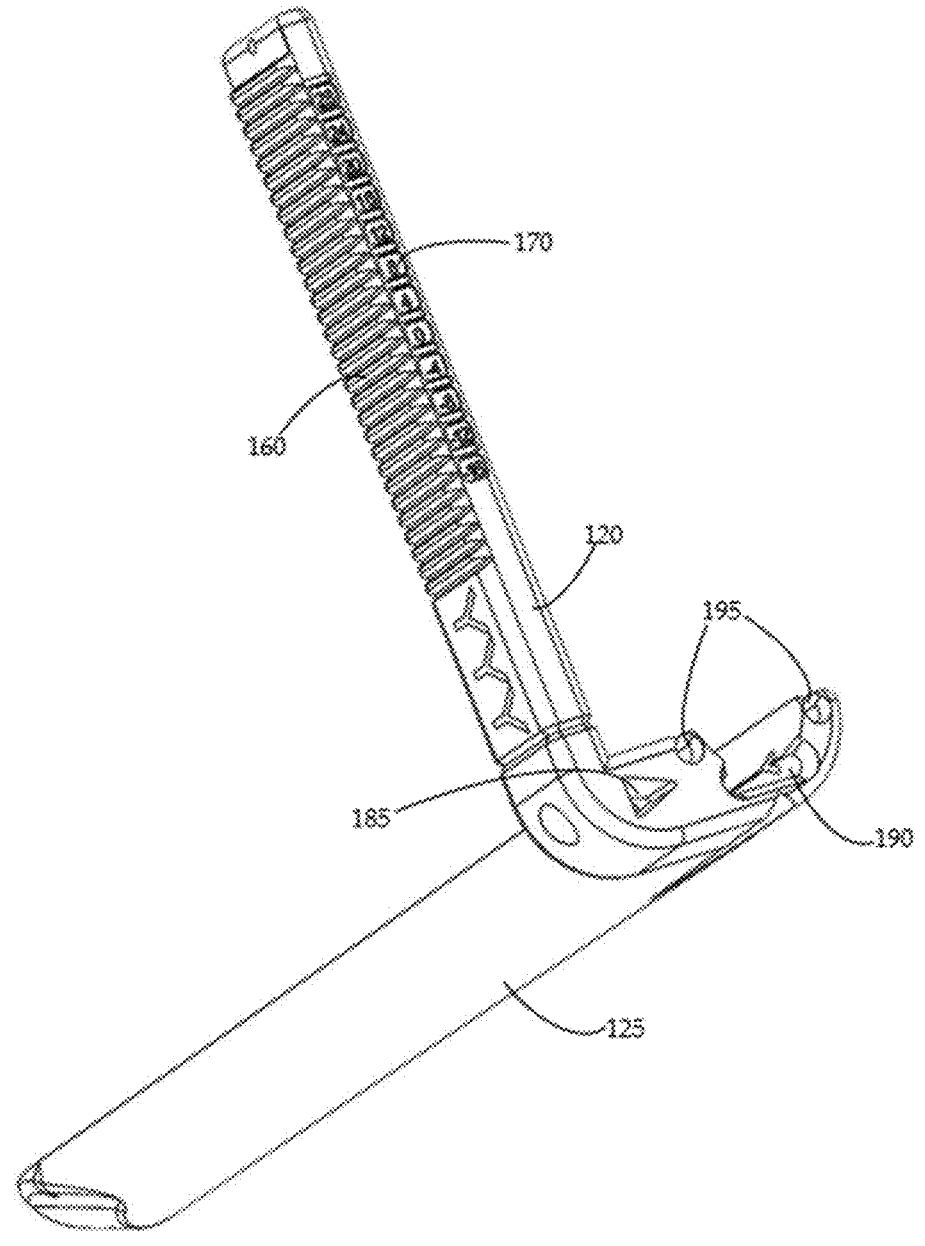
FIG. 7 illustrates a perspective view of a surgical arm and blade, which is a component of the surgical retractor shown in FIG. 1.

FIG. 7 illustrates anterior retractor arm 120 and anterior retractor blade 125 that are shown as constructed to form a unitary piece. Similar to arm 110 and blade 115, arm 120 and blade 125 may consist of a single unit or may be secured to result in a single unit or may be reversibly secured to each other.

Methods for using surgical retractor 100 and similar retractors consistent with the present disclosure include a number of preparation steps. For example, referring briefly to FIG. 46, in some embodiments, such preparation begins with positioning a patient in a prone position, a lateral decubitus position, a supine position, or any other suitable patient position. Subsequent preparation includes identifying an incision point for accessing a desired surgical site, creating an incision, and advancing an instrument guide—such as a guide wire or a K-wire—to the surgical site. The instrument guide may be advanced through at least a portion of the psoas muscle in order to achieve a trans-psoas procedure.

With initial access to the surgical site established, some embodiments include advancing one or more sequential dilators along the instrument guide through the incision and down to the surgical site. One or more of the sequential dilators may be configured to provide for neural monitoring and/or nerve detection. The sequential dilators may have a circular cross section or an oval-shaped cross section. In some embodiments, a suitable retractor—such as surgical retractor 100—is advanced over the outermost dilator until the distal end of the retractor contacts or is sufficiently near the surgical site or disc space, after which the dilator(s) may be removed so as to allow retractor 100 to create a surgical corridor to access the surgical site.

Once positioned, retractor 100 may be secured to a surgical support, such as A-arm that is secured to a frame, surgical bed, or surgical table. In some embodiments, one of the surgical retractor's blades—such as posterior blade 115—is positioned posteriorly of the disc space. Such positioning may be accomplished by adjusting the surgical support (e.g., an A-arm) or by manipulating adjustment mechanism 140 to move posterior blade 115 posteriorly. Once properly positioned, an anchor or intradiscal shim is advanced down into the surgical corridor along either central channel 190 or one of lateral channels 195 to be placed in either bone or the intradiscal space to fix posterior blade 115 relative to the disc space.

A surgeon or user then operates one or both of adjustment mechanisms 140, 145 to expand the surgical corridor by moving anterior blade 125 anteriorly until a desirably sized surgical corridor is created at which point anterior blade 125 may be anchored using an anchor screw or an intradiscal shim or any other suitable anchoring mechanism.

Figure 8:
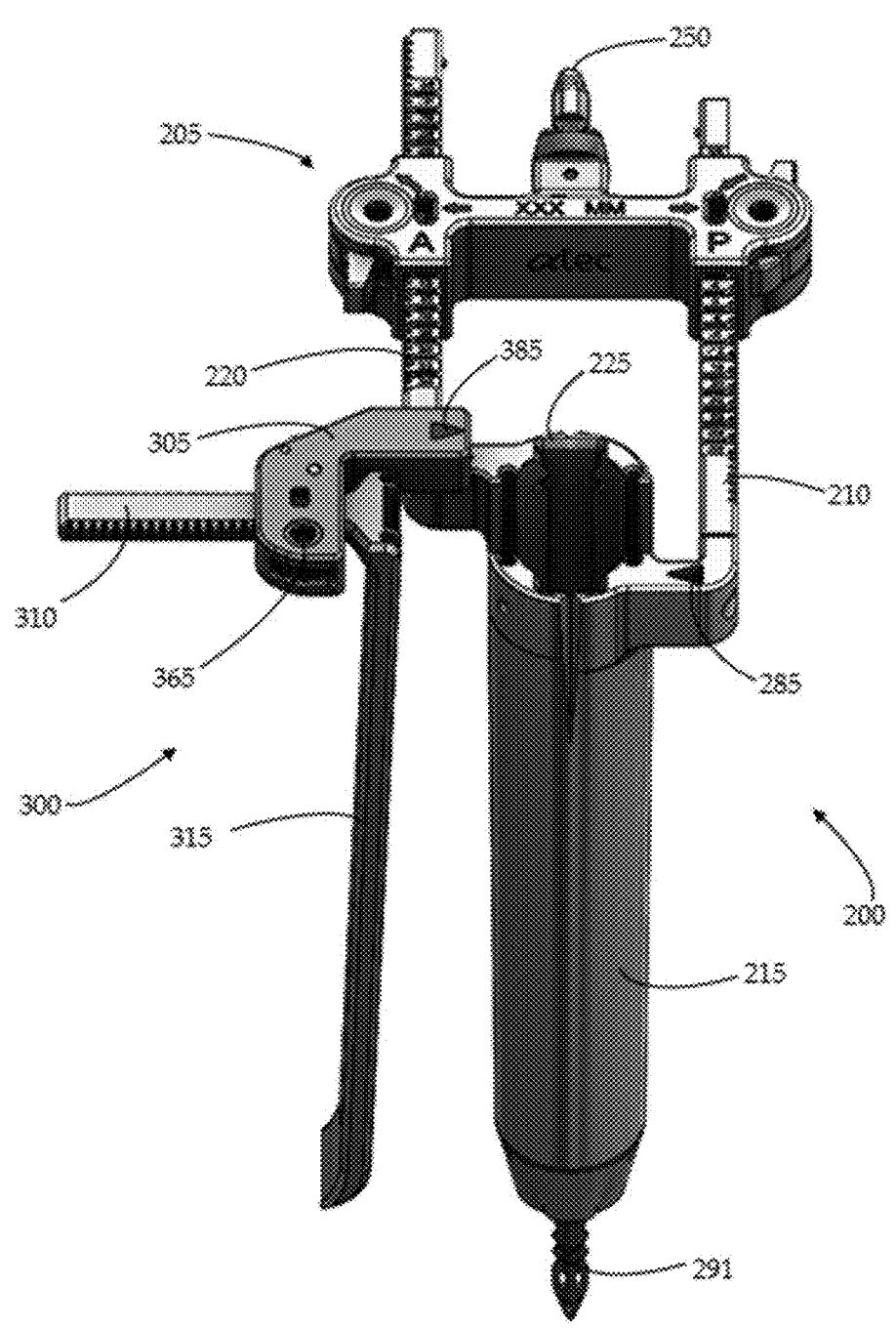
FIG. 8 illustrates a perspective view of a surgical retractor according to the present disclosure that includes an auxiliary retractor blade.

FIG. 8 illustrates an embodiment of a surgical retractor 200, which in many respects is similar to retractor 100; however, it will be noticed that the relative positions of posterior retractor blade 215 and anterior retractor blade 225 are reversed compared to posterior retractor blade 115 and anterior retractor blade 125. In some embodiments, one orientation is preferable over the other orientation. This embodiment is also illustrated with an intradiscal shim 291 positioned within the channel of posterior blade 215. As is discussed elsewhere in this document, the one or more channels in the retractor blades may be configured to receive any number of attachments or accessories, such as tissue shims of various sizes and shapes, intradiscal shims, light cables, bone anchors, etc.

FIG. 8 also illustrates that a surgical retractor according to the present disclosure, such as retractor 200, may be configured to receive one or more modular blade assemblies, such as modular blade assembly 300 that includes a base portion 305, a blade arm 310, and an auxiliary blade 315. Modular blade assembly 300 includes many features found on retractors 100 and 200, such as an adjustment mechanism 365 that, when rotated, adjusts the position of auxiliary blade 315 relative to posterior blade 215 and anterior blade 225, which adjustment increases or decreases the surgical corridor created by the various retractor blades. Modular blade assembly 300 is designed to snap onto or otherwise securely attached to anterior blade arm 220. Some embodiments of modular blade assemblies, such as will be discussed in greater detail below, are configured to be snapped onto or otherwise securely attached to posterior blade arm 210.

Blade arm 310 is movable with respect to base portion 305 and may, in some embodiments, be entirely removed from base portion 305. This modularity allows for the use of different base portions with different blades. Different designs for base portions and different designs for blades are discussed in greater detail below. In some embodiments, a set of instruments for a modular blade assembly includes (1) a single base portion and two or more distinct retractor blades, (2) two or more base portions and a single retractor blade, or (3) two or more base portions and two or more retractor blades. In some embodiments, it may be advantageous to use different arrangements of base portions and/or retractor blades during a single procedure as the needs of the user change over the course of the procedure.

Modular blade assembly also includes an alignment feature 385. In this embodiment, alignment feature 385 is a triangular-shaped through-hole in base portion 305 that aligns with an alignment feature located on anterior blade arm 220 (not illustrated, though similar to alignment feature 285 of posterior blade arm 210). This alignment is designed to not inhibit a user's ability to use the alignment feature on retractor 200. In some embodiments, alignment feature 385 is designed to enhance the functionality of the alignment feature on the retractor arm. Although in this illustrated embodiment, alignment feature 385 is shaped and sized to be substantially the same as the underlying alignment feature, in some embodiments, alignment feature 385 has a different shape from the underlying alignment feature and/or is larger or smaller than the underlying alignment feature.

Figure 9:
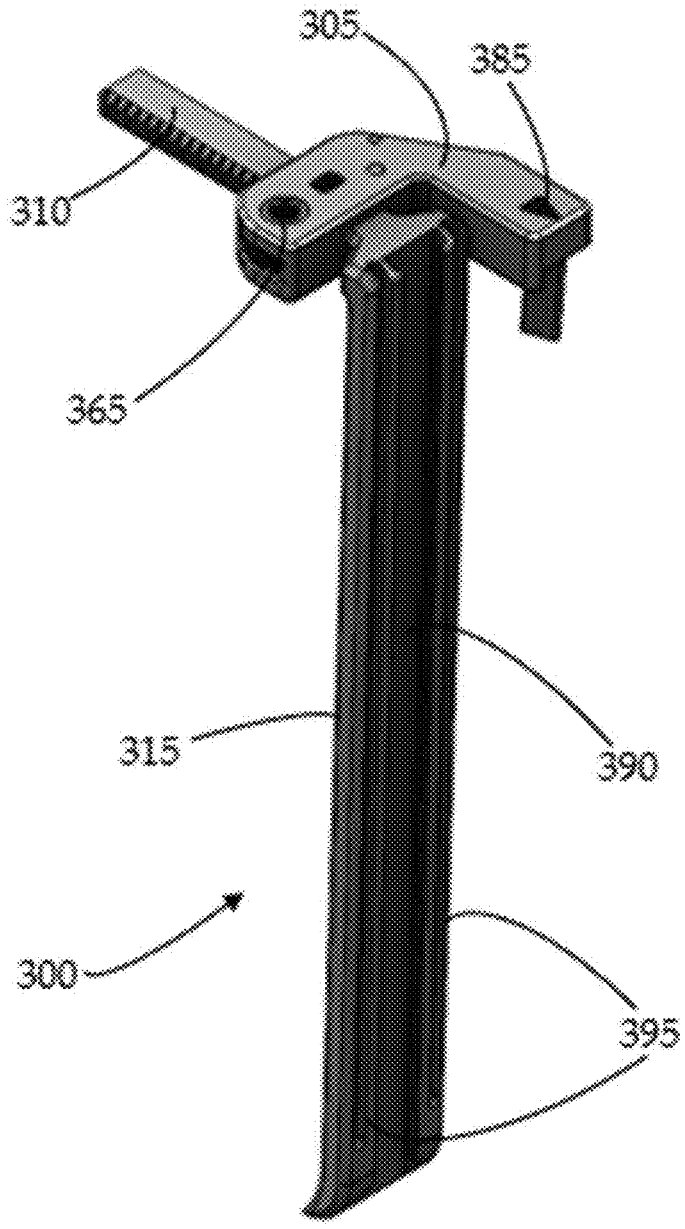
FIG. 9 illustrates a perspective view of one embodiment of an auxiliary retractor blade according to the present disclosure.
Figure 10:
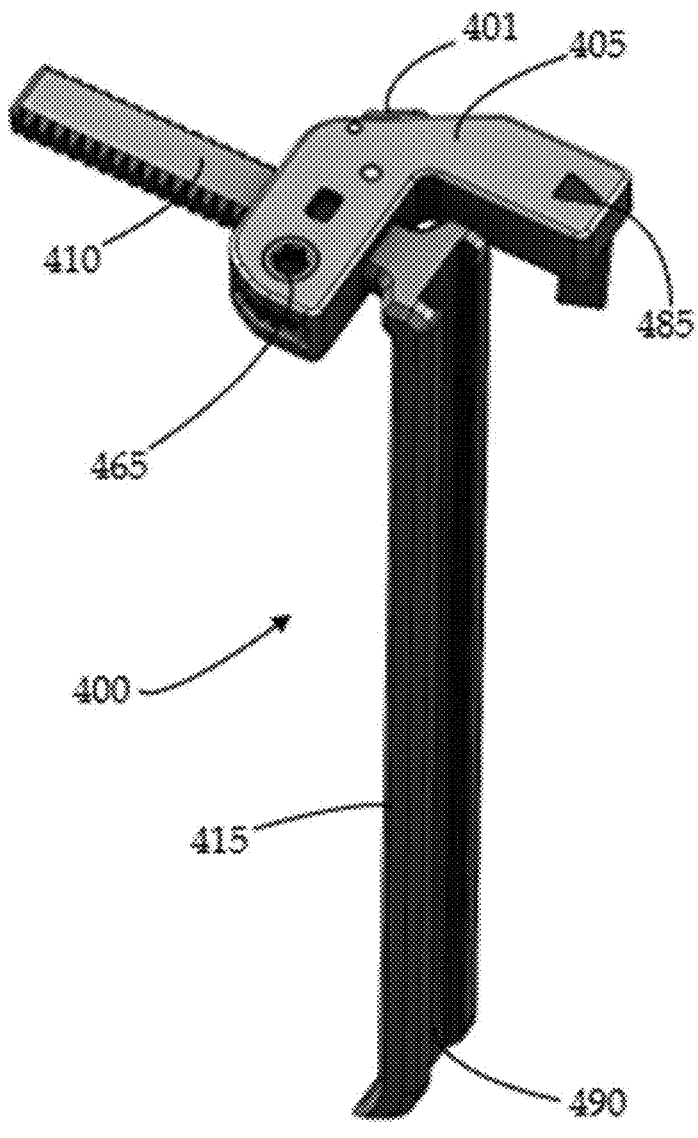
FIG. 10 illustrates a perspective view of another embodiment of an auxiliary retractor blade according to the present disclosure.
Figure 11:
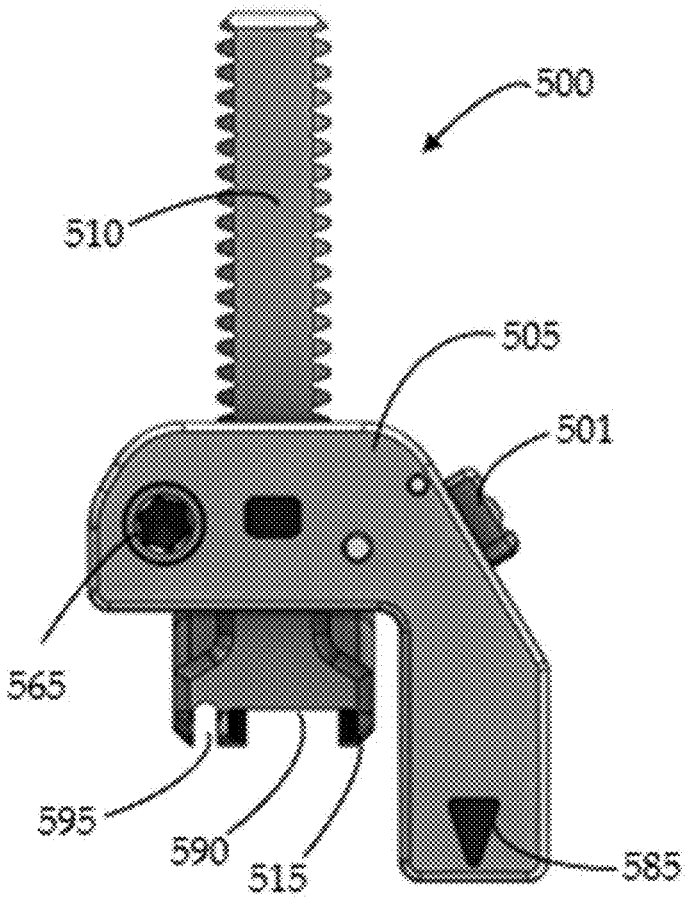
FIG. 11 illustrates a top view of yet another embodiment of an auxiliary retractor blade according to the present disclosure.

FIGS. 9-11 illustrate three different embodiments of modular blade assemblies each of which is configured for attachment to an anterior blade arm of a retractor according to the present disclosure; however, a skilled artisan will understand that the features of these disclosed embodiments could be equally applied to modular blade assemblies that are configured to be attached to a posterior blade arm.

FIG. 9 illustrates that auxiliary blade 315 of modular blade assembly 300 includes both a central channel 390 as well as two lateral channels 395. In some embodiments, central channel 390 is configured to receive any one of a tissue shim, intradiscal shim, and/or a light cable. In some embodiments, lateral channels 395 are configured to receive at least a portion of a bone anchor so as to anchor or secure in position auxiliary blade 315 relative to a surgical site.

FIG. 10 illustrates an embodiment of a modular blade assembly 400 that is similar to modular blade assembly 300; however, auxiliary blade 415 includes only a central channel 490 and not lateral channels. Also visible in FIG. 10 is the presence of release mechanism 401 that is configured to provide a quick release for blade arm 410. In some embodiments, release mechanism 401 operates by sliding back and forth. In some embodiments, release mechanism 401 operates as a push button that is depressed to release blade arm 410. When release mechanism 401 is activated, blade arm 410 may slide freely relative to body portion 405.

FIG. 11 illustrates an embodiment of a modular blade assembly 500 that is similar to modular blade assemblies 300 and 400; however, auxiliary blade 515 includes a central channel 590 and only one lateral channel 595 to the left of central channel 590. In some embodiments, lateral channel 595 is positioned to the right of central channel 590.

Figure 12:
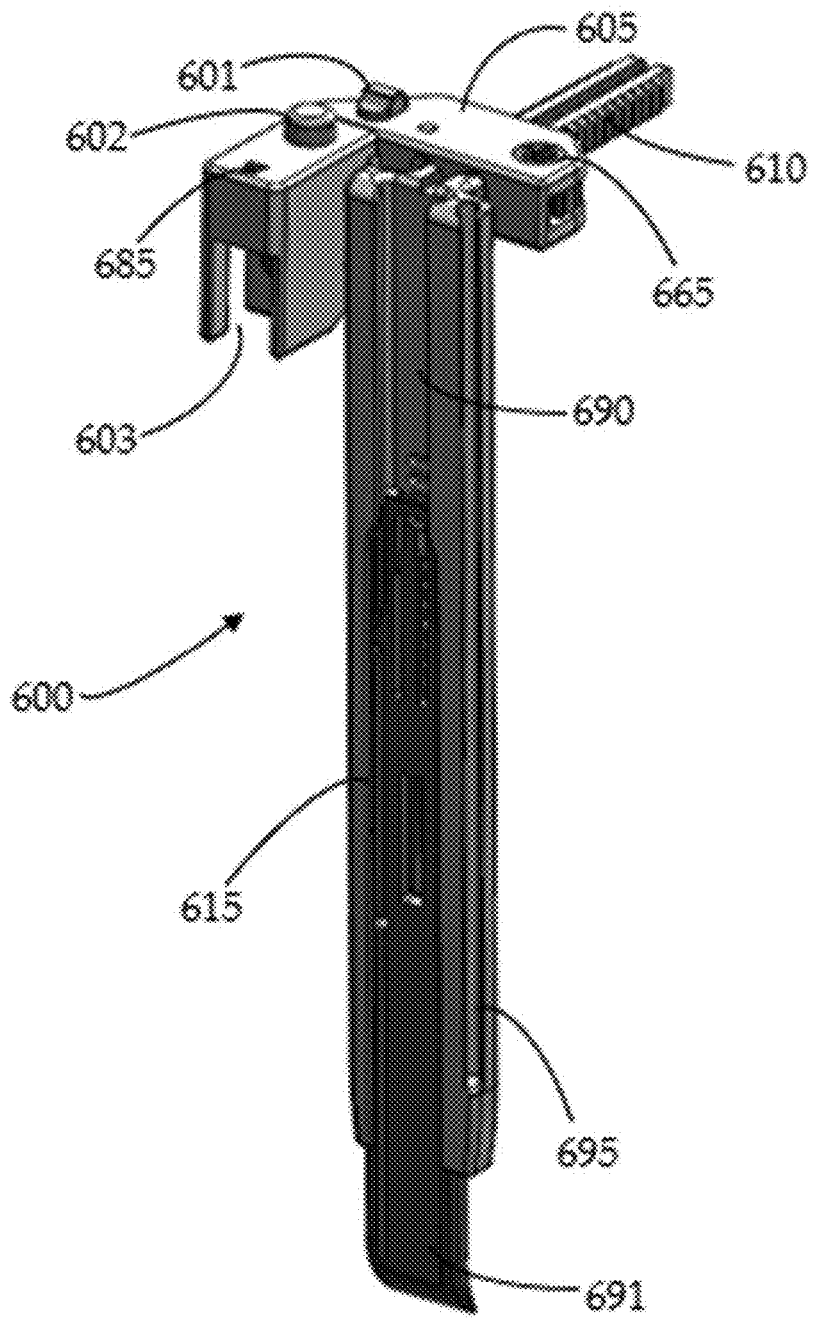
FIG. 12 illustrates a perspective view of yet another embodiment of an auxiliary retractor blade according to the present disclosure.

FIG. 12 illustrates an embodiment of a modular blade assembly 600 that is similar to modular blade assemblies 300, 400, and 500 with a primary difference being that modular blade assembly 600 is configured to be attached to posterior blade arm 210. FIG. 12 also provides a view of receiving area 603 on the underside of base portion 605. It is within this receiving area that a portion of posterior blade arm 210 is inserted. Modular blade assembly 600 also includes a release mechanism 602 configured to trigger disengagement from posterior blade arm 210. As illustrated, release mechanism 602 is a push button mechanism; however, in some embodiments, a toggle mechanism is used as well as any other number of suitable mechanisms. This illustrated embodiment also includes a tissue shim 691 positioned in central channel 690.

Figure 13:
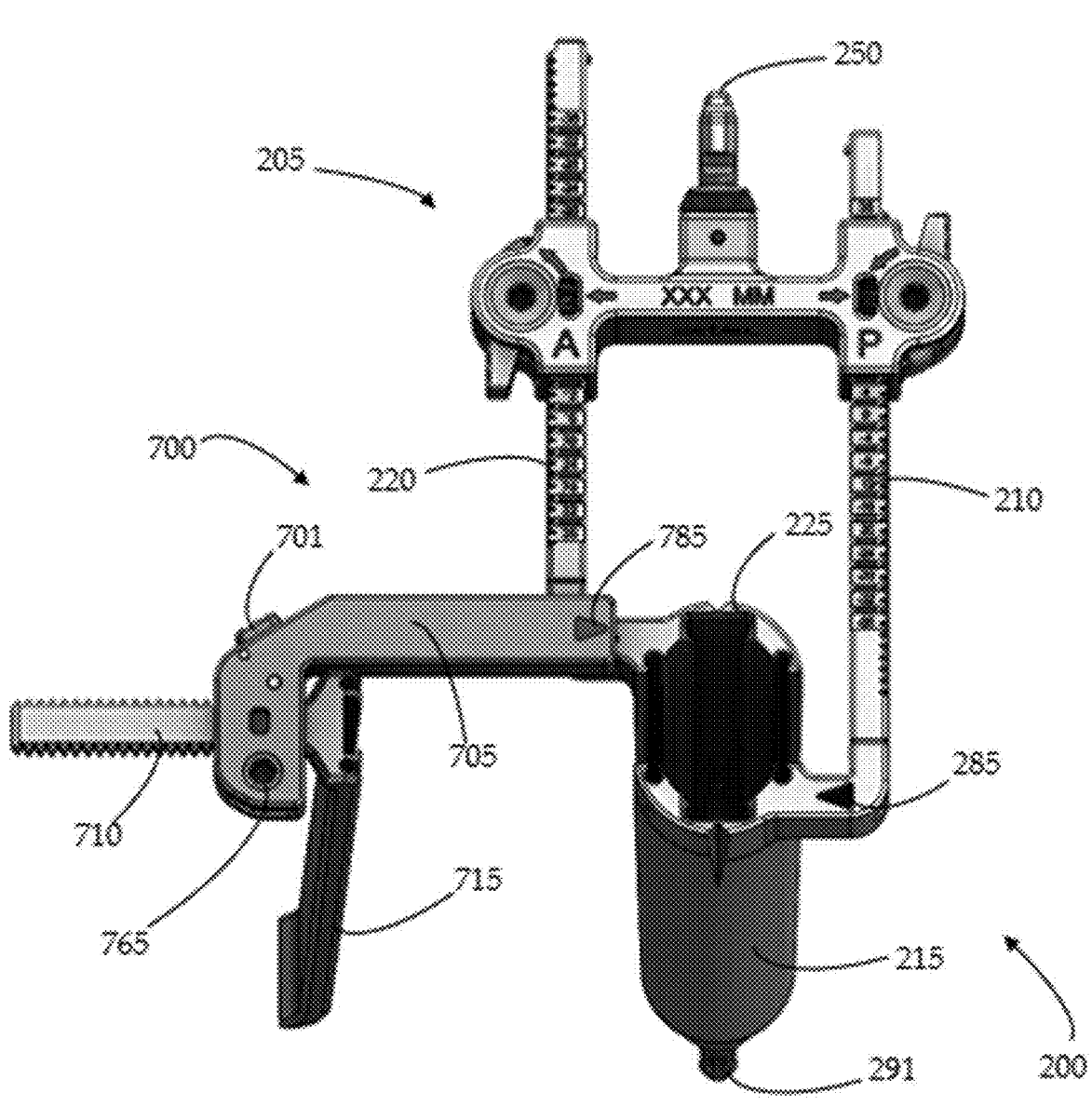
FIG. 13 illustrates a perspective view of the surgical retractor of FIG. 8 that includes a different embodiment of an auxiliary retractor blade according to the present disclosure.

FIG. 13 illustrates an embodiment of a modular blade assembly 700 secured to anterior blade arm 220 of retractor 200. Modular blade assembly 700 is similar in many respects to modular blade assemblies 300, 400, 500, and 600 with a key distinction being the elongated portion of base portion 705. Such a design allows for the creation of much larger surgical corridors. For example, where the surgery to be performed involves only a single intervertebral disc, a smaller surgical corridor may be desired to minimize any trauma to surrounding tissue. However, in some surgeries it may be desirable to access two or more vertebral disc spaces through a single approach rather than creating a separate surgical corridor for each disc space. Modular blade assembly 700 is designed for such situations by including the elongated portion, which may be any suitable length to achieve the desired size of surgical corridor.

Figure 14:
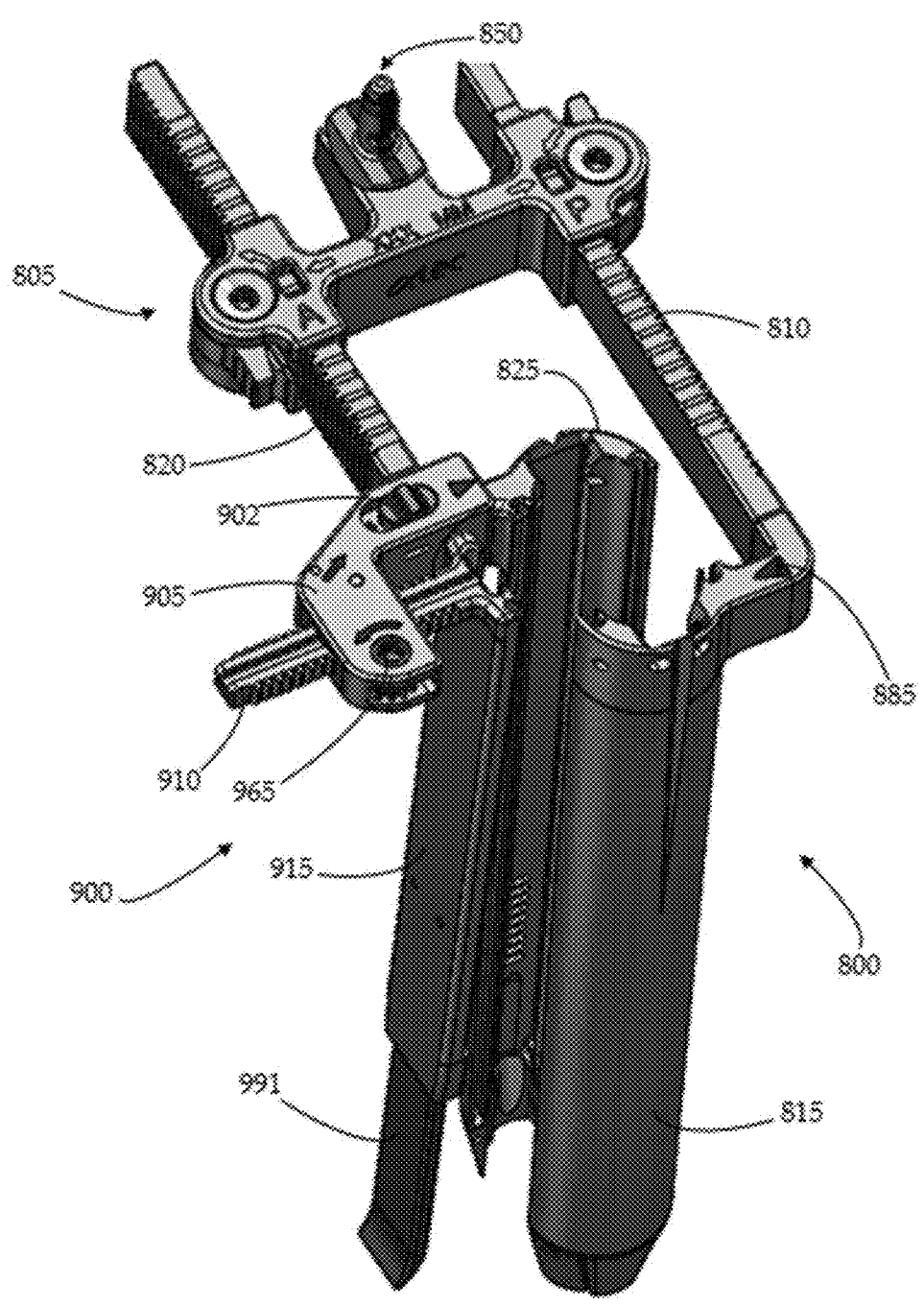
FIG. 14 illustrates a perspective view of a surgical retractor according to the present disclosure that includes an auxiliary retractor blade.

FIG. 14 illustrates an embodiment of a surgical retractor 800 that includes a modular retractor blade 900. Surgical retractor 800 is similar in many aspects to retractors 100 and 200 with a key distinction being that posterior blade 815 and anterior blade 825, together, are oval-shaped rather than circular in shape. Such a variation in shape may be advantageous in certain surgical procedures.

Modular blade assembly 900 is similar in many aspects to modular blade assemblies 300, 400, 500, 600, and 700. Modular blade assembly 900 includes a release mechanism 902 that, in this embodiment, is a toggle mechanism. Release mechanism 902 is configured to maintain modular blade assembly in a locked arrangement with anterior blade arm 820 but to then, when toggled, to allow for modular blade assembly 900 to be easily removed from anterior blade arm 820. Modular blade assembly is also shown as including a tissue shim 991.

Figure 15:
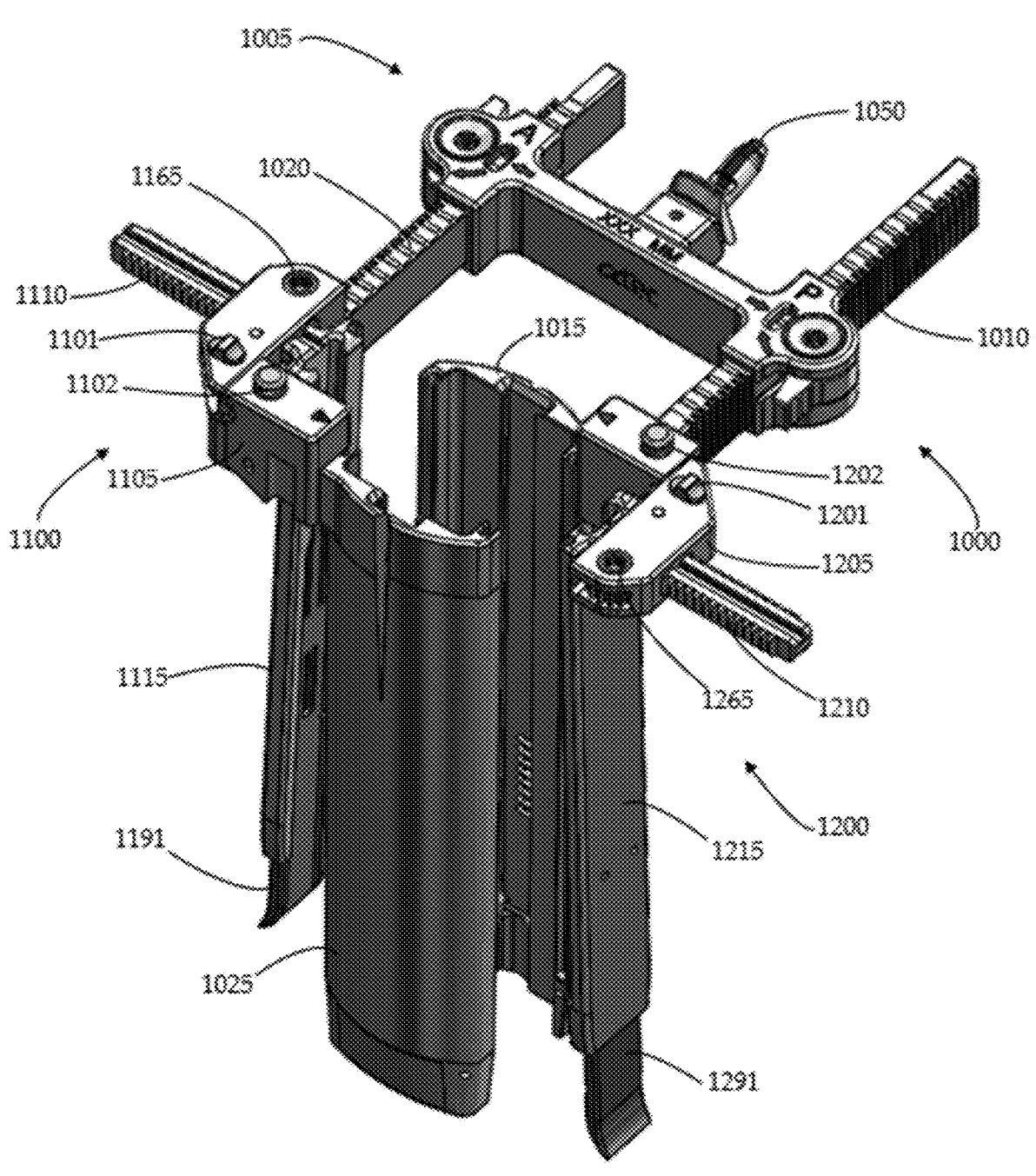
FIG. 15 illustrates a perspective view of a surgical retractor according to the present disclosure that includes two auxiliary retractor blades.

FIG. 15 illustrates an embodiment of a surgical retractor 1000 that includes an anterior modular retractor blade 1100 as well as a posterior modular retractor blade 1200. Surgical retractor 1000 is similar in many aspects to retractors 100, 200, and 800 with a key distinction being that posterior blade 1015 and anterior blade 1025, together, are somewhat rectangular in shape rather than oval-shaped or circular in shape. Such a variation in shape may be advantageous in certain surgical procedures.

Modular blade assembly 900 is similar in many aspects to modular blade assemblies 300, 400, 500, 600, and 700. Modular blade assembly 900 includes a release mechanism 902 that, in this embodiment, is a toggle mechanism. Release mechanism 902 is configured to maintain modular blade assembly in a locked arrangement with anterior blade arm 820 but then, when toggled, to allow for modular blade assembly 900 to be easily removed from anterior blade arm 820. Modular blade assembly is also shown as including a tissue shim 991.

Modular blade assemblies 1100 and 1200 are similar in many aspects to modular blade assemblies 300, 400, 500, 600, 700, and 900. The use of both modular blade assembly 1100 and modular blade assembly 1200 on a single retractor 1000 illustrates how the simple two-blade design of retractor 1000 can easily be modified to establish a surgical corridor with four blades each having one or more channels to accommodate tissue shims, such as tissue shims 1191 and 1291, intradiscal shims, and light cables.

According to some embodiments, it may be desirable to have available for a procedure and/or change during the procedure the types of retractor blades used in retractor 1000. For example, as access to the surgical site is achieved using one or more dilators, a user may want to be able to decide whether the ultimate surgical corridor should be generally circular, generally oval, or generally rectangular and choose retractor blades accordingly.

Accordingly, a suitable retractor system may include (1) a single retractor base portion (such as any one of base portion 105, 205, 805, or 1005), (2) two or more types of retractor blades arms (such as any one of retractor blades 115, 125, 215, 225, 815, 825, 1015, or 1025), where the retractor blades are integral with or unitary with the blade arms, and, (3) optionally, one or more of the various modular retractor assemblies disclosed herein (such as modular retractor blade assemblies 300, 400, 500, 600, 700, 900, 1100, or 1200). Some embodiments of a retractor system may exhibit additional modularity with retractor blades of differing lengths. Some embodiments of a retractor system may exhibit even more modularity with retractor blades that are not integral to the blade arms, such that any suitable or desirable blade shape/size/length may be attached to and removed from a retractor arm that is engaged to a retractor base portion.

Figure 16:
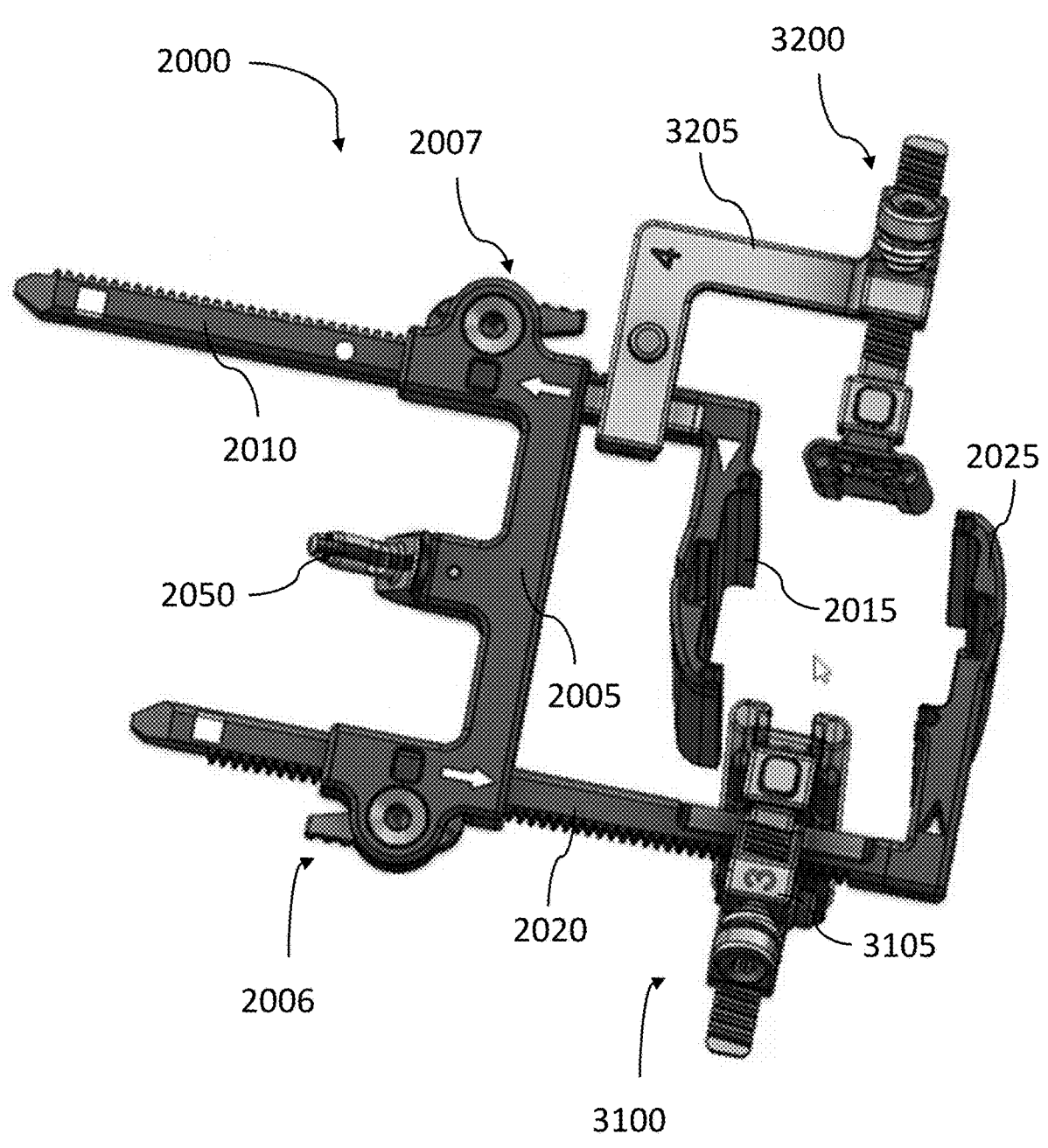
FIG. 16 illustrates a top, perspective view of another embodiment of a surgical retractor according to the present disclosure that includes two auxiliary retractor blades.

FIG. 16 illustrates a top, perspective view of another embodiment of a surgical retractor 2000 according to the present disclosure that includes two auxiliary retractor blades. The surgical retractor 2000 is similar in many aspects to retractors 100, 200, 800, and 1000 with a distinction being the inclusion of two auxiliary blades and how they attach to the surgical retractor 2000. Specifically, the surgical retractor 2000 includes a base portion 2005 connectable to an anterior arm 2020 having an anterior blade 2025, and a posterior arm 2010 having a posterior blade 2015. The anterior arm 2020 may connect to the base portion 2005 at an anterior end 2006 of the base portion 2005; the posterior arm 2010 may connect to the base portion 2005 at a posterior end 2007 of the base portion 2005.

The surgical retractor 2000 also includes modular blade assemblies 3100 and 3200. Modular blade assemblies 3100 and 3200 include many features found on retractors 100, 200, 800, and 1000, such as an adjustment mechanism 3165, 3265 that, when rotated, adjusts the position of auxiliary blades 3115, 3225 relative to posterior blade 2015 and anterior blade 2025, which adjustment increases or decreases the surgical corridor created by the various retractor blades. Modular blade assemblies 3100 and 3200 are designed to snap onto, mechanically engage, or otherwise be securely attached to anterior blade arm 2020 and/or the posterior blade arm 2010.

The modular blade assemblies 3100 and 3200 may include substantially the same components. Each of the modular blade assemblies 3100 and 3200 include a base portion (e.g., anterior base portion 3105 and posterior base portion 3205) to facilitate connection of auxiliary blades 3115 and 3215 to the anterior arm 2020 and the posterior arm 2010, respectively. The modular blade assemblies 3100 and 3200 also include blade arms 3110, 3210 to facilitate connection of the auxiliary blades 3115 and 3215 to the anterior base portion 3105 and the posterior base portion 3205, respectively.

For example, the blade arms 3110, 3210 are movable with respect to base portions 3105, 3205 and may, in some embodiments, be entirely removed from the base portions 3105, 3205. This modularity allows for the use of different base portions 3105, 3205 with different blades 3115, 3215. Different designs for base portions and different designs for blades are discussed in greater detail below. In some embodiments, a set of instruments for a modular blade assembly includes (1) a single base portion and two or more distinct retractor blades, (2) two or more base portions and a single retractor blade, or (3) two or more base portions and two or more retractor blades. In some embodiments, it may be advantageous to use different arrangements of base portions and/or retractor blades during a single procedure as the needs of the user change over the course of the procedure.

Figure 17:
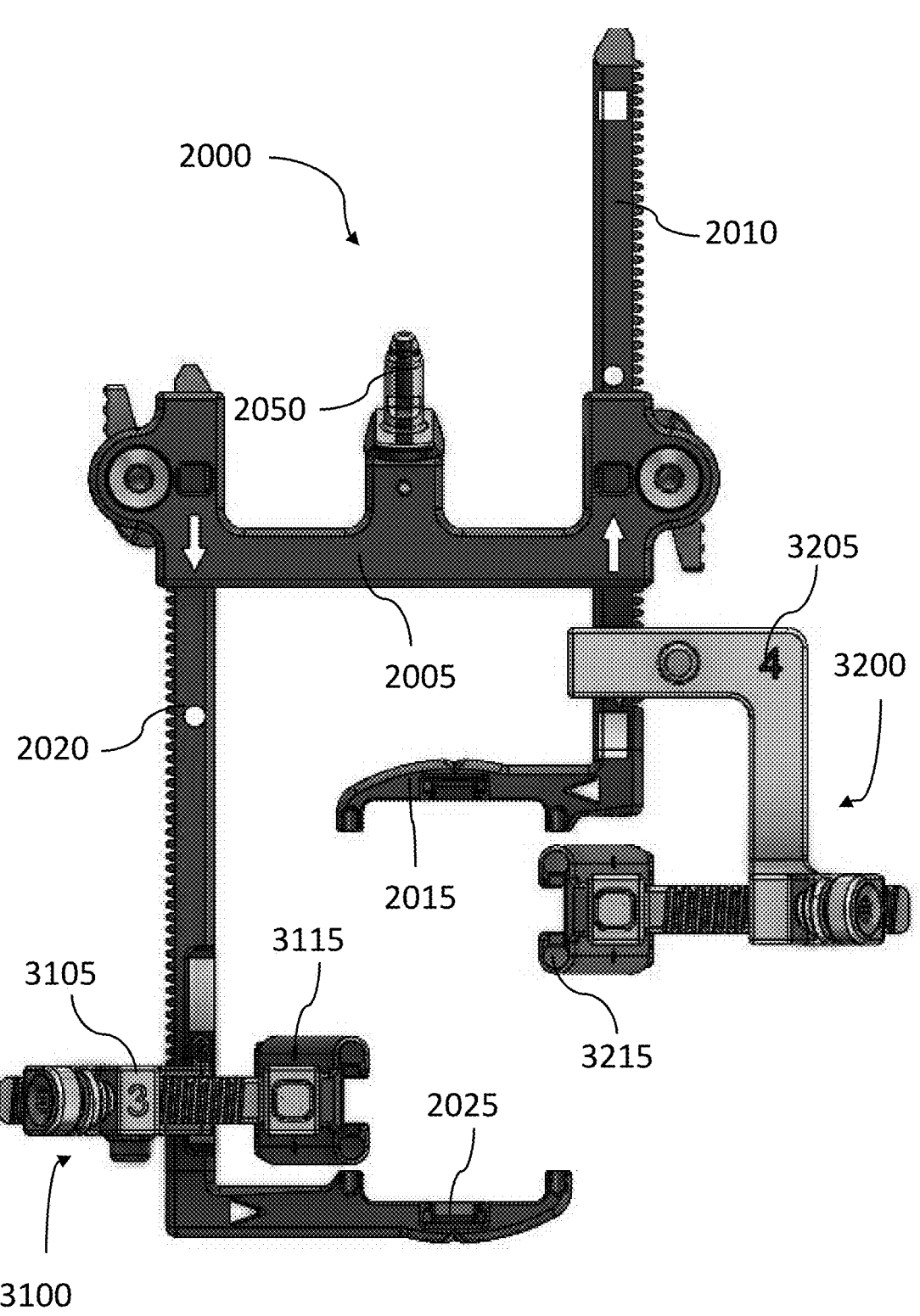
FIGS. 17 to 19 illustrate top views of the surgical retractor of FIG. 16 as the blades of the surgical retractor are moved and positioned.
Figure 18:
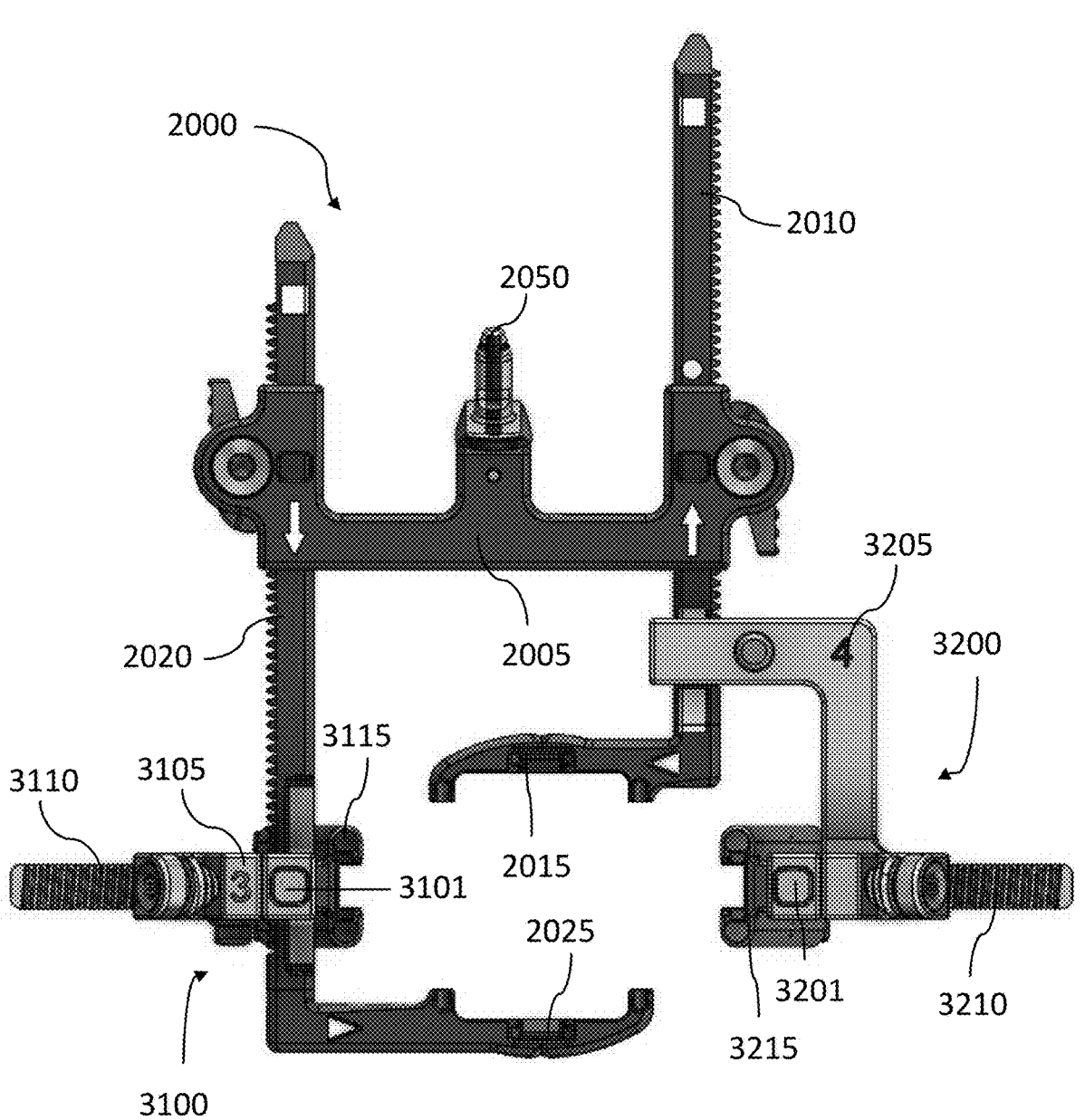
Figure 19:
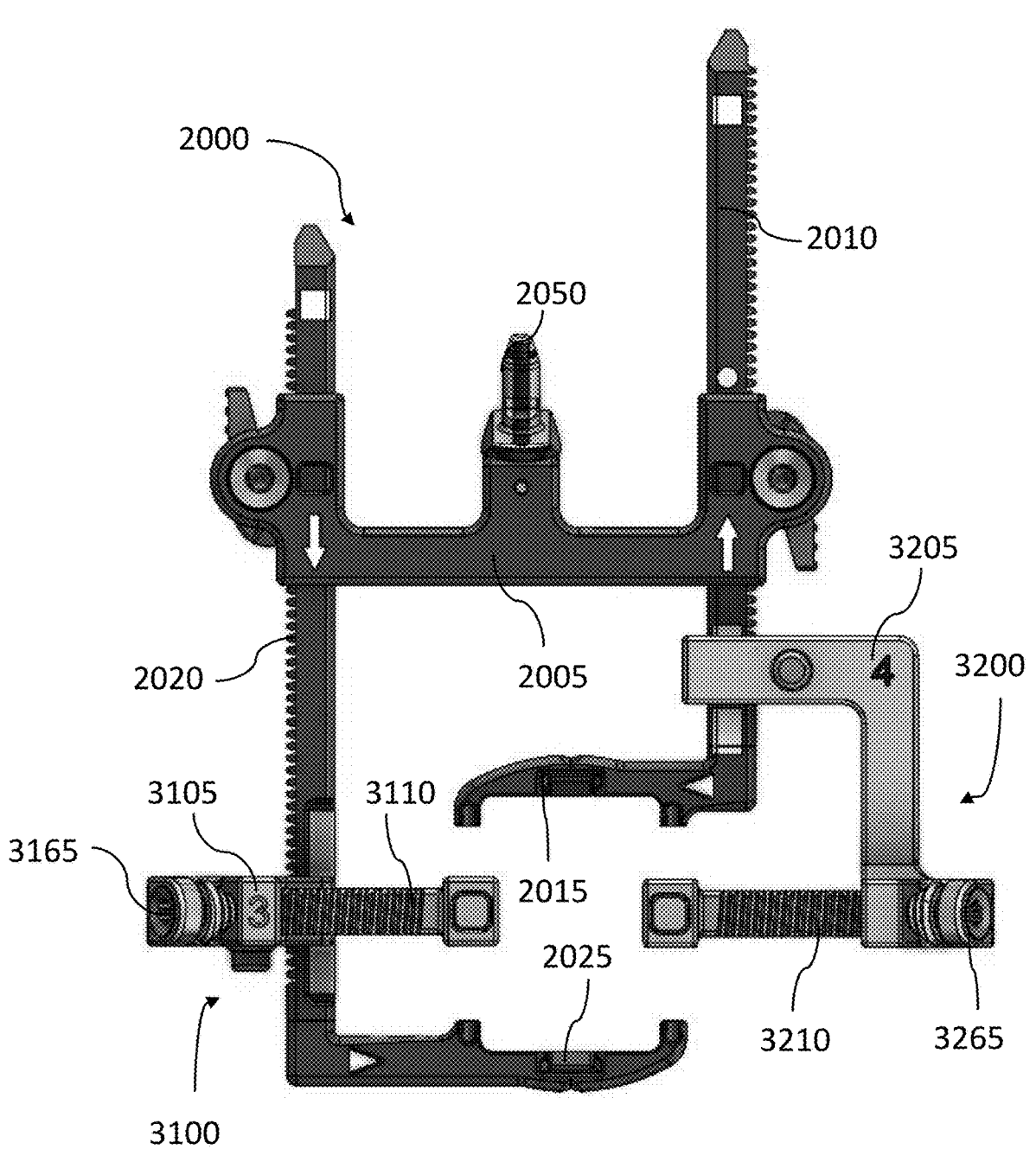

FIGS. 17 to 19 illustrate top views of the surgical retractor 2000 of FIG. 16 as the blades of the surgical retractor are moved and positioned. Specifically, movement of the anterior blade arm 2020 and the posterior blade arm 2010 through the base portion 2005 adjusts the relative anterior/posterior position of the anterior blade 2025 and the posterior blade 2015, respectively. Additionally, movement of components of the modular blade assemblies 3100 and 3200 (e.g., first blade arm 3110 and/or second blade arm 3210) adjusts the relative inward/outward position of the the first auxiliary blade 3115 and the second auxiliary blade 3215 relative to the anterior blade 2025 and the posterior blade 2015, respectively. FIG. 18 shows a view of the first auxiliary blade 3115 and second auxiliary blade 3215 in an outward position and FIG. 19 shows a view with the first auxiliary blade 3115 and second auxiliary blade 3215 in an inward position. The positions can be adjusted according to the needs of the surgeon based on the particular patient's anatomy. The surgical corridor created with the surgical retractor 2000 can have a generally rectangular or square shape; however, it will be appreciated that other shapes of the surgical corridor can be achieved, such as through different shapes of the blades 2015, 2025, 3115, and/or 3215.

The first auxiliary blade 3115 may be positioned substantially orthogonal to the anterior and/or posterior blades 2015, 2025. Similarly, the second auxiliary blade 3215 may be positioned substantially orthogonal to the anterior and/or posterior blades 2015, 2025. The first auxiliary blade 3115 and the second auxiliary blade 3215 may be positioned substantially opposite each other. The first auxiliary blade 3115 and the second auxiliary blade 3215 may be adjustable in length. As discussed more with respect to FIGS. 31 through 34B, the auxiliary blades 3115, 3215 may include a spring-biased distal tip that self-adjusts in length based on contact, or lack thereof, with tissues or patient anatomy.

Figure 20:
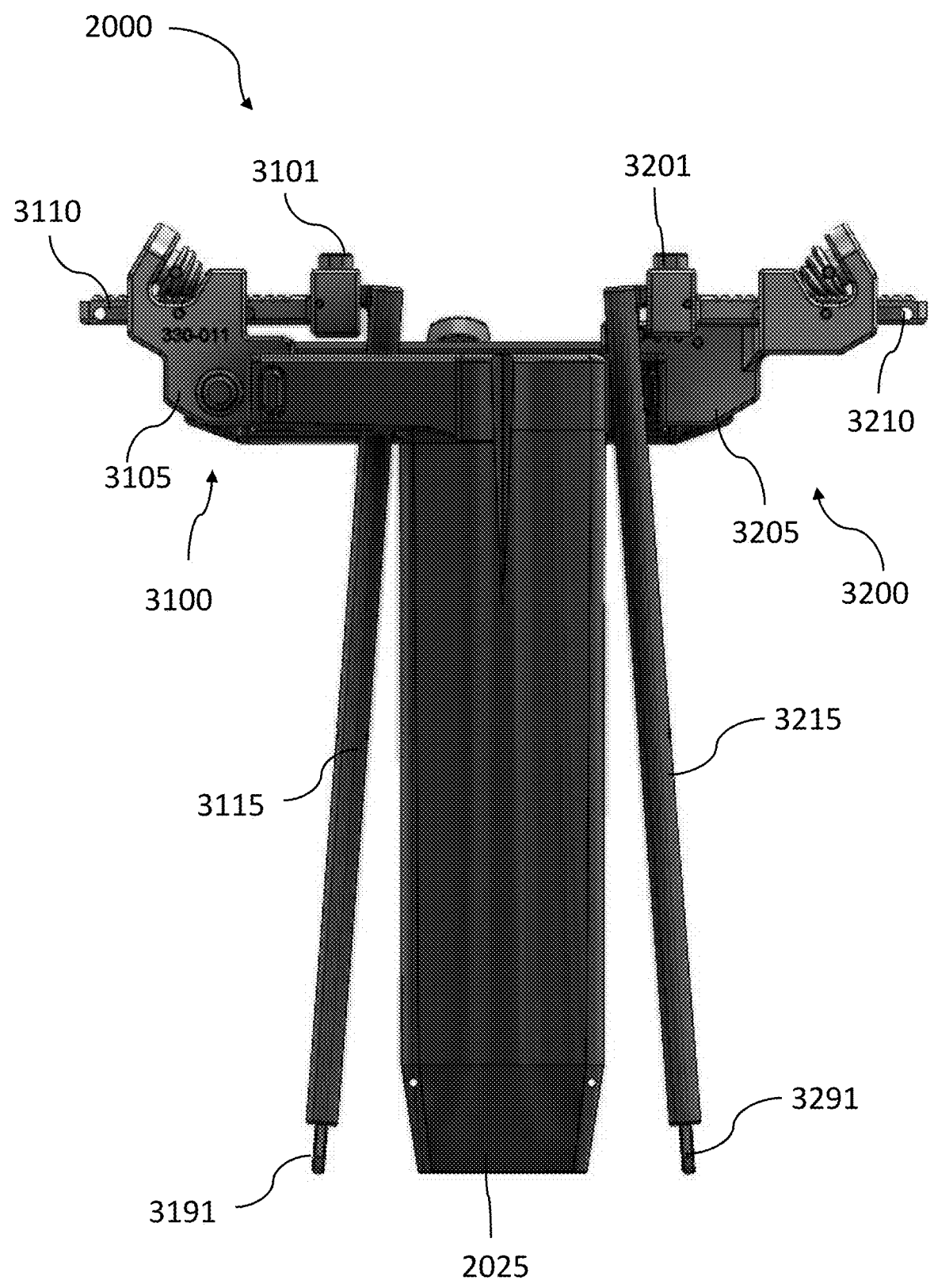
FIG. 20 illustrates an end view of the surgical retractor of FIG. 16 in a first position.
Figure 21:
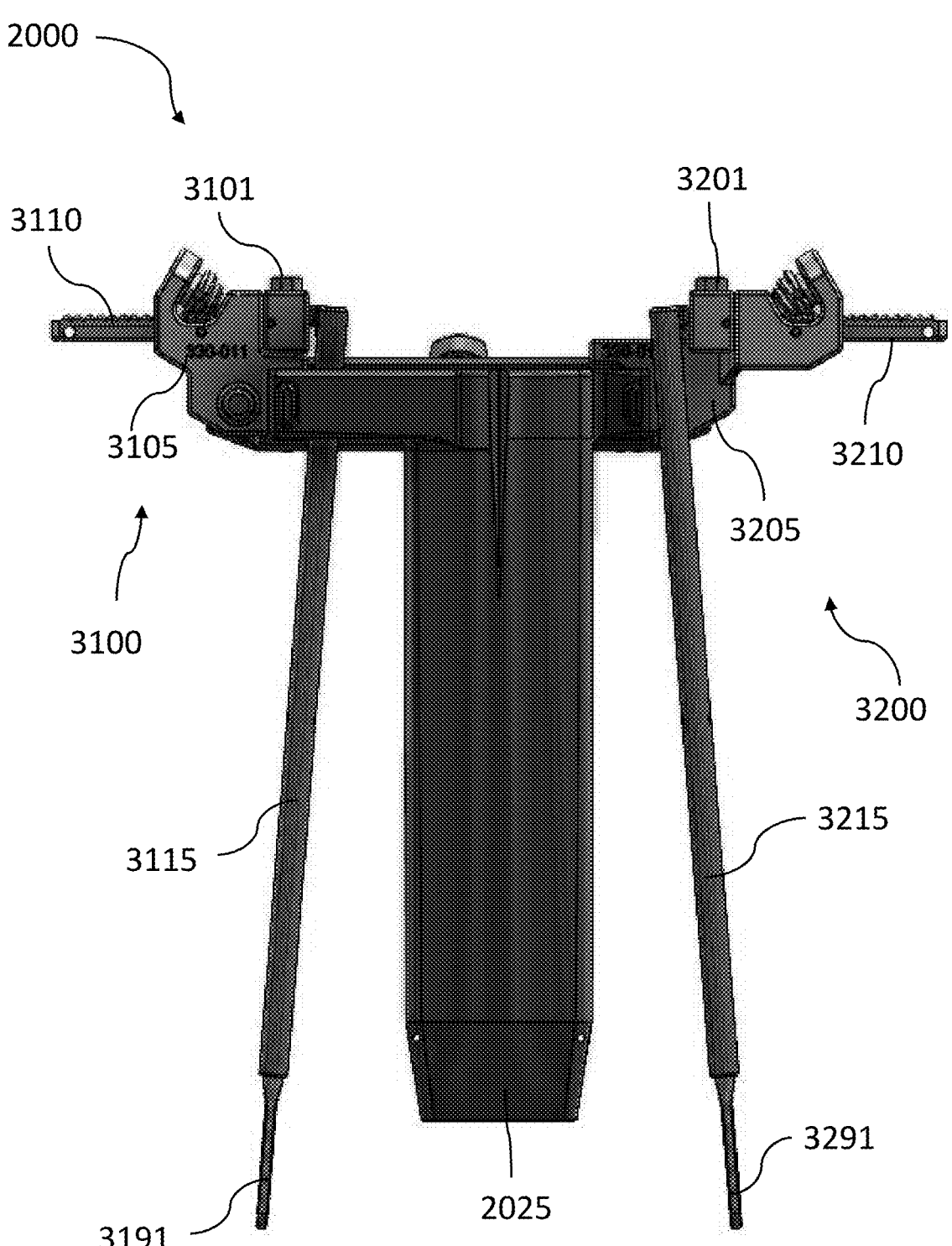
FIG. 21 illustrates an end view of the surgical retractor of FIG. 20 in a second position.

FIGS. 20 and 21 illustrate end views of the surgical retractor 2000 of FIG. 16. As illustrated, both the first auxiliary blade 3115 and the second auxiliary blade 3215 have a toe, angle, or bias relative to (i) each other and (ii) the anterior and/or posterior blades 2015, 2025. The first auxiliary blade 3115 and the second auxiliary blade 3215 may have an outward angle or bias relative to the anterior and/or posterior blades 2015, 2025, respectively. This outward angle or bias may be built-in to the structure of the first auxiliary blade 3115 and/or the second auxiliary blade 3215. The outward angle or bias allows the first auxiliary blade 3115 and/or the second auxiliary blade 3215 to contact tissue or other patient anatomy and to retract the tissue or patient anatomy without bending into the surgical corridor. If the first auxiliary blade 3115 and/or the second auxiliary blade 3215 did not include an outward angle or bias, the first auxiliary blade 3115 and/or the second auxiliary blade 3215 could undesirably bend inwardly and block the surgical corridor when pressed inward by tissues or patient anatomy.

Figure 22:
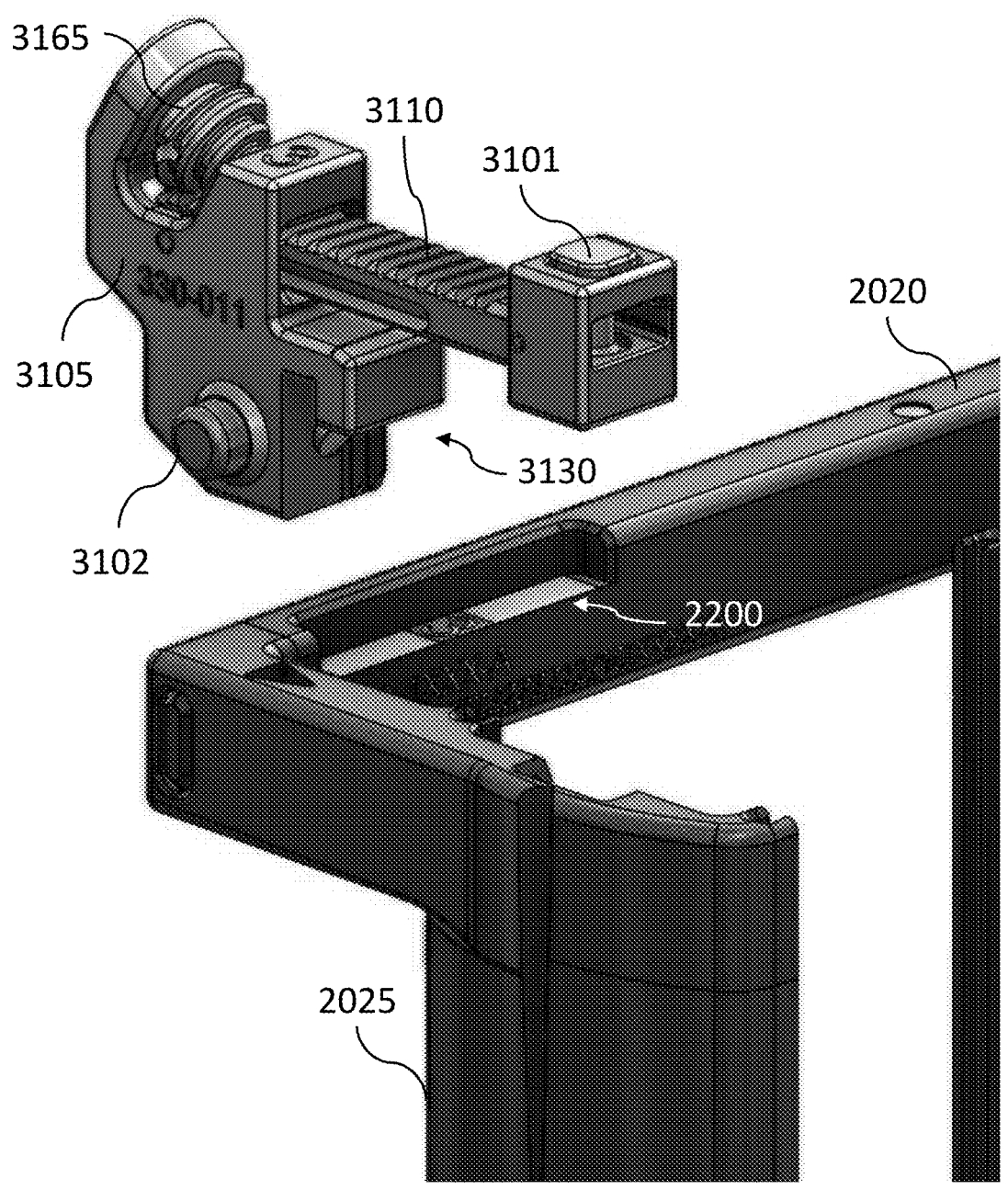
FIG. 22 illustrates a partial exploded view of an anterior base portion and an anterior arm from the surgical retractor of FIG. 16.
Figure 23:
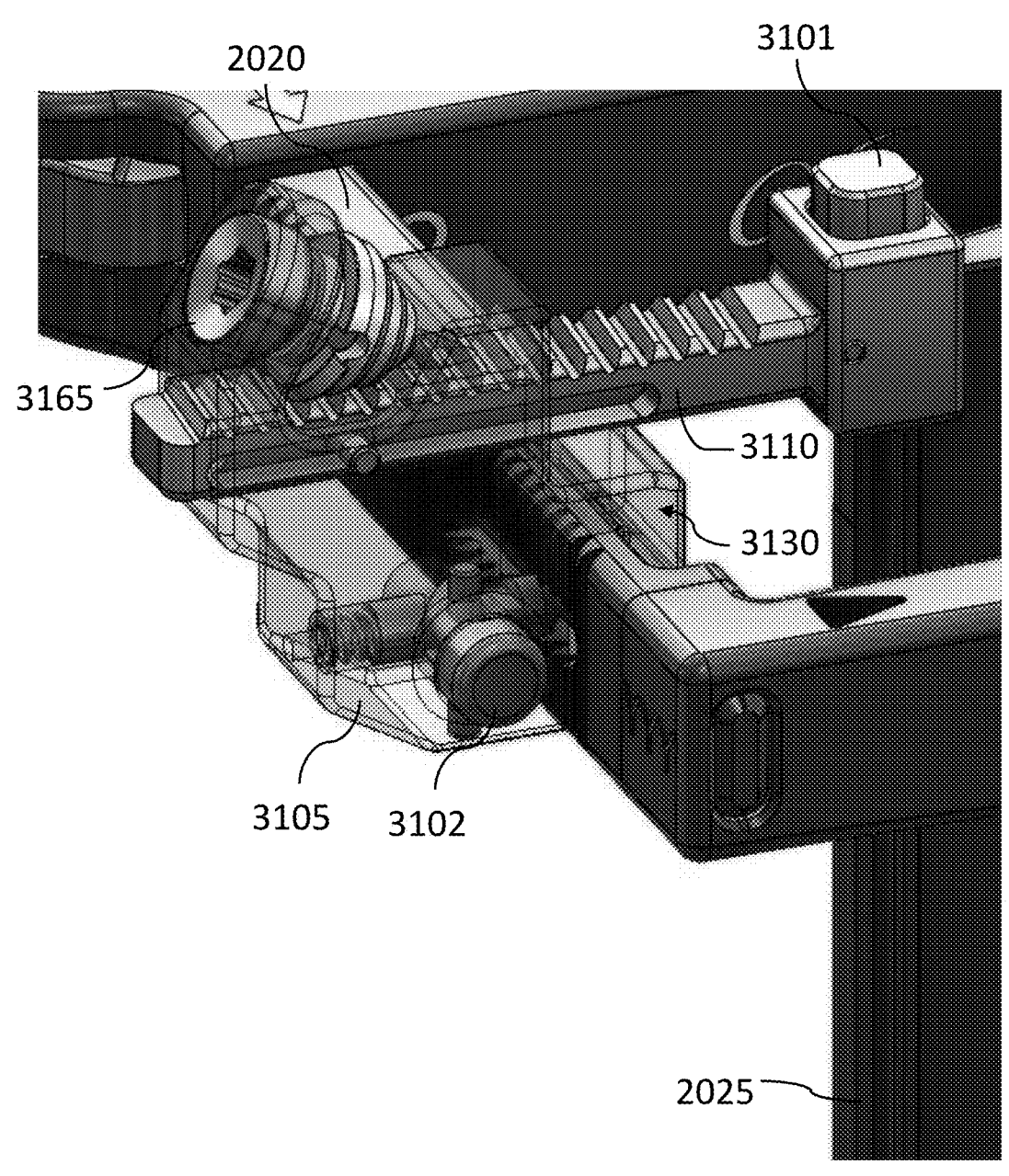
FIG. 23 illustrates the anterior base portion and the anterior arm of FIG. 22 in a connected configuration.

FIG. 22 illustrates a partial exploded view of the anterior base portion 3105 and the anterior arm 2020 and FIG. 23 illustrates the anterior base portion 3105 and the anterior arm 2020 in a connected configuration. Though FIGS. 22 and 23 are discussed relative to anterior arm 2020, it is to be understood that the discussion similarly applies to posterior arm 2010 and posterior base portion 3205. The anterior base portion 3105 may include a hooked portion 3130 for connecting the anterior base portion 3105 to the anterior arm 2020. Specifically, the hooked portion 3130 mechanically engages the anterior arm 2020, such that a surface (e.g., a bottom surface) of the anterior base portion 3105 abuts or otherwise rests on a top surface of the anterior arm 2020. The anterior arm 2020 includes or defines a slot 2200 for receiving and engaging the hooked portion 3130 of the anterior base portion 3105. The blade arm 3110 is movable within the anterior base portion 3105 through adjustment mechanism 3165, which may be a worm wheel, a gear, a pawl, or another appropriate mechanism to engage the blade arm 3110. Importantly, when the anterior base portion 3105 is secured to the anterior arm 2020, the blade arm 3110 is capable of movement within the anterior base portion 3105 and into the surgical corridor. The anterior base portion 3105 can also include a release mechanism 3102 (e.g., a button, switch, toggle, slide, etc.) to release the anterior base portion 3105 from the anterior arm 2020.

Figure 24A:
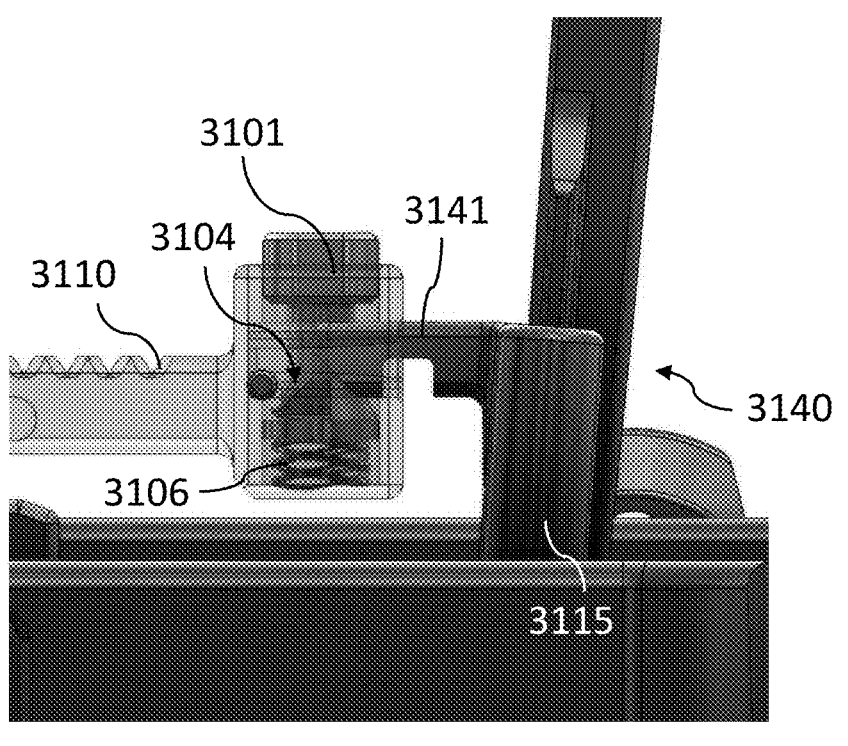
FIGS. 24A and 24B illustrate close-up, transparent views of a portion of an auxiliary blade connected to either the anterior base portion of FIGS. 22 and 23, or a posterior base portion.
Figure 24B:
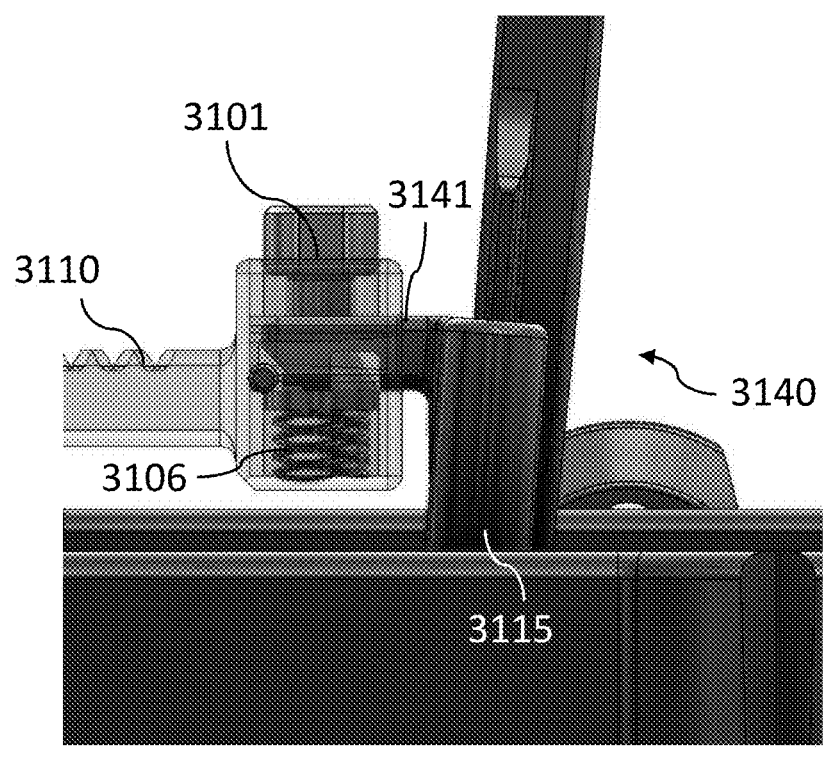

The auxiliary blades 3115 and 3215 can be connected to the anterior or posterior base portions in any suitable manner. FIGS. 24A and 24B illustrate close-up, transparent views of a portion of an auxiliary blade 3115 connected to either the anterior base portion 3105 of FIGS. 22 and 23, or a posterior base portion 3205. Though FIGS. 24A and 24B are discussed relative to auxiliary blade 3115, it is to be understood that the discussion similarly applies to auxiliary blade 3215. That is, the described connection of FIGS. 24A and 24B is applicable to both the first auxiliary blade 3115 with the anterior base portion 3105, and the second auxiliary blade 3215 and the posterior base portion 3205. In the embodiment illustrated, a proximal end 3140 of the auxiliary blade 3115 includes a projection or latch 3141 to allow the auxiliary blade 3115 to be connected to the anterior base portion 3105.

The latch 3141 is for mating and mechanically engaging a release mechanism 3101 on the blade arm 3110. The latch 3141 mates with a notch or cut-out 3104 of the release mechanism 3101, thereby engaging the release mechanism 3101 (see FIG. 24B). The latch 3141 extends into a portion of the blade arm 3110 (discussed with respect to FIGS. 25 to 27). As the latch 3141 extends into the blade arm 3110, the latch 3141 will cause the release mechanism 3101 to depress or compress a spring 3106 contained within the blade arm 3110. When the latch 3141 engages the cut-out 3104 of the release mechanism 3101, the spring will expand, causing the latch 3141 to be secured against the release mechanism 3101 through the cut-out 3104. To release the auxiliary blade 3115 from the blade arm 3110, the release mechanism 3101 can be depressed, causing the spring 3106 to compress and the latch 3141 to disengage the cut-out 3104, and the auxiliary blade 3115 can be removed. Other mechanisms can also be used to attach the auxiliary blades to the blade arm of the anterior or posterior base portions. Or in other embodiments, the auxiliary blades could be integral to the blade arm.

Figure 25:
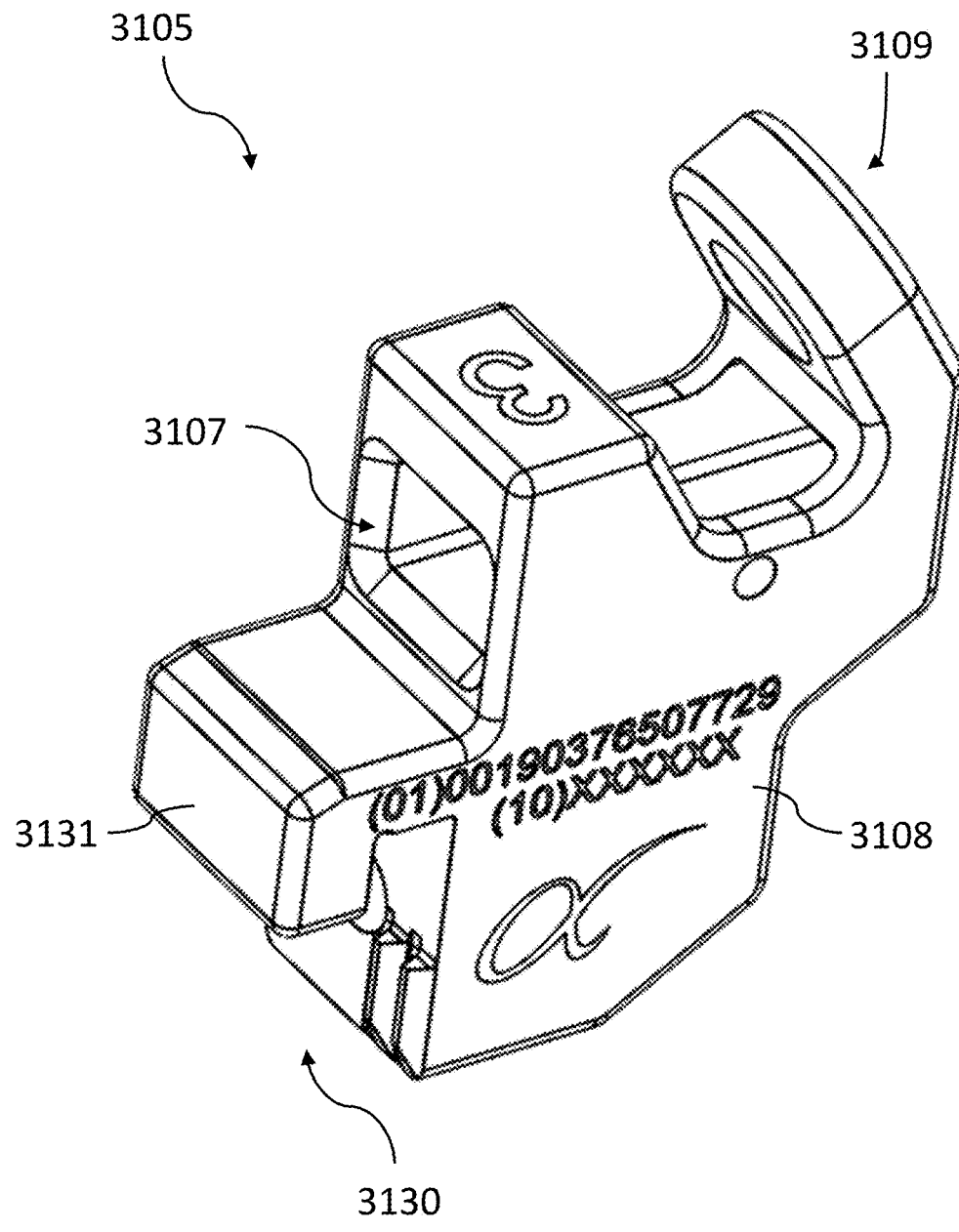
FIG. 25 illustrates a perspective view of the anterior base portion of FIGS. 22 to 24B.
Figure 26:
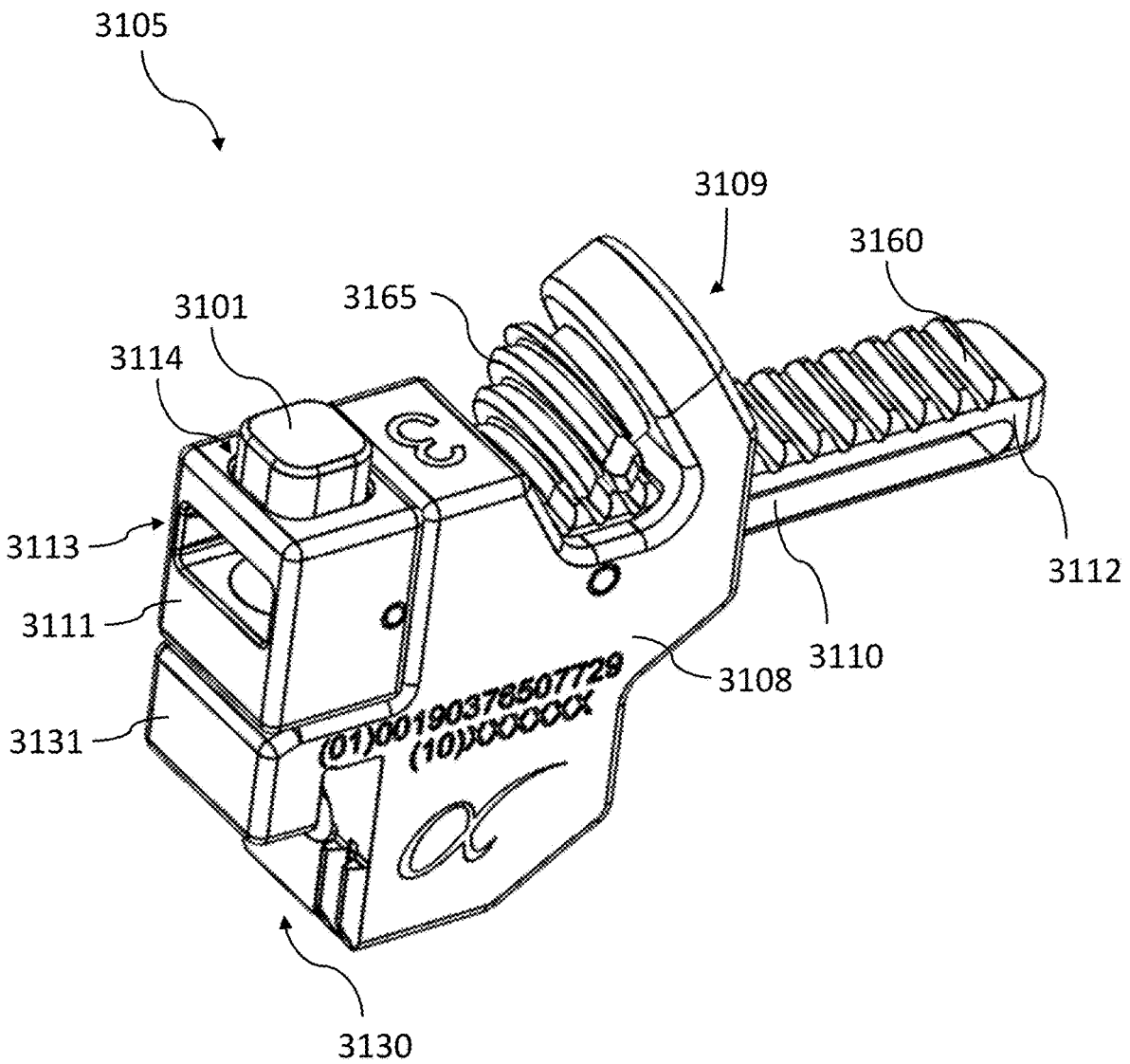
FIG. 26 illustrates a perspective view of the anterior base portion of FIGS. 22 to 25 having received a portion of a blade arm.
Figure 27:
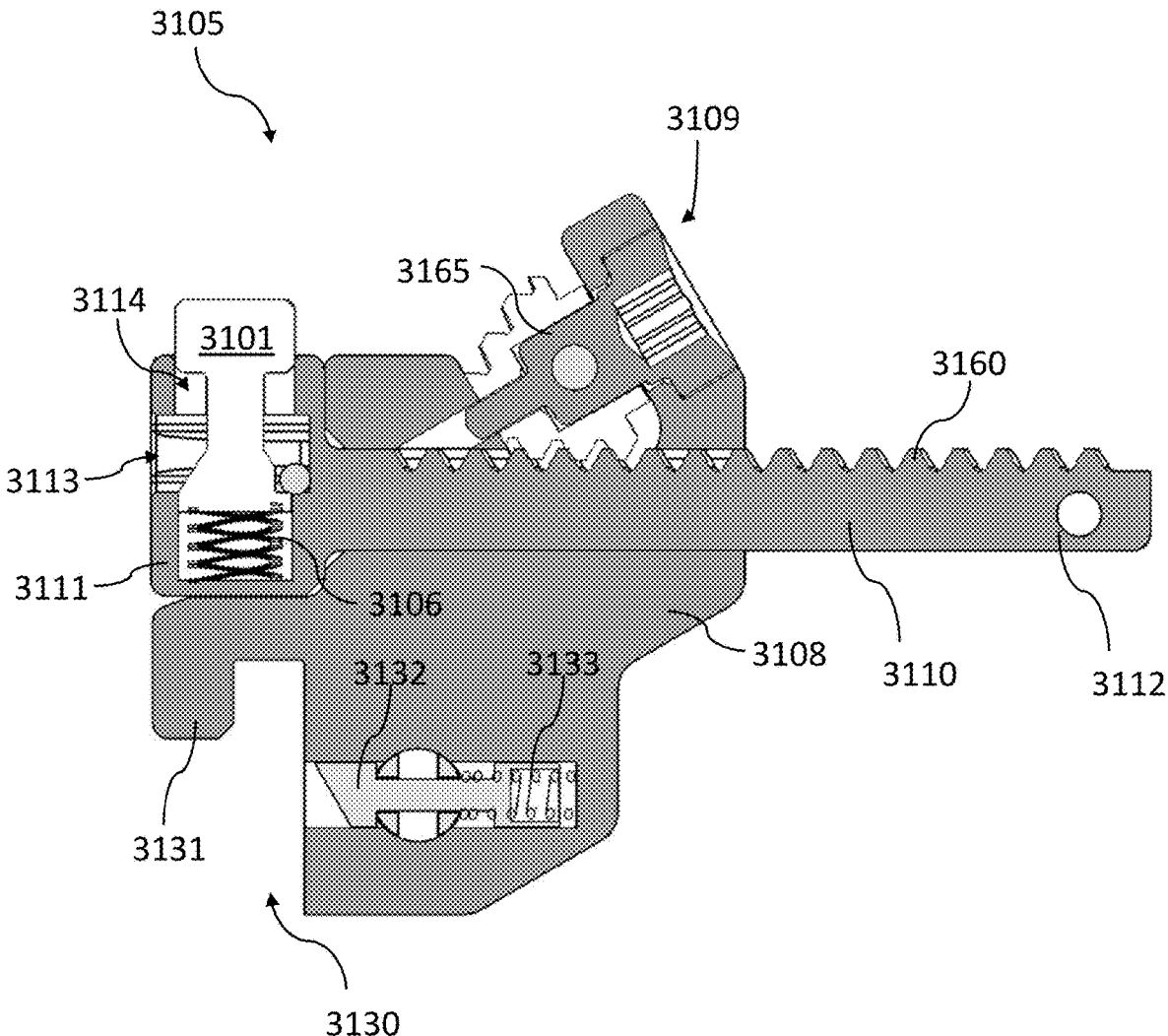
FIG. 27 illustrates a cross-sectional view of FIG. 26.

FIG. 25 illustrates a perspective view of the anterior base portion 3105 without the blade arm 3110, and FIG. 26 illustrates a perspective view of the anterior base portion 3105 with the blade arm 3110. FIG. 27 illustrates a cross-sectional view of FIG. 26. The anterior base portion 3105 includes a body 3108, which may be substantially rectangular or square with various projections or extensions. For example, the body 3108 includes a hooked portion 3130. The hooked portion 3130 includes a hook 3131 extending away from the body 3108 and for engaging the anterior arm 2020 of the surgical retractor 2000.

The hooked portion 3130 also includes a latch 3132 and a spring 3133. Spring 3133 biases the latch 3132 outwardly (FIG. 27 shows an inward position). When the hooked portion 3130 is positioned over the slot 2200 of the anterior arm 2020, the latch 3132 is pushed into the body 3108 of the anterior base portion 3105, thereby compressing the spring 3133. When the hooked portion 3130 is secured with the slot 2200 of the anterior arm 2020, the spring 3133 biases the latch outwardly, causing the latch 3132 to abut the anterior arm 2020, thereby mechanically securing the anterior base portion 3105 to the anterior arm 2020. The anterior base portion includes a release mechanism 3102 (see FIG. 22) to release the anterior base portion 3105 from the anterior arm 2020 of the retractor 2000.

The body 3108 also defines a channel 3107 for receiving the blade arm 3110 (see FIGS. 26 and 27) and a void 3109 for receiving the adjustment mechanism 3165. The void 3109 is positioned so the adjustment mechanism 3165 extends through the void 3109 and partially into the channel 3107 to engage and adjust a position of the blade arm 3110. For example, the blade arm 3110 may include a plurality of teeth 3160 and the adjustment mechanism 3165 may be a worm gear or other gear configured to engage the plurality of teeth 3160. Rotation of the adjustment mechanism 3165 in a first direction causes the blade arm 3110 to be advanced through the anterior base portion 3105 towards the surgical corridor, thereby narrowing the surgical corridor. Rotation of the adjustment mechanism 3165 in a second direction causes the blade arm 3110 to be retracted through the anterior base portion 3105 away the surgical corridor, thereby enlarging the surgical corridor.

The blade arm 3100 includes a first end 3111 and a second end 3112 opposite the first end 3111. The first end 3111 defines a first cavity 3113 to receive the latch 3141 at the proximal end 3140 of the auxiliary blade 3115. The first end 3111 also defines a second cavity 3114 to receive the release mechanism 3101 and house the spring 3106. The first cavity 3113 and the second cavity 3114 may be in communication with each other, such that the latch 3141 of the auxiliary blade 3115 may contact and engage the release mechanism 3101.

Figure 28:
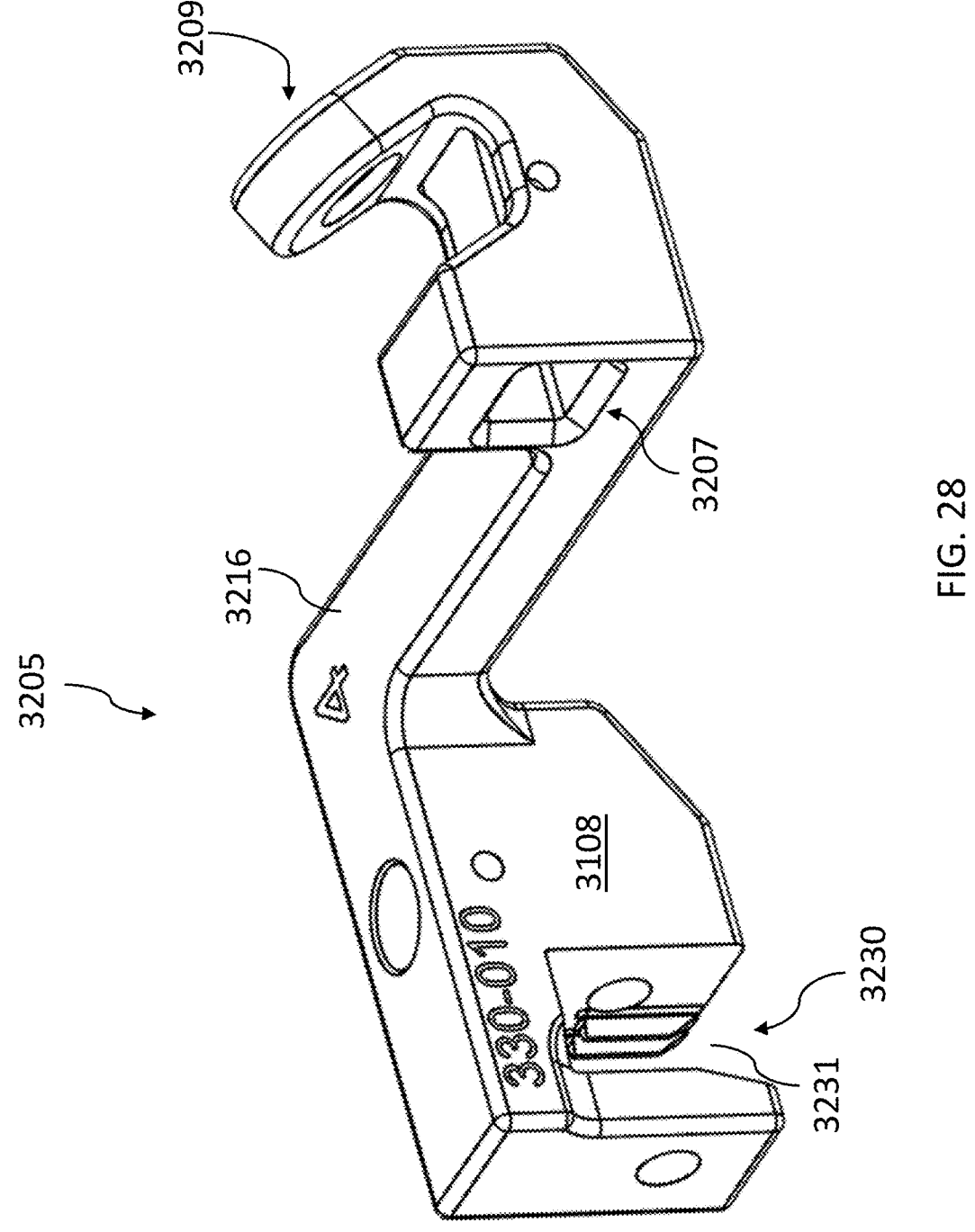
FIG. 28 illustrates a perspective view of a posterior base portion for use with the surgical retractor of FIGS. 16 through 24B.
Figure 29:
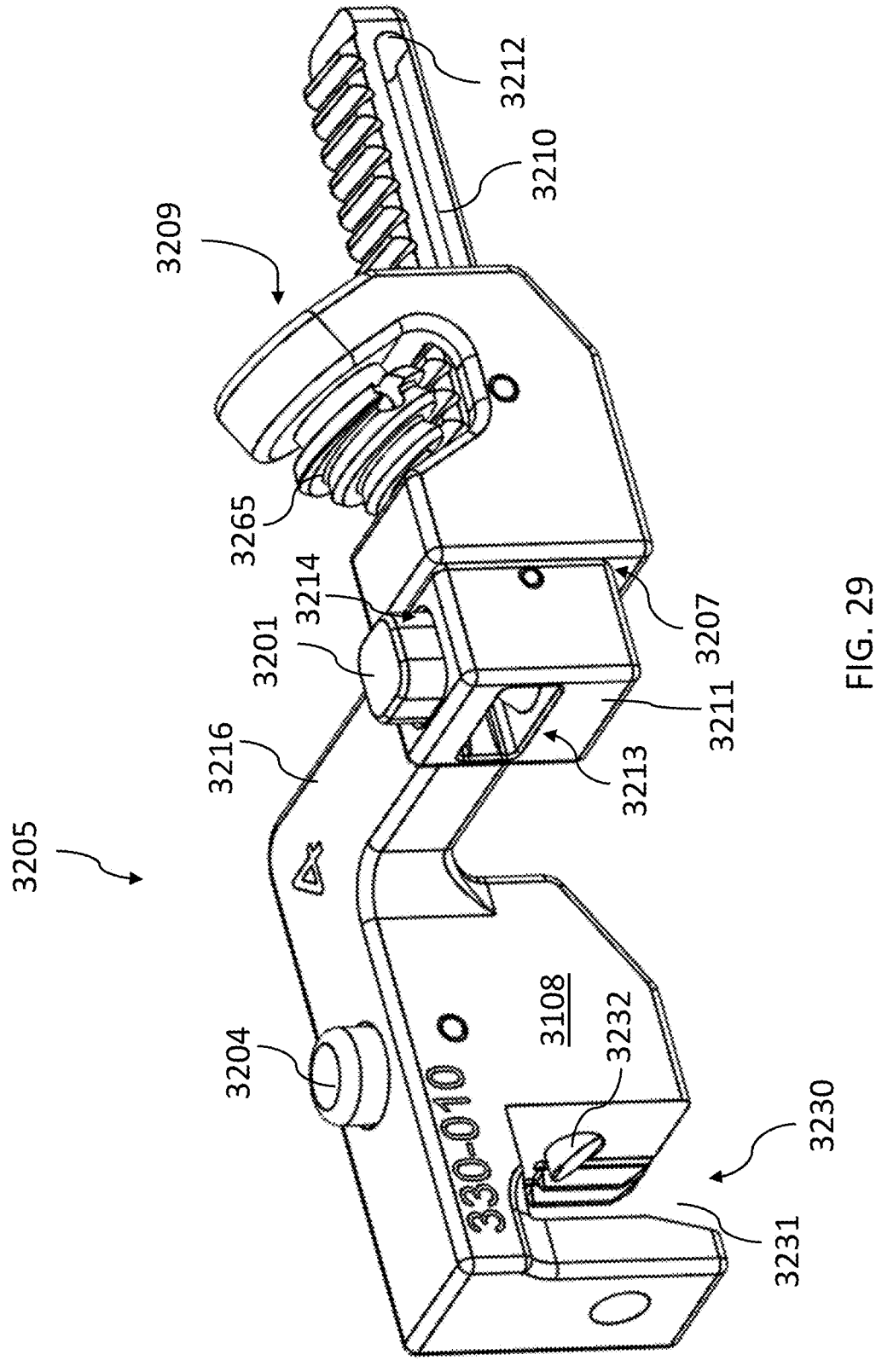
FIG. 29 illustrates a perspective view of the posterior base portion of FIG. 28 having received a portion of a blade arm.
Figure 30:
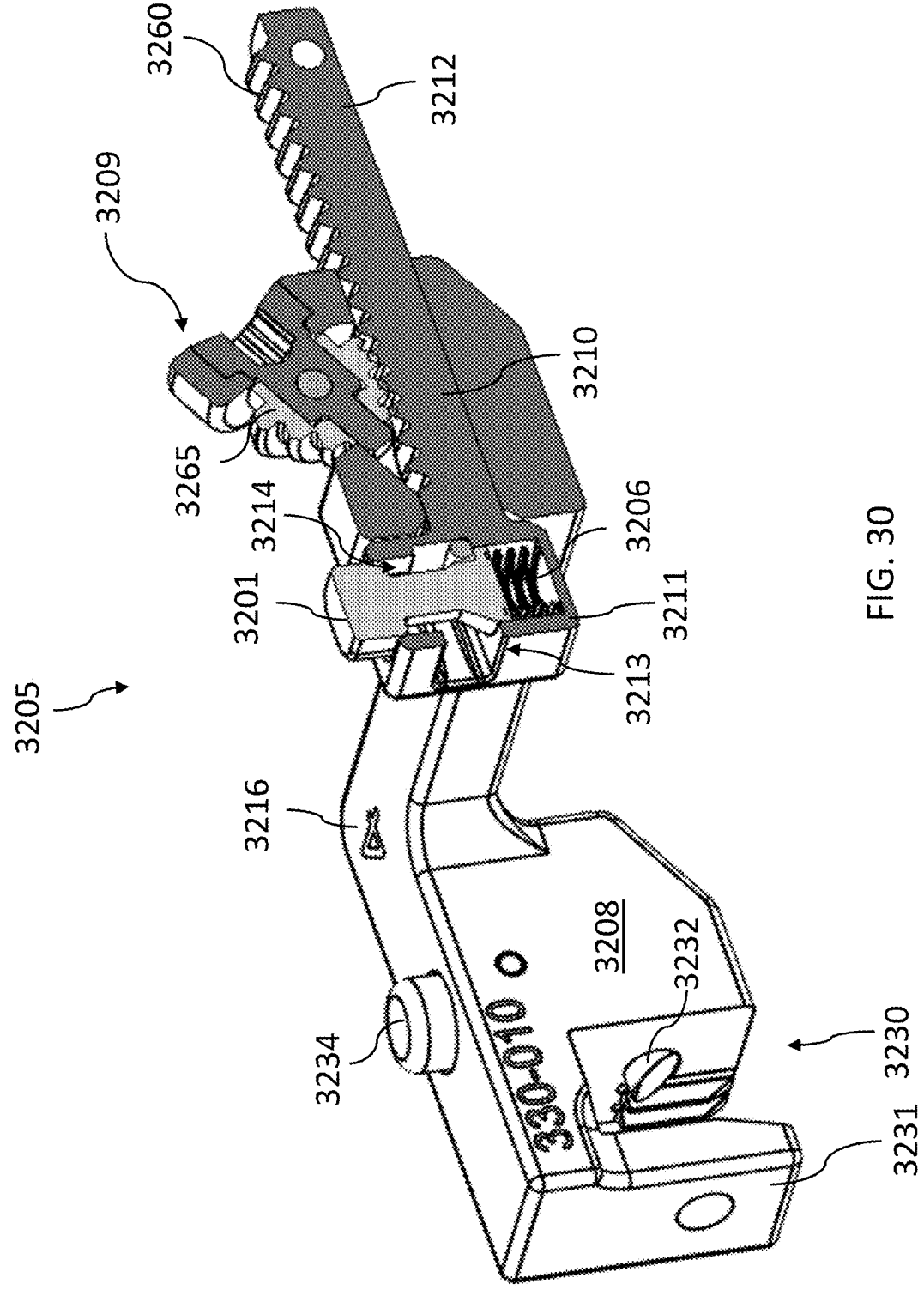
FIG. 30 illustrates a cross-sectional view of FIG. 29.

FIG. 28 illustrates a perspective view of a posterior base portion 3205 (without blade arm 3210) and FIG. 29 illustrates a perspective view with the blade arm 3210. FIG. 30 illustrates a cross-sectional view of FIG. 29. The posterior base portion 3205 includes a body 3208, which may be rectangular or square with various projections or extensions. For example, the body 3208 includes an arm engagement portion 3230. The arm engagement portion 3230 includes a groove or indentation for receiving/engaging the posterior arm 2010 of the surgical retractor 2000. The arm engagement portion 3230 also includes a latch 3232 and a spring 3233. When the arm engagement portion 3230 is positioned over the posterior arm 2010, the latch 3232 is pushed into the body 3208 of the posterior base portion 3205, thereby compressing the spring 3233. When the arm engagement portion 3230 is secured over the posterior arm 2010, the spring 3233 expands, causing the latch 3232 to abut a posterior arm 2010, thereby mechanically securing the posterior base portion 3205 to the posterior arm 2010. The posterior base portion 3205 includes a release mechanism 3202 to release the posterior base portion 3205 from the posterior arm 2010 of the retractor 2000.

The body 3208 also includes an extension 3216, which may provide the posterior base portion 3205 with an overall L-shape. The extension 3216 allows the posterior base portion 3205 to position an auxiliary blade 3215 anterior relative to the posterior blade 2015. That is, the extension 3216 extends anteriorly past the posterior blade 2015 and positions the auxiliary blade 3215 anterior relative to the posterior blade 2015. This allows the auxiliary blade 3215 to be substantially parallel to the auxiliary blade 3115 and create a rectangular surgical corridor.

The body 3208 also defines a channel 3207 for receiving the blade arm 3210 (sec FIGS. 29 and 30) and a port 3209 for receiving the adjustment mechanism 3265. The port 3209 is positioned such that the adjustment mechanism 3265 extends through the port 3209 and partially into the channel 3207 to engage and adjust a position of the blade arm 3210. For example, the blade arm 3210 may include a plurality of teeth 3260 and the adjustment mechanism 3265 may be a worm gear or other gear configured to engage the plurality of teeth 3260. Rotation of the adjustment mechanism 3265 in a first direction causes the blade arm 3210 to be advanced through the posterior base portion 3205 towards the surgical corridor, thereby narrowing the surgical corridor. Rotation of the adjustment mechanism 3265 in a second direction causes the blade arm 3210 to be retracted through the posterior base portion 3205 away the surgical corridor, thereby enlarging the surgical corridor.

As with the blade arm 3110, the blade arm 3210 includes a first end 3211 and a second end 3212 opposite the first end 3211. The first end 3211 defines a first cavity 3213 to receive the latch 3241 at the proximal end 3240 of the auxiliary blade 3215. The first end 3211 also defines a second cavity 3214 to receive the release mechanism 3201 and house the spring 3206. The first cavity 3213 and the second cavity 3214 may be in communication with each other, such that the latch 3241 of the auxiliary blade 3215 may contact and engage the release mechanism 3201.

Figure 31:
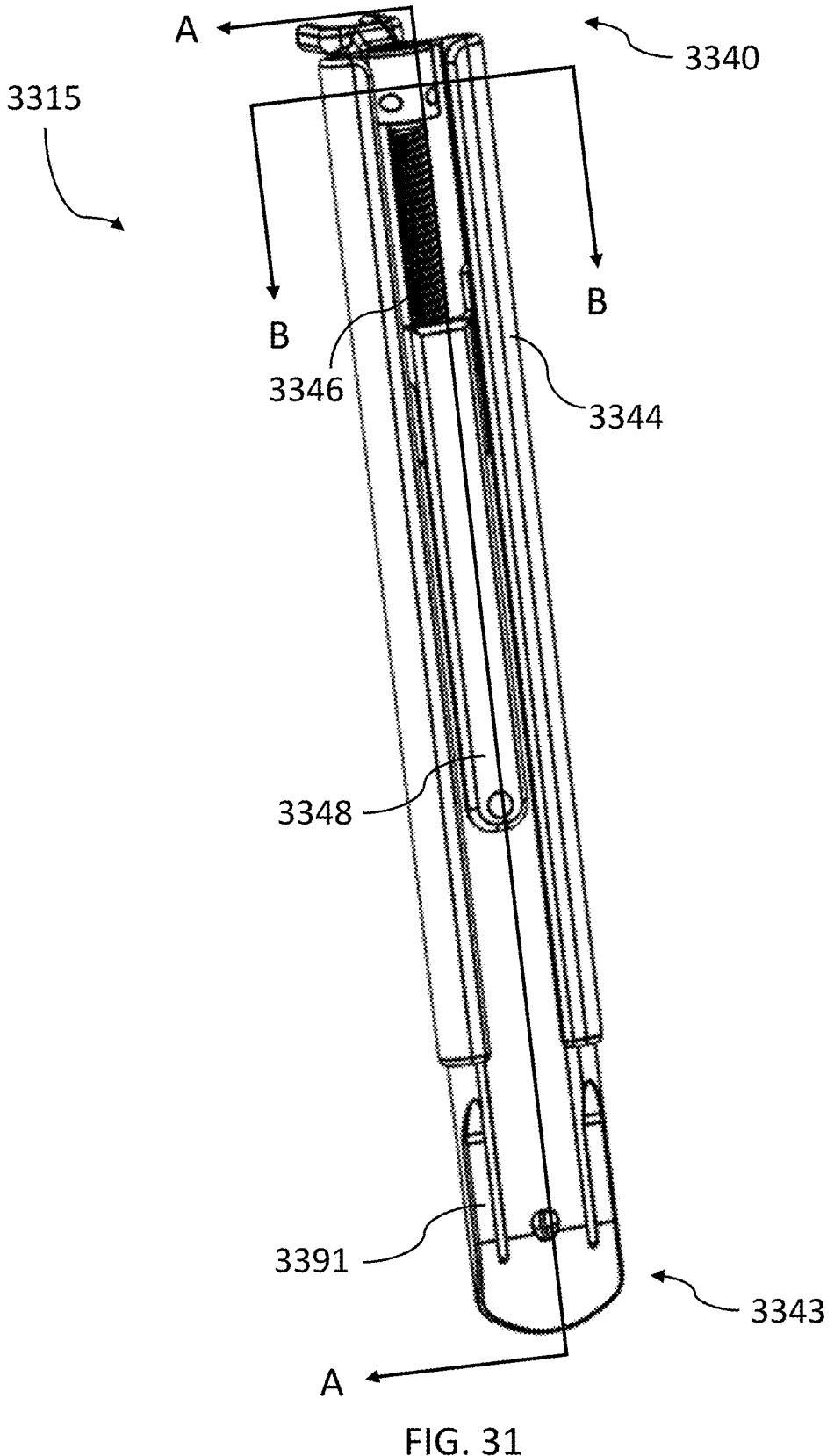
FIG. 31 illustrates another embodiment of an auxiliary blade to be used with the surgical retractor of FIGS. 16 through 24B.
Figures 32A, 32B:
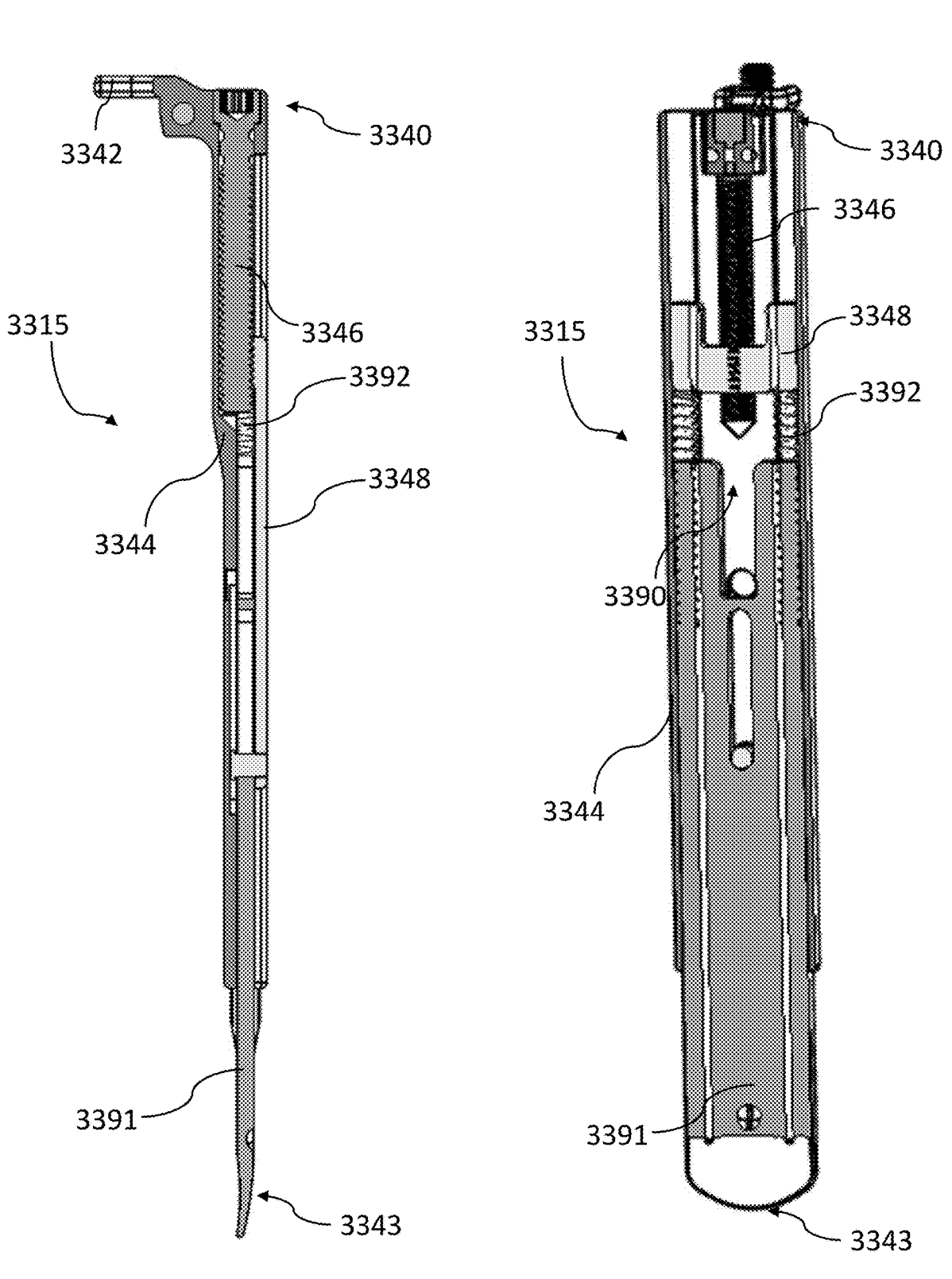
FIG. 32A illustrates a cross-sectional view of the auxiliary blade of FIG. 31 taken through the line A-A and FIG. 32B illustrates a cross-sectional view of the auxiliary blade of FIG. 31 taken through the line B-B.
Figures 33A, 33B:
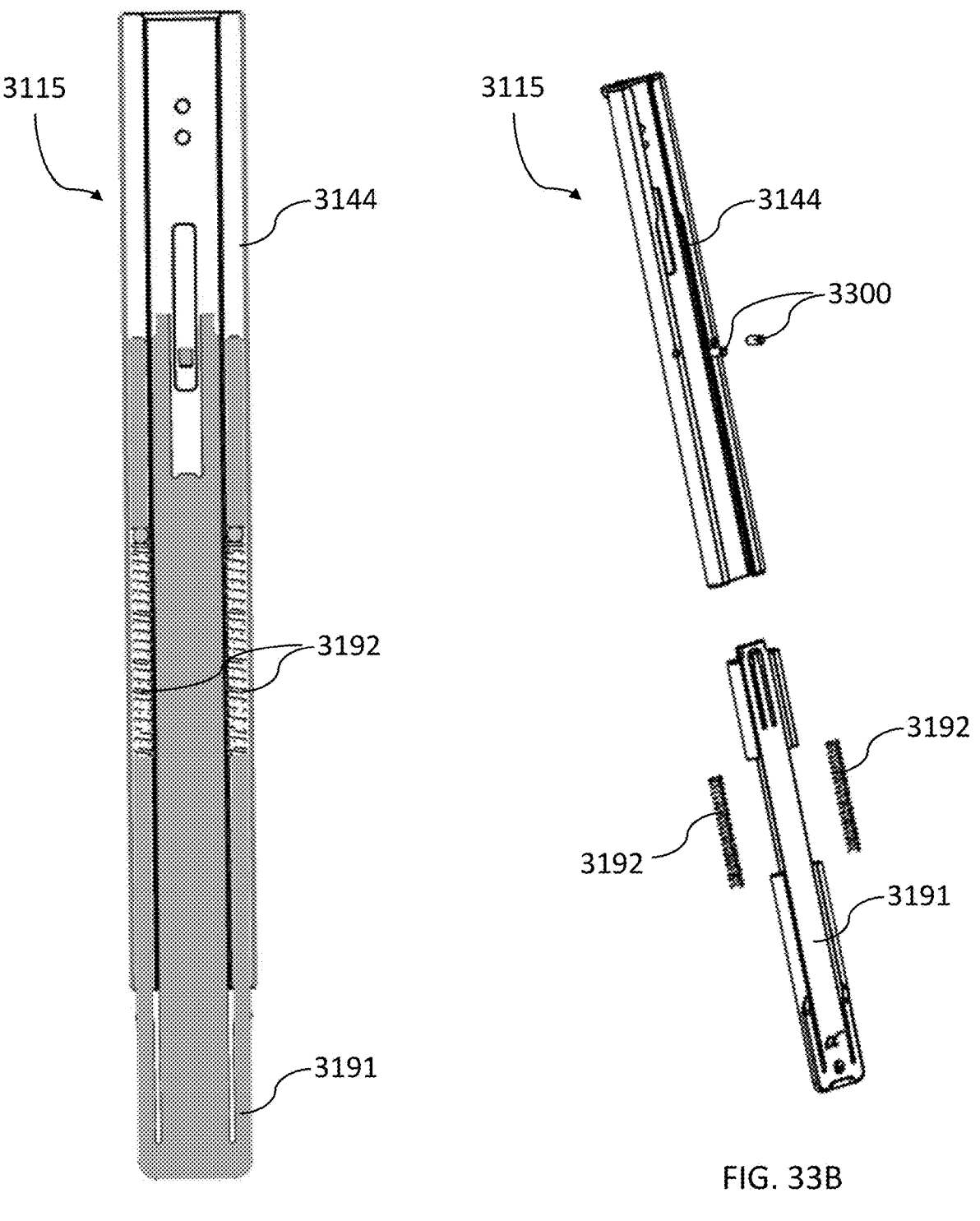
FIG. 33A illustrates a cross-sectional view of another embodiment of an auxiliary blade to be used with the surgical retractors of FIGS. 16 through 24B.
FIG. 33B illustrates a partially exploded view of the auxiliary blade of FIG. 33A.

FIGS. 31 through 32B illustrate various views of another embodiment of an auxiliary blade 3315, 3415 to be used with the surgical retractor 2000 of FIGS. 16 through 24B. Though FIG. 31 will be discussed with respect to first auxiliary blade 3315, it is to be understood that in this embodiment, the second auxiliary blade 3415 is substantially identical to the first auxiliary blade 3315, such that the discussion of the first auxiliary blade 3315 applies to the second auxiliary blade 3415. As illustrated, the auxiliary blade 3315 includes a sheath 3344, an actuator 3346 in connection with a proximal end 3340 of the auxiliary blade 3315, a lead 3348 in connection with the actuator 3346 and the sheath 3344, and a blade tip or shim 3391. The auxiliary blade 3315 extends from the proximal end 3340 to the distal end 3343, where the distal end 3343 may correspond to a distal end of the blade tip 3391. In some embodiments, the actuator 3346 may be manually adjusted to adjust the depth of the blade tip 3391 relative to the sheath 3344. For example, rotation or other manual adjustment of the actuator 3346 in a first direction may cause the blade tip 3391 to be adjusted distally relative to the sheath 3344. Similarly, rotation or other manual adjustment of the actuator 3346 in a second direction may cause the blade tip 3391 to be adjusted proximally relative to the sheath 3344.

Referring to FIGS. 32A and 32B, the auxiliary blade 3315 also includes at least one spring 3392. The sheath 3344 may include or define a central channel 3390 for receiving the actuator 3346, the lead 3348, the spring 3392, and at least a portion of the blade tip 3391. The central channel 3390 may allow the various components of the auxiliary blade 3315 to slide and adjust within the sheath 3344. The spring 3392 may be positioned between a proximal end of the lead 3348 and a proximal end of the blade tip 3391. The spring 3392 may bias the blade tip 3391 in a first position relative to the sheath 3344. Upon contact of the blade tip 3391 with tissue or patient anatomy, the spring 3392 may contract or compress, causing the blade tip 3391 to slide within the sheath 3344, thereby shortening a length of the auxiliary blade 3315. The spring 3392 may include two (2) springs 3392 positioned substantially symmetrically between the blade tip 3391, the lead 3348, and/or the sheath 3344.

Referring to FIGS. 33A through 34B, which illustrate the auxiliary blade 3115, 3215 of FIGS. 16-21 and FIGS. 24A-24B, the auxiliary blade 3115 may include the sheath 3144, the blade tip 3191, and springs 3192, with no bridge or lead 3148 and no actuator 3346. In this embodiment, the springs 3192 still bias the blade tip 3191 in a first position relative to the sheath 3144. Pins 3300 may secure the springs 3192 between the blade tip 3191 and the sheath 3144, facilitating in biasing the blade tip 3191 in the first position. For example, the springs 3192 may bias the blade tip 3191 in an extended position, such as illustrated in FIG. 34A.

Upon contact with tissue or patient anatomy, the spring 3192 may contract or compress, causing the blade tip 3191 to slide proximally within the sheath 3144, thereby shortening a length of the auxiliary blade 3115, as shown in FIG. 34B. The length of the auxiliary blade 3115 may range from about 100 mm to about 200 mm, such as 120, 140, 150, 160, 170, 180 mm, or a length within a range defined by any two of the foregoing values. The length of the auxiliary blade 3115 may be adjusted through extension of the blade tip 3191.

Figure 35:
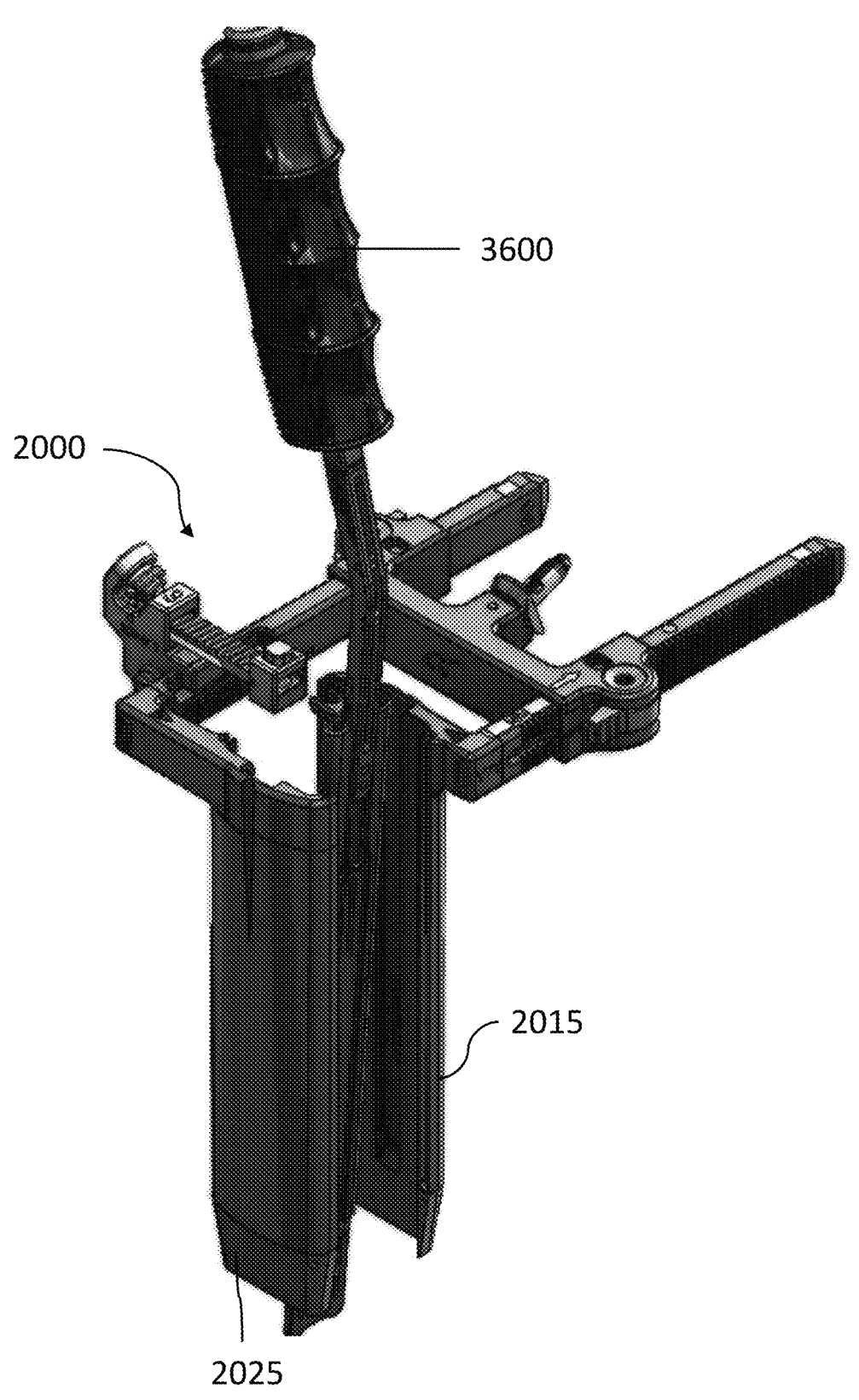
FIG. 35 illustrates the surgical retractor of FIG. 16 and a blade handle connected to an auxiliary blade.

FIG. 35 illustrates the surgical retractor 2000 of FIG. 16 and a handle 3600. The handle 3600 may engage either modular blade assembly 3100, 3200. For example, the handle 3600 may be utilized to secure a first auxiliary blade 3115 to the anterior base portion 3105 of the modular blade assembly 3100. The anterior and/or posterior base portions 3105, 3205 may include adjustment mechanisms (e.g., buttons, switches, knobs, palls, etc.) that can adjust an angle of the auxiliary blades 3115, 3215 in at least two planes, where the at least two planes are orthogonal to each other. For example, an angle of the auxiliary blades 3115, 3215 may be adjusted into and/or out of the surgical corridor. Additionally, the anterior and/or posterior base portions 3105, 3205 may include adjustment mechanisms that can adjust an angle of the auxiliary blades 3115, 3215 in a plane orthogonal to the anterior and posterior blades 2015, 2025 (e.g., forward/backward along a plane of the surgical corridor created by the auxiliary blades 3115, 3215).

Figure 36:
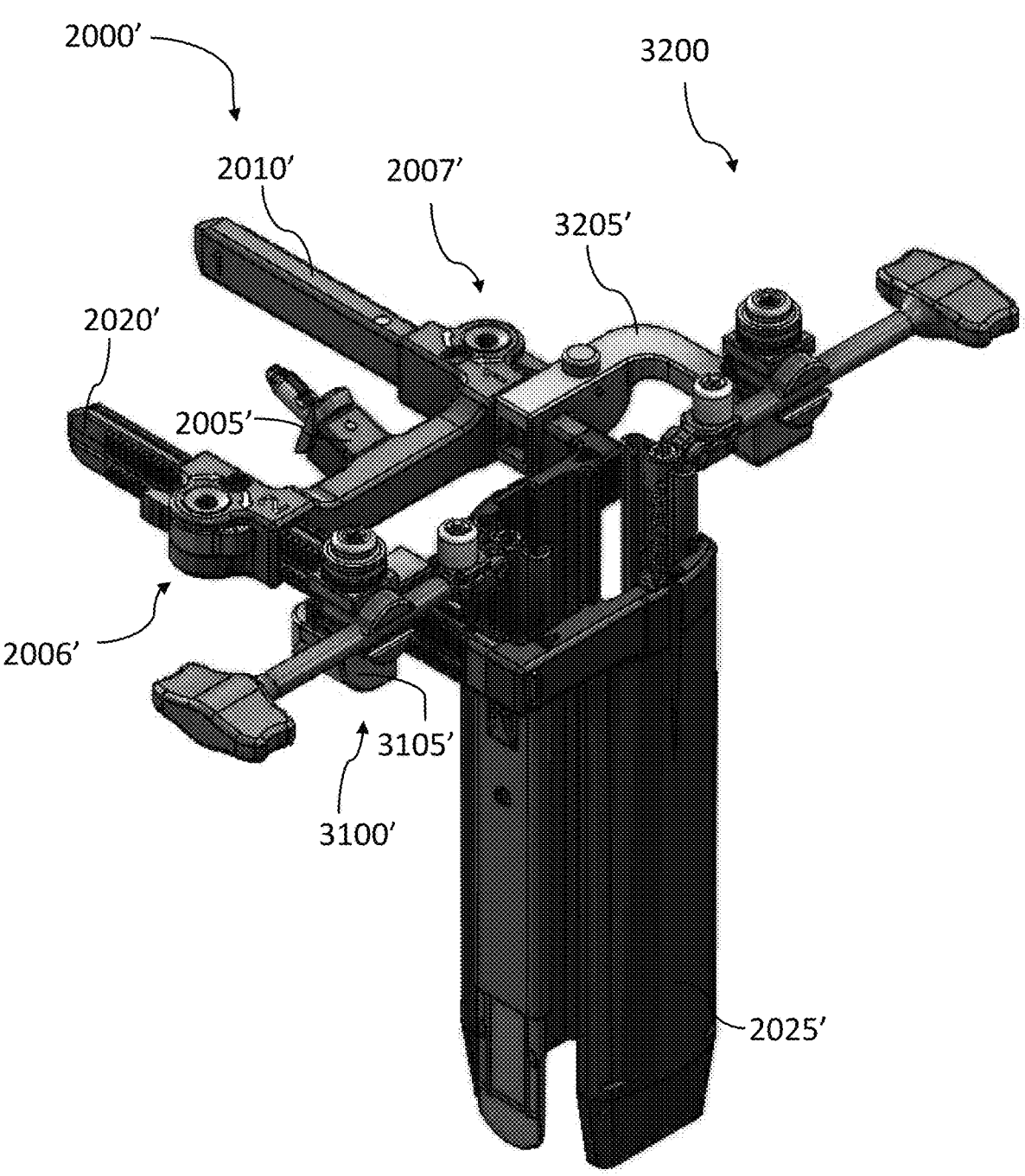
FIG. 36 illustrates a top, perspective view of another embodiment of a surgical retractor according to the present disclosure that includes two auxiliary retractor blades.

FIG. 36 illustrates a top, perspective view of another embodiment of a surgical retractor 2000' according to the present disclosure that includes two auxiliary retractor blades. The surgical retractor 2000' is similar in many aspects to retractor 2000, with a distinction being the type of blade arms 3110' and 3210' utilized to attach the auxiliary blades 3315', 3415' to the retractor 2000'. As surgical retractor 2000' shares many characteristics with surgical retractor 2000, like reference numbers will be used with like elements. The surgical retractor 2000' includes a base portion 2005' connectable to an anterior arm 2020' having an anterior blade 2025', and a posterior arm 2010' having a posterior blade 2015'. Notably, in this embodiment, the posterior blade 2015' is positioned anteriorly to the anterior blade 2025'.

The surgical retractor 2000' also includes modular blade assemblies 3100' and 3200'. As discussed elsewhere, modular blade assemblies 3100' and 3200' include many features found on retractors 100, 200, 800, and 1000, such as an adjustment mechanism 3165', 3265' that, when rotated, adjusts the position of auxiliary blades 3315', 3415' relative to posterior blade 2015' and anterior blade 2025', which adjustment increases or decreases the surgical corridor created by the various retractor blades. Modular blade assemblies 3100' and 3200' are designed to snap onto, mechanically engage, or otherwise be securely attached to anterior blade arm 2020 and the posterior blade arm 2010'.

The modular blade assemblies 3100' and 3200' may include substantially the same components. Each of the modular blade assemblies 3100' and 3200' include a base portion (e.g., anterior base portion 3105' and posterior base portion 3205') to facilitate connection of auxiliary blades 3315' and 3415' to the anterior arm 2020' and the posterior arm 2010', respectively. The modular blade assemblies 3100' and 3200' also include blade arms 3110', 3210' to facilitate connection of the auxiliary blades 3315' and 3415' to the anterior base portion 3105' and the posterior base portion 3205', respectively.

For example, the blade arms 3110', 3210' are movable with respect to base portions 3105', 3205' and may, in some embodiments, be entirely removed from the base portions 3105', 3205'. This modularity allows for the use of different base portions 3105', 3205' with different blades 3315', 3215'. Different designs for base portions and different designs for blades are discussed in greater detail below. In some embodiments, a set of instruments for a modular blade assembly includes (1) a single base portion and two or more distinct retractor blades, (2) two or more base portions and a single retractor blade, or (3) two or more base portions and two or more retractor blades. In some embodiments, it may be advantageous to use different arrangements of base portions and/or retractor blades during a single procedure as the needs of the user change over the course of the procedure.

Figure 37:
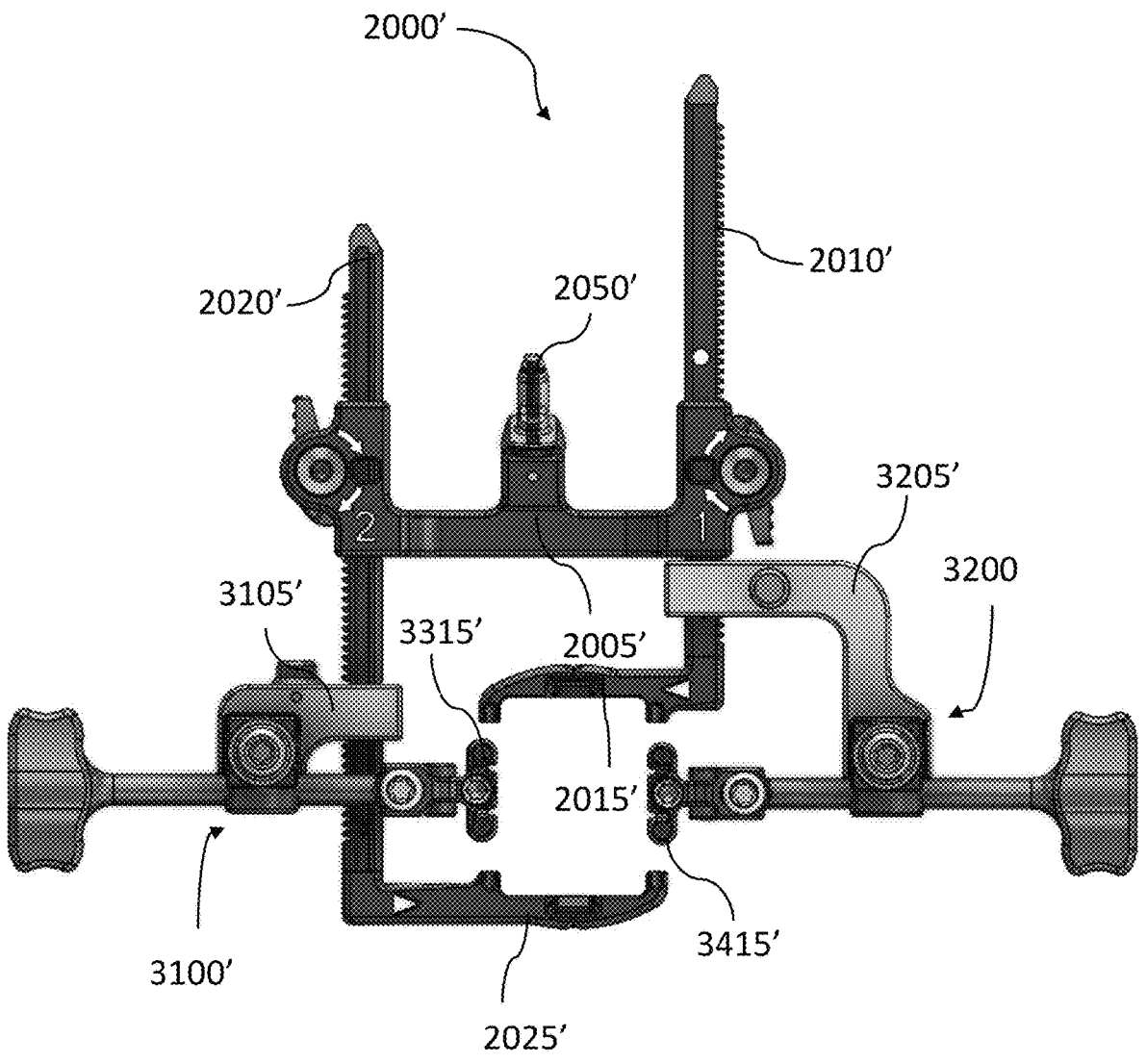
FIGS. 37 and 38 illustrate top views of the surgical retractor of FIG. 36 as the blades of the surgical retractor are moved and positioned.
Figure 38:
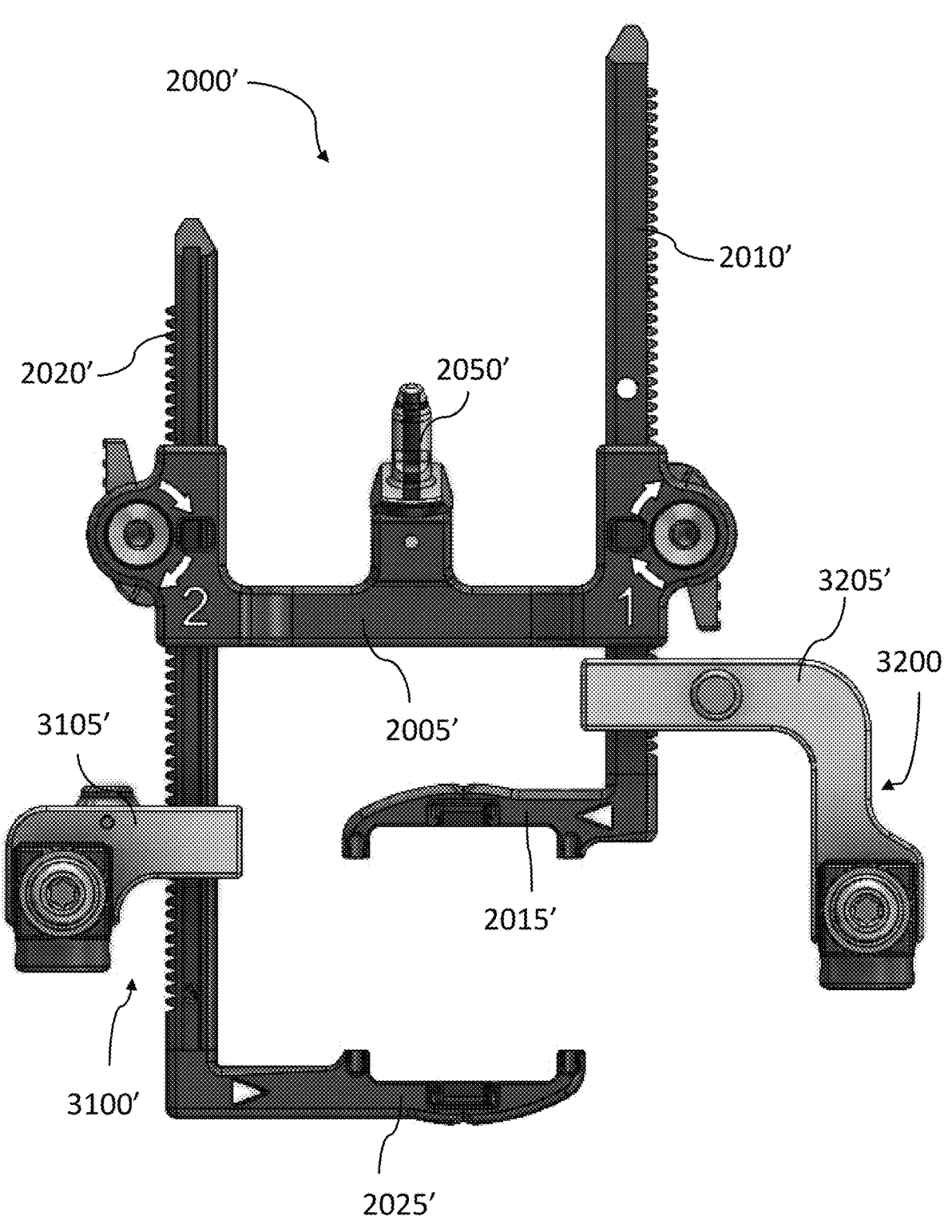

FIGS. 37 (with auxiliary blades 3315' and 3415') and 38 (without auxiliary blades) illustrate top views of the surgical retractor 2000' of FIG. 36 as the blades of the surgical retractor are moved and positioned. Specifically, movement of the anterior blade arm 2020' and the posterior blade arm 2010' through the base portion 2005' adjusts the position of the anterior blade 2025' and the posterior blade 2015', respectively. Additionally, movement of components of the modular blade assemblies 3100' and 3200' (e.g., first blade arm 3110' and/or second blade arm 3210') positions the first auxiliary blade 3315' and the second auxiliary blade 3415' relative to the anterior blade 2025' and the posterior blade 2015', respectively. The surgical corridor created with the surgical retractor 2000' can have a generally rectangular or square shape; however, it will be appreciated that other shapes of the surgical corridor can be achieved, such as through different shapes of the blades 2015', 2025', 3315', and/or 3415'.

The first auxiliary blade 3315' may be positioned substantially perpendicular to the anterior and/or posterior blades 2015', 2025'. Similarly, the second auxiliary blade 3415' may be positioned substantially perpendicular to the anterior and/or posterior blades 2015', 2025'. The first auxiliary blade 3115' and the second auxiliary blade 3215' may be substantially opposite to each other. The anterior and/or posterior base portions 3105', 3205' may include adjustment mechanisms (e.g., buttons, switches, knobs, pawls, etc.) that can adjust an angle of the auxiliary blades 3315', 3415' in at least two planes, where the at least two planes are orthogonal to each other. For example, an angle of the auxiliary blades 3315', 3415' may be adjusted into and/or out of a plane of the surgical corridor (e.g., forward and/or backward). Additionally, the anterior and/or posterior base portions 3105', 3205' may include adjustment mechanisms that can adjust an angle of the auxiliary blades 3315', 3415' in a plane orthogonal to the anterior and posterior blades 2015', 2025'.

Figure 39:
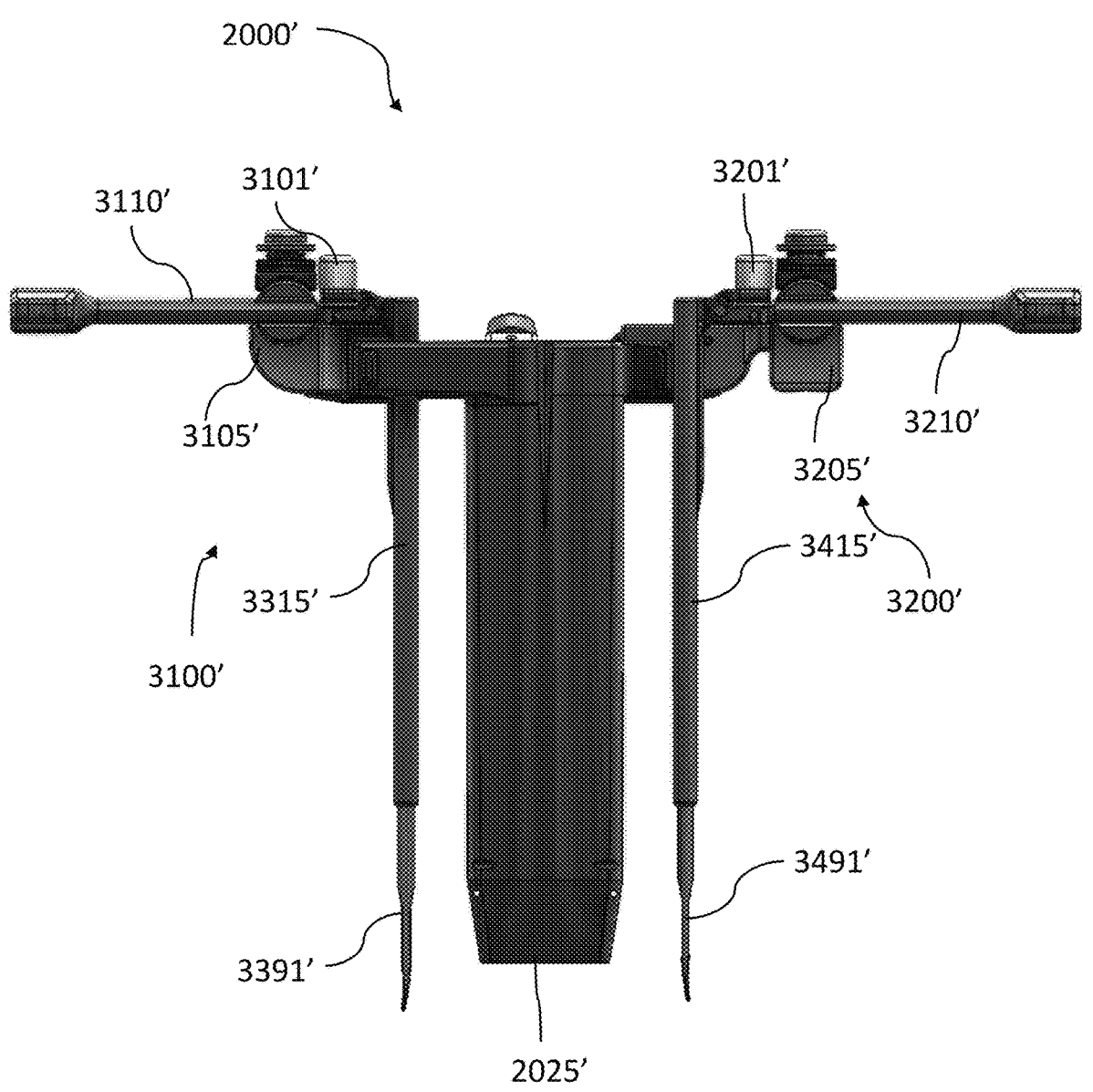
FIG. 39 illustrates an end view of the surgical retractor of FIG. 36 in a first position.
Figure 40:
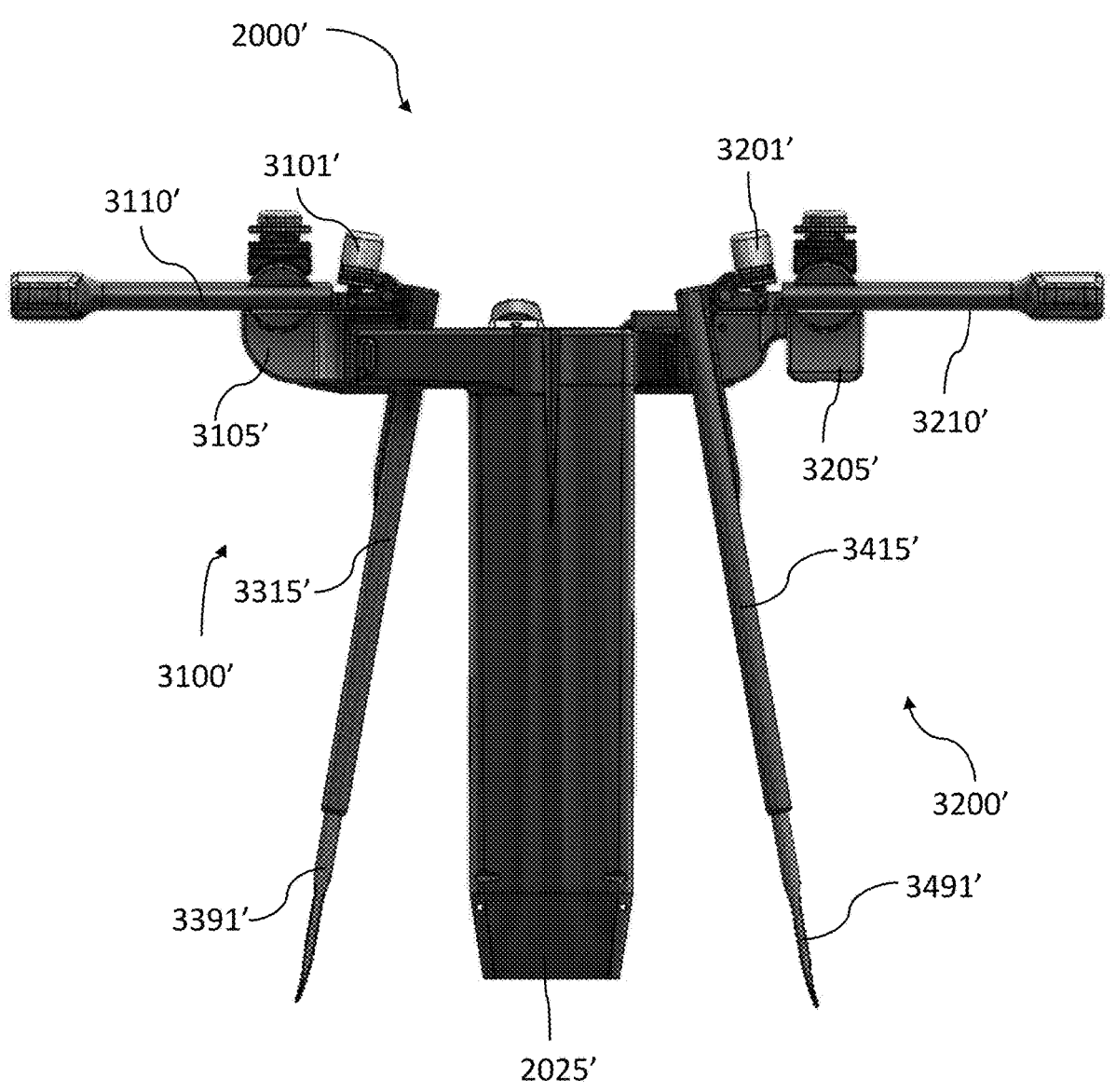
FIG. 40 illustrates an end view of the surgical retractor of FIG. 39 in a second position.

FIGS. 39 and 40 illustrate end views of the surgical retractor 2000' of FIG. 36. As illustrated, both the first auxiliary blade 3315' and the second auxiliary blade 3415' have a toe, angle, or bias relative to (i) each other and (ii) the anterior and/or posterior blades 2015', 2025'. The first auxiliary blade 3315' and the second auxiliary blade 3415' may have an outward angle or bias relative to the anterior and/or posterior blades 2015', 2025', respectively. This outward angle or bias may be built-in to the structure of the first auxiliary blade 3315' and/or the second auxiliary blade 3415'. The outward angle or bias allows the first auxiliary blade 3315' and/or the second auxiliary blade 3415' to contact tissue or other patient anatomy and to retract the tissue or patient anatomy without bending inwardly. If the first auxiliary blade 3315' and/or the second auxiliary blade 3415' did not include an outward angle or bias, the first auxiliary blade 3315' and/or the second auxiliary blade 3415' would undesirably bend inwardly upon contact with tissues or patient anatomy, and potentially block the surgical corridor. As illustrated in FIGS. 39 and 40, in some embodiments, the auxiliary blades may be independently angled outwardly as desired for the surgical corridor based on the particular patient's anatomy and the surgeon's needs. FIG. 40 shows both auxiliary blades angled outwardly more compared to FIG. 39, but it will be appreciated that the auxiliary blades can be independently adjustable.

Figure 41:
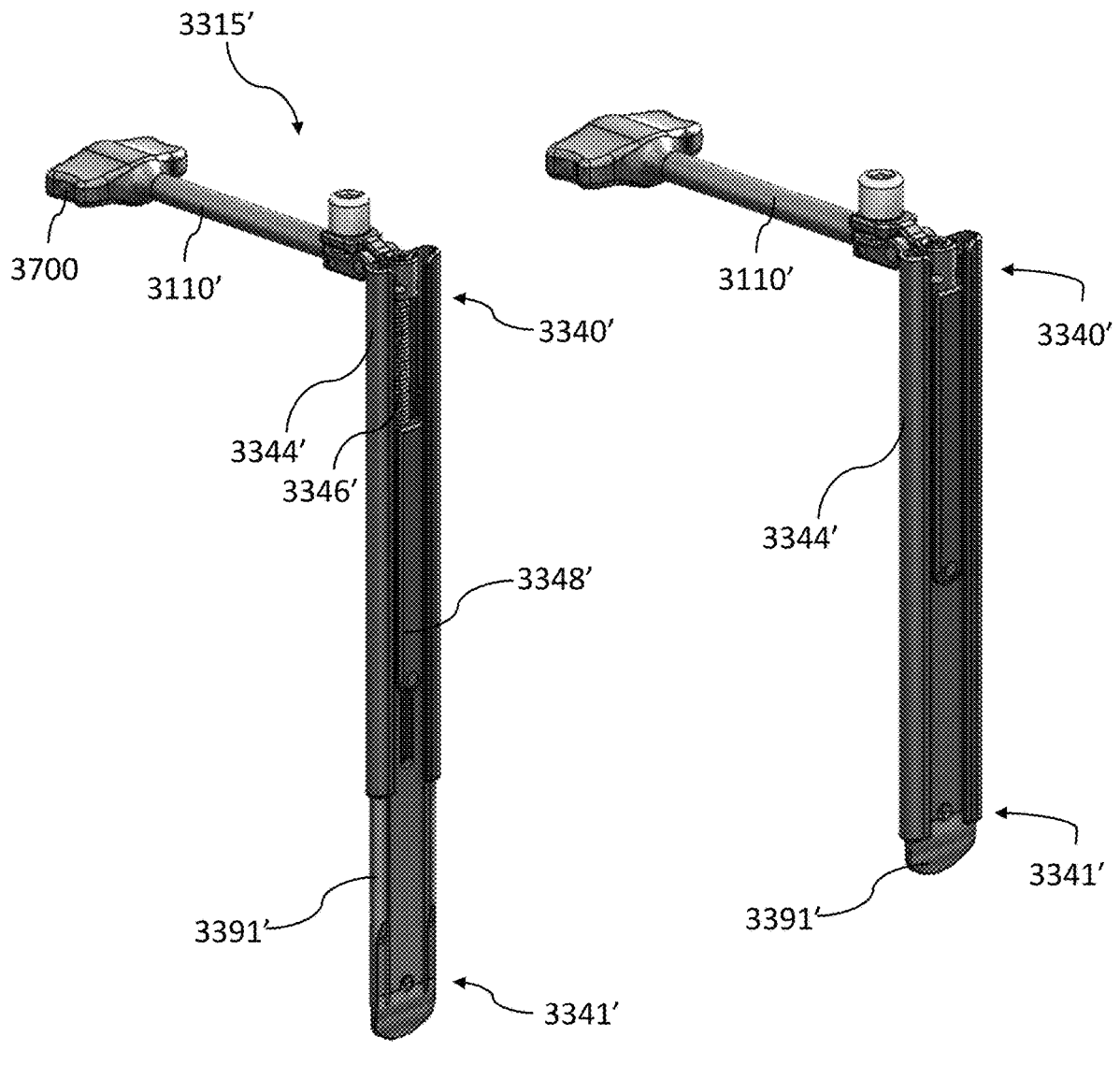
FIGS. 41A and 41B illustrate another embodiment of an auxiliary blade for use with the surgical retractor of FIGS. 36 through 40.
Figure 42:
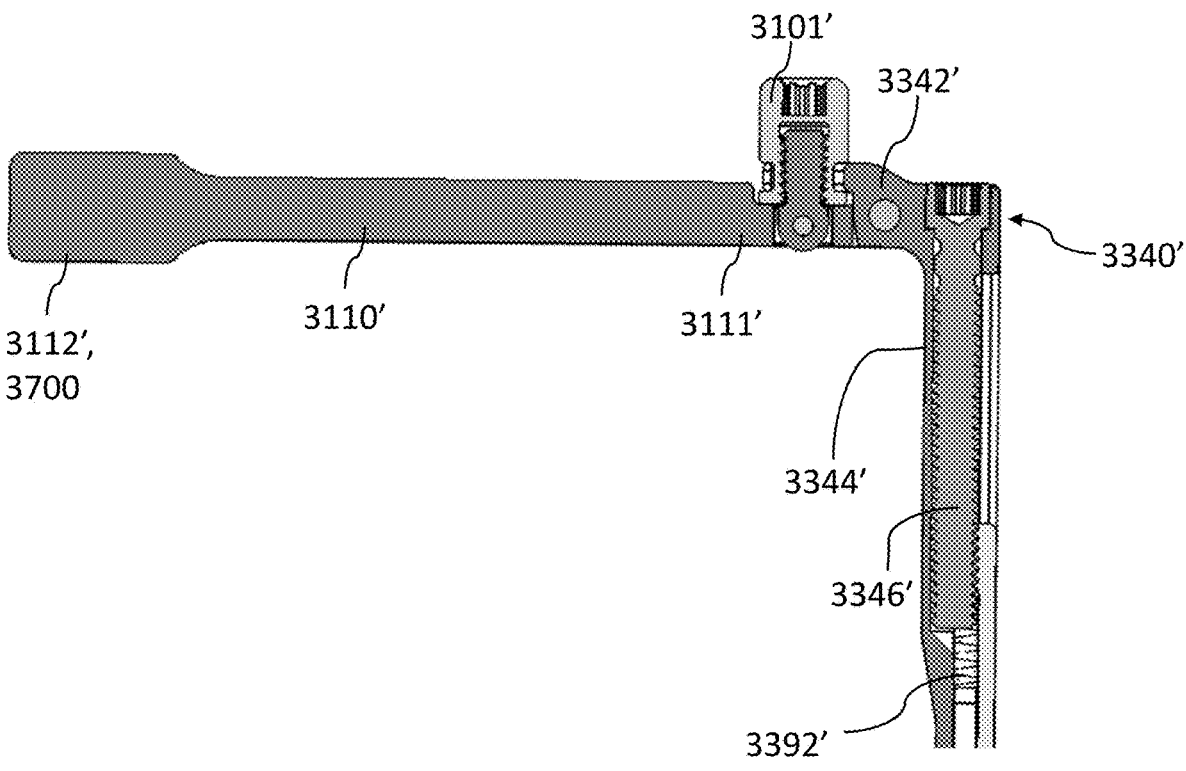
FIG. 42 illustrates a cross-sectional view of the auxiliary blade from FIGS. 41A and 41B in connection with a blade arm.

FIGS. 41A through 42 illustrate an auxiliary blade 3315 in connection with the blade arm 3110'. The auxiliary blade 3315' may be substantially identical to auxiliary blade 3315 (and, thus, auxiliary blade 3415) discussed with respect to FIGS. 31 through 34B. Though FIGS. 41A to 42 will be discussed with respect to first auxiliary blade 3315', it is to be understood that the second auxiliary blade 3415' is substantially identical to the first auxiliary blade 3315', such that the discussion of the first auxiliary blade 3315' applies to the second auxiliary blade 3415'. One distinction between the auxiliary blades 3115, 3215 and auxiliary blades 3315', 3215' is the blade arms 3110', 3210'.

As before, the auxiliary blade 3315' includes a sheath 3344', an actuator 3346' in connection with a proximal end 3340' of the auxiliary blade 3315', a lead or bridge 3348' in connection with the actuator 3346' and the sheath 3344', and a blade tip or shim 3391'. The auxiliary blade 3315' extends from the proximal end 3340' to the distal end 3341', where the distal end 3341' may correspond to a distal end of the blade tip 3391'. Also as before, the blade tip 3391' may be biased through one or more springs 3392' (not illustrated) in a first position relative to the sheath 3344'. In this embodiment, the proximal end 3340' of the auxiliary blade 3315' may include a projection 3342' that engages a release mechanism 3301' and a portion of the blade arm 3110'.

The blade arm 3110' includes a first end 3111' and a second end 3112' opposite the first end 3111'. The first end 3111' defines a first void (not illustrated) to engage the projection 3342' at the proximal end 3340' of the auxiliary blade 3315'. The first void also receives the release mechanism 3101'. The second end 3112' includes a hold 3700, which a user may grasp and rotate/actuate to adjust blade 3315'. For example, the user may grasp the hold 3700 and rotate the hold clockwise and/or counterclockwise, thereby adjust the angle of the blade 3315' in a plane parallel to the blade 3315'. The angle adjusted may be in any plane of the patient desired to create the appropriate surgical corridor; for example, in a sagittal plane, a transverse plane, etc.

Figure 43:
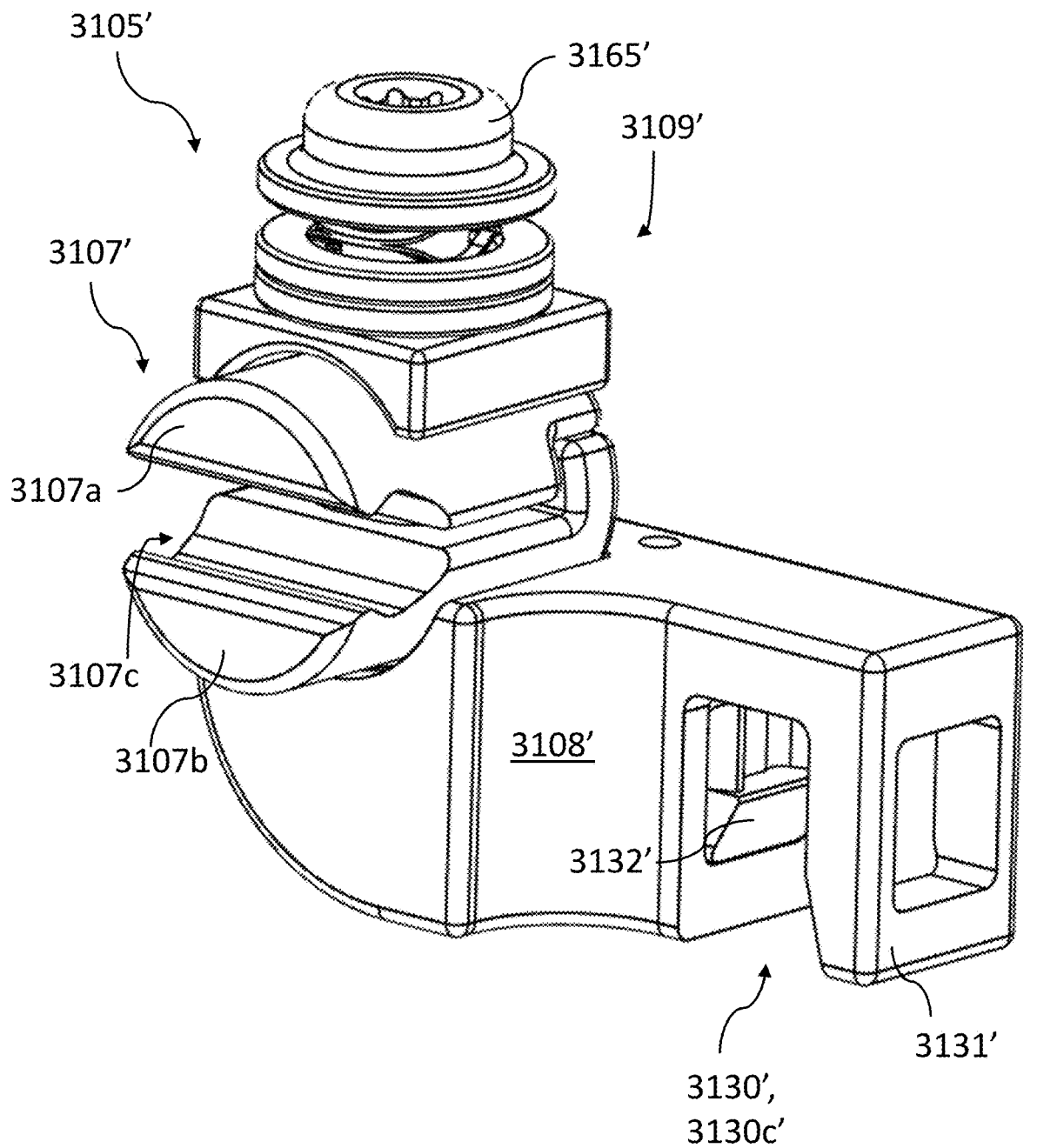
FIG. 43 illustrates one embodiment of an anterior base portion for use with any one of the surgical retractors of FIGS. 16 through 41B.

FIG. 43 illustrates another embodiment of an anterior base portion 3105' for use with any one of the surgical retractors 2000, 2000' of FIGS. 16 through 40. Similar to the anterior base portion 3105 of FIGS. 25 to 27, the anterior base portion 3105' includes a body 3108', which may be substantially rectangular or square with various projections or extensions. For example, the body 3108' includes a hooked portion 3130' or arm engagement portion. The hooked portion 3130' includes a hook 3131' extending away from the body 3108' and forming a channel 3130c' for engaging/receiving the anterior arm 2020' of the surgical retractor 2000'. The hooked portion 3130' also includes a latch 3132' and a spring 3133'. When the hooked portion 3130' is positioned over the anterior arm 2020', the latch 3132' is pushed into the body 3108 of the anterior base portion 3105', thereby compressing the spring 3133'. When the hooked portion 3130' is secured against the anterior arm 2020', the spring 3133' biases the latch 3132' to abut a surface of the anterior arm 2020', thereby mechanically securing the anterior base portion 3105' to the anterior arm 2020'. Though not illustrated, the anterior base portion includes a release mechanism 3102' to release the anterior base portion 3105 from the anterior arm 2020' of the retractor 2000'.

The body 3108' also includes or receives a clamp 3107' for engaging a blade arm 3110'. The clamp 3107' may include a top portion 3107a and a bottom portion 3107b that together define a channel 3107c for receiving a portion of the blade arm 3110'. Rotation of the adjustment mechanism 3165' in a first direction may cause the clamp 3107' to open and receive the blade arm 3110'. Rotation of the adjustment mechanism 3165' in a second direction may cause the clamp 3107' to close around the blade arm 3110', thereby securing the blade arm 3110' (and auxiliary blade 3115') to the anterior base portion 3105'.

Figure 44:
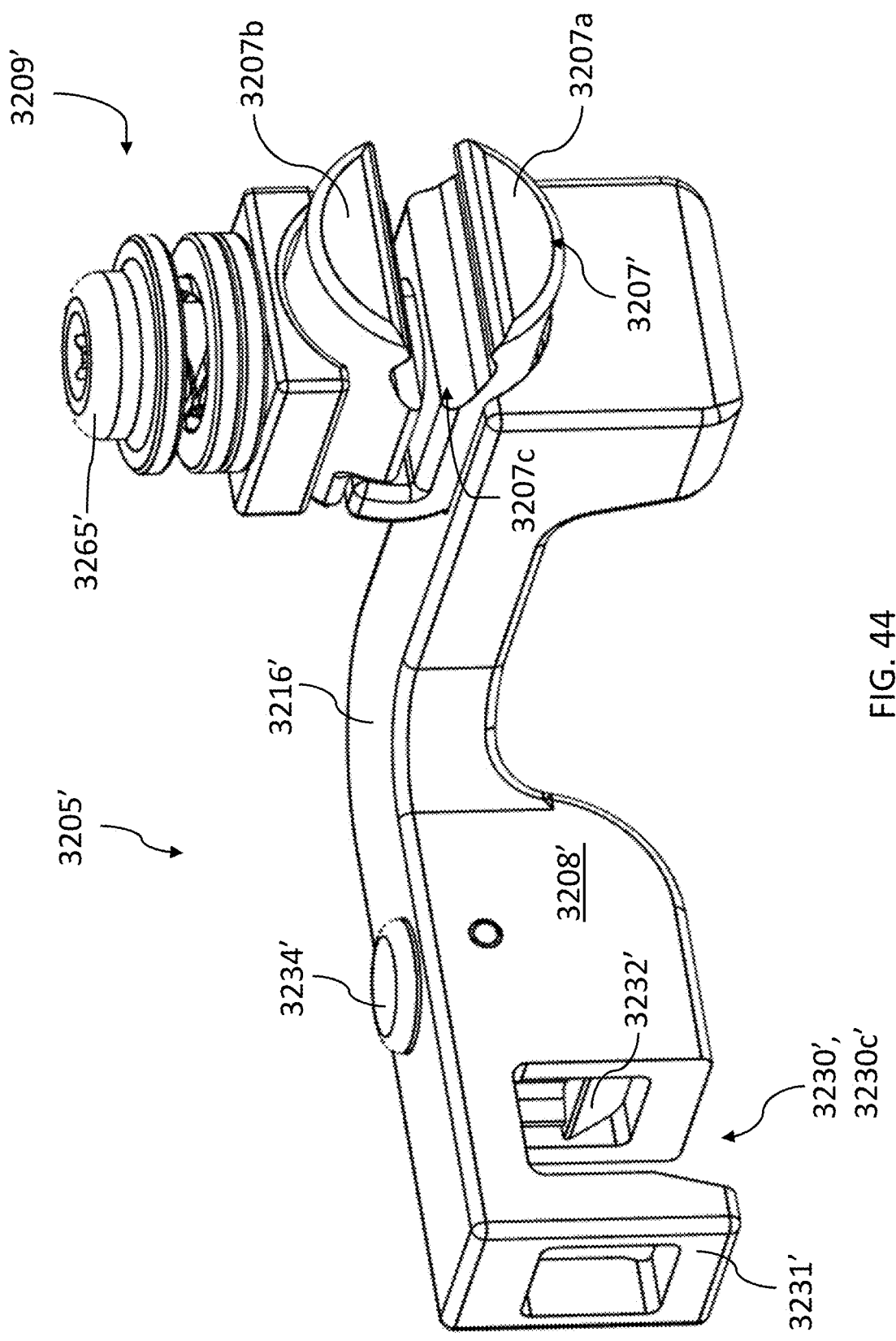
FIG. 44 illustrates one embodiment of a posterior base portion for use with any one of the surgical retractors of FIGS. 16 through 41B.

FIG. 44 illustrates another embodiment of a posterior base portion 3205' for use with any one of the surgical retractors 2000, 2000' of FIGS. 16 through 40. The posterior base portion 3205' includes a body 3208', which may be rectangular or square with various projections or extensions. For example, the body 3208' includes a hooked portion or arm engagement portion 3230'. The hooked portion 3230' includes a hook 3231' extending away from the body 3208' and forming a channel 3230c' for engaging the posterior arm 2010' of the surgical retractor 2000'. The hooked portion 3230' also includes a latch 3232' and a spring 3233'. When the hooked portion 3230' is positioned over the posterior arm 2010', the latch 3232' is pushed into the body 3208' of the posterior base portion 3205', thereby compressing the spring 3233'. When the hooked portion 3230' is secured over the posterior arm 2010', the spring 3233' biases the latch 3232' to abut a surface of the posterior arm 2010', thereby mechanically securing the posterior base portion 3205' to the posterior arm 2010'. Though not illustrated, the posterior base portion 3205' includes a release mechanism 3202' to release the posterior base portion 3205' from the posterior arm 2010' of the retractor 2000'.

The body 3208' also includes an extension 3216', which may provide the posterior base portion 3205' with an overall L-shape. The extension 3216' allows the posterior base portion 3205' to position an auxiliary blade 3215' anterior relative to the posterior blade 2015'. That is, the extension 3216' extends anteriorly past the posterior blade 2015' and positions the auxiliary blade 3215' anterior relative to the posterior blade 2015'. This allows the auxiliary blade 3215' to be substantially parallel to the auxiliary blade 3115' and create a rectangular surgical corridor.

The body 3208' also includes or receives a clamp 3207' for engaging a blade arm 3210'. The clamp 3207' may include a top portion 3207a and a bottom portion 3207b that together define a channel 3207c for receiving a portion of the blade arm 3210'. Rotation of the adjustment mechanism 3265' in a first direction may cause the clamp 3207' to open and receive the blade arm 3210'. Rotation of the adjustment mechanism 3265' in a second direction may cause the clamp 3207' to close around the blade arm 3210', thereby securing the blade arm 3210' (and auxiliary blade 3215') to the anterior base portion 3205'.

FIG. 45 is a flowchart of one example method 5000 of using any one of the surgical retractors of FIGS. 1 through 40. The method 5000 may include attaching an anterior cabin to an anterior arm of a base retractor, the anterior arm having an anterior blade, at 5005. The anterior cabin may be any of the base portions 305, 405, 505, 605, 705, 905, 1105, 3105, or 3105'. The base retractor may be any of the retractors 100, 200, 1000, 2000, or 2000'. The method 5000 may also include attaching a posterior cabin to a posterior arm of the base retractor, the posterior arm having a posterior blade, the posterior blade being substantially parallel to the anterior blade, at 5010. The posterior cabin may be any of the base portions 1205, 3205, or 3205'.

The method 5000 may also include securing a first auxiliary blade to the anterior cabin, the first auxiliary blade oriented orthogonal to the anterior blade and having an outward bias relative to the anterior blade, at 5015. The first auxiliary blade may be any of the blades 315, 415, 515, 615, 715, 915, 1115, 3115, or 3115'. The method 5000 may further include securing a second auxiliary blade to the posterior cabin, the second auxiliary blade oriented orthogonal to the posterior blade and having an outward bias relative to the posterior blade, each of the first auxiliary blade and the second auxiliary blade being independently moveable relative to the anterior blade, the posterior blade, and each other. The second auxiliary blade may any of the blades 1125, 3215, or 3215'.

In some embodiments, attaching an anterior cabin to an anterior arm of a base retractor may include positioning an engagement portion or hook portion of the anterior cabin (see FIGS. 25 to 27 and 43) over the anterior arm, such that the arm is within a channel of the attachment portion, depressing a latch contained within a distal portion of the anterior cabin, and releasing the latch such that the hook portion of the anterior cabin is secured to a top surface of the anterior arm and the latch is adjacent a surface of the anterior arm. Attaching a posterior cabin to a posterior arm of the base retractor may include positioning an attachment portion or hook portion of the posterior cabin (see FIGS. 28 to 30 and 44) over the posterior arm, such that the arm is within a channel of the attachment portion, depressing a latch contained within a distal portion of the posterior cabin, and releasing the latch such that the hook portion of the posterior cabin is secured to a top surface of the posterior arm and the latch is adjacent a bottom surface of the posterior arm.

In some embodiments, securing a first auxiliary blade to the anterior cabin includes connecting a proximal end of the first auxiliary blade to a first blade arm and securing the first blade arm to a portion of the anterior cabin. Securing the first blade arm to a portion of the anterior cabin may include clamping a portion of the first blade arm within a clamp of the anterior cabin.

According to this disclosure, some exemplary methods of using the surgical retractors disclosed herein include creating an access path through a patient's skin to a surgical site, inserting a pair of retractor blades through the skin, advancing the retractor blades toward the surgical site, and separating the blades from each other to establish a surgical corridor for performing a surgical procedure at the surgical site. Creating an access path may include one or more of the following: (a) after creating an incision in the skin at desired location, advancing a guide wire toward the surgical site; and (b) advancing over the guide wire one or more dilators so to sequentially enlarge the access path. In some embodiments, the one or more dilators are in electrical communication with a neural monitoring system configured to detect nerves that may be along or near the access path. In some embodiments, the retractor blades are already connected to a retractor base portion or may be connected to a retractor base portion after having been advanced toward the surgical site.

In some embodiments, the retractor base portion is then attached a support structure, such as an A-arm that is attached to a surgical table. Separating the blades from each other may be achieved by moving one or both blades, which movement may be achieved either by simply pulling the blades apart or by using an adjustment mechanism to adjust the position of one or both blades relative to the retractor base portion. In some embodiments, after the retractor blades have been separated, it may be desirable to either further enlarge the surgical corridor or provide additional barriers to reduce or prevent the encroachment of surrounding tissue into the surgical corridor. In such situations, a modular blade assembly may be used by inserting the retractor blade of the modular blade assembly down into the surgical corridor until the modular blade assembly can be secured to one of the retractor arms of the existing retractor. If additional enlargement or an additional barrier is desired, another modular blade assembly may be used in a similar manner to the first but secured to the other retractor arm.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It should also be noted that some of the embodiments disclosed herein may have been disclosed in relation to a particular surgical procedure (e.g., a lumbar spinal procedure); however, other procedures (e.g., cervical spine, thoracic spine, etc.) are also contemplated.

In one embodiment, the terms "about" and "approximately" refer to numerical parameters within 10% of the indicated range. The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the author(s) of this disclosure for carrying out the embodiments disclosed herein. Of course, variations on these described embodiments will become apparent to those of ordinary skill in the art upon reading the foregoing description. The author(s) expects skilled artisans to employ such variations as appropriate, and the author(s) intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Although this disclosure provides many specifics, these should not be construed as limiting the scope of any of the claims that follow, but merely as providing illustrations of some embodiments of elements and features of the disclosed subject matter. Other embodiments of the disclosed subject matter, and of their elements and features, may be devised which do not depart from the spirit or scope of any of the claims. Features from different embodiments may be employed in combination. Accordingly, the scope of each claim is limited only by its plain language and the legal equivalents thereto.

Embodiments

The following embodiments are provided as examples only of specific configurations, materials, arrangements, etc. contemplated by the authors of this disclosure:

Embodiment 1. A surgical retractor comprising:
a base portion comprising first and second extensions, the first extension having a first receiving area, the second extension having a second receiving area, and one or more engagement portions;
a posterior retractor blade with proximal and distal ends, the posterior retractor blade having a first retractor arm extending from the proximal end, the first retractor arm configured to be slidingly received by the first receiving area of the base portion; and
an anterior retractor blade with proximal and distal ends, the anterior retractor blade having a second retractor arm extending from the proximal end, the second retractor arm configured to be slidingly received by the second receiving area of the base portion;
wherein the posterior and anterior retractor blades together create an adjustable surgical corridor; and wherein the posterior and anterior retractor blades are independently adjustable relative to the base portion.

Embodiment 2. The surgical retractor of Embodiment 1 or 2, wherein at least one of the first and second receiving areas comprises a ratchet mechanism configured to lock the first or second retractor arm in position relative to the base portion as the first or second retractor arm is translated through the first or second receiving area.

Embodiment 3. The surgical retractor of Embodiment 2, wherein the first or second retractor arm comprises ratchet teeth along an exterior surface, the ratchet teeth being configured to engage the ratchet mechanism.

Embodiment 4. The surgical retractor of Embodiment 2 or 3, wherein the ratchet mechanism comprises a release lever that when pressed causes the ratchet mechanism to disengage from the first or second retractor arm to allow free movement of the first or second retractor arm through the first or second receiving area.

Embodiment 5. The surgical retractor of Embodiment 1, 2, 3, or 4, wherein at least one of the first and second receiving areas comprises an advancement mechanism that when rotated adjusts the position of the first or second retractor arm relative to the base portion.

Embodiment 6. The surgical retractor of Embodiment 1, 2, 3, 4, or 5, wherein at least one of the posterior and anterior retractor blades is integral with the first or second retractor arm. Embodiment 7. The surgical retractor of Embodiment 1, 2, 3, 4, 5, or 6, wherein at least one of the posterior and anterior retractor blades is functionally integral with the first or second retractor arm, respectively.

Embodiment 8. The surgical retractor of Embodiment 1, 2, 3, 4, 5, 6, or 7, wherein at least one of (a) the posterior retractor blade and first retractor arm and (b) anterior retractor blade and second retractor arm is unitary.

Embodiment 9. The surgical retractor of Embodiment 1, 2, 3, 4, 5, 6, 7, or 8, wherein at least one of (a) the posterior retractor blade and first retractor arm and (b) anterior retractor blade and second retractor arm is formed of a single material.

Embodiment 10. The surgical retractor of Embodiment 1, 2, 3, 4, 5, 6, 7, 8, or 9, wherein the posterior retractor blade defines an axis that is substantially orthogonal to an axis defined by the first retractor arm; and wherein the anterior retractor blade defines an axis that is substantially orthogonal to an axis defined by the second retractor arm.

Embodiment 11. The surgical retractor of Embodiment 10, wherein the respective axes of the posterior and anterior retractor blades are substantially parallel to each other and remain substantially parallel as the posterior and anterior retractor blades are independently adjusted relative to the base portion so as to adjust the size of the surgical corridor.

Embodiment 12. The surgical retractor of Embodiment 10 or 11, wherein the respective axes of the posterior and anterior retractor blades are substantially parallel to each other and remain so as the posterior and anterior retractor blades are adjusted relative to each other.

Embodiment 13. The surgical retractor of Embodiment 1, 2, 3, 4, 5, 6, 7, 8, 9, 10, 11, or 12, wherein at least one of the posterior and anterior retractor blades comprises at least one alignment feature at its proximal end, the alignment feature configured to provide an indication of the orthogonality of the surgical retractor relative to a surgical site. Embodiment 14. The surgical retractor of Embodiment 13, wherein the alignment feature is radiographically identifiable.

Embodiment 15. The surgical retractor of Embodiment 13 or 14, wherein the alignment feature comprises a through hole in the proximal end of the first or second retractor.

Embodiment 16. The surgical retractor of Embodiment 13, 14, or 15, wherein the alignment feature comprises a triangular-shaped through hole in the proximal end of the first or second retractor with the triangle pointing toward the surgical corridor.

Embodiment 17. The surgical retractor of Embodiment 13, 14, 15, or 16, wherein the surgical site is a disc space of a patient's spine.

Embodiment 18. The surgical retractor of Embodiment 17, wherein the orthogonality of the surgical retractor relative to the disc space is achieved through a lateral procedure. Embodiment 19. The surgical retractor of Embodiment 18, wherein surgical retractor is configured to extend at least partially through a portion of the patient's psoas muscle.

Embodiment 20. The surgical retractor of Embodiment 1, 2, 3, 4, 5, 6, 7, 8, 9, 10, 11, 12, 13, 14, 15, 16, 17, 18, or 19, wherein at least one of the posterior and anterior retractor blades comprises a marking to indicate whether it is to be positioned posteriorly or anteriorly.

Embodiment 21. The surgical retractor of Embodiment 1, 2, 3, 4, 5, 6, 7, 8, 9, 10, 11, 12, 13, 14, 15, 16, 17, 18, 19, or 20, wherein the base portion comprises one or more markings to indicate which extension is to be positioned posteriorly or anteriorly.

Embodiment 22. The surgical retractor of Embodiment 1, 2, 3, 4, 5, 6, 7, 8, 9, 10, 11, 12, 13, 14, 15, 16, 17, 18, 19, 20, or 21, wherein the surgical retractor is configured to be used when a patient is in a prone position.

Embodiment 23. The surgical retractor of Embodiment 1, 2, 3, 4, 5, 6, 7, 8, 9, 10, 11, 12, 13, 14, 15, 16, 17, 18, 19, 20, or 21, wherein the surgical retractor is configured to be used when a patient is in a lateral position.

Embodiment 24. The surgical retractor of Embodiment 1, 2, 3, 4, 5, 6, 7, 8, 9, 10, 11, 12, 13, 14, 15, 16, 17, 18, 19, 20, 21, 22, 23, wherein the base portion comprises an anterior face, a posterior face, a top face, and a bottom face; wherein the first and second receiving areas each extend from the anterior face to the posterior face.

Embodiment 25. The surgical retractor of Embodiment 24, wherein the one or more engagement portions extends from the posterior face of the base portion.

Embodiment 26. The surgical retractor of Embodiment 1, 2, 3, 4, 5, 6, 7, 8, 9, 10, 11, 12, 13, 14, 15, 16, 17, 18, 19, 20, 21, 22, 23, 24, or 25, wherein at least one of the first and second retractor arms comprises a top surface comprising markings to indicate a size of the surgical corridor.

Embodiment 27. The surgical retractor of Embodiment 26, wherein at least one of the first and second receiving areas comprises a window for viewing the markings on the first or second retractor arm.

Embodiment 28. The surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, or 27, wherein at least one of the posterior and anterior retractor blades comprises a central channel extending from the proximal end toward the distal end.

Embodiment 29. The surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, 27, or 28, wherein at least one of the posterior and anterior retractor blades comprises at least one lateral channel extending from the proximal end toward the distal end.

Embodiment 30. The surgical retractor of Embodiment 29, further comprising an anchor, the anchor comprising a threaded shank and a projection configured to be received by the at least one lateral channel.

Embodiment 31. The surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein the posterior and anterior retractor blades together form a tube when abutting each other.

Embodiment 32. The surgical retractor of Embodiment 31, wherein the tube substantially encloses the surgical corridor.

Embodiment 33. The surgical retractor of Embodiment 31 or 32, wherein the tube has a cross section that is substantially circular.

Embodiment 34. The surgical retractor of Embodiment 31 or 32, wherein the tube has a cross section that is substantially oval.

Embodiment 35. The surgical retractor of Embodiment 31 or 32, wherein the tube has a cross section that is substantially rectangular.

Embodiment 36. The surgical retractor of Embodiment of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, wherein the posterior and anterior retractor blades are configured to slide over a dilator.

Embodiment 37. The surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein the posterior and anterior retractor blades form a substantially rectangular surgical corridor.

Embodiment 38. A method of using a surgical retractor, the method comprising:

making an incision in a patient's skin at a position lateral to the patient's spine;

locating a surgical site on the spine;

inserting the posterior and anterior retractor blades of the surgical retractor of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37;

advancing the surgical retractor toward the surgical site to create a surgical corridor to access the surgical site;

positioning the distal end of the posterior retractor blade at a posterior position of the surgical site;

anchoring the posterior retractor blade at the posterior position; and enlarging the surgical corridor.

Embodiment 39. The method of Embodiment 38, wherein locating the surgical site on the spine comprises:

advancing a K-wire toward the surgical site and embedding a distal end of the K-wire into a tissue at the surgical site; and sequentially advancing an inner dilator and an outer dilator over the K-wire toward the surgical site.

Embodiment 40. The method of Embodiment 39, wherein advancing a K-wire toward the surgical site comprises traversing at least a portion of the psoas muscle.

Embodiment 41. The method of Embodiment 39 or 40, wherein at least one of the inner and outer dilators comprises at least one electrode and is configured to provide neural monitoring as the dilator is advanced toward the surgical site.

Embodiment 42. The method of Embodiment 41, wherein the at least one electrode is configured to provide a plexus map.

Embodiment 43. The method of Embodiment 39, 40, 41, or 42, wherein the inner and outer dilators are circular in cross section.

Embodiment 44. The method of Embodiment 39, 40, 41, or 42, wherein the inner and outer dilators are oval in cross section.

Embodiment 45. A retractor for use in a surgical procedure, the retractor comprising:

a base having (i) an anterior arm connectable to the an anterior end of the base and having an anterior blade, and (ii) a posterior arm connectable to a posterior end of the base and having a posterior blade;

an anterior cabin connectable to the anterior arm, the anterior cabin for receiving a first auxiliary blade, the first auxiliary blade comprising:

a sheath extending from a proximal end to a distal end, a blade tip at least partially within the sheath and slidable within the sheath, a spring in connection with the blade tip, the spring biasing the blade tip distally relative to the sheath; and a posterior cabin connectable to the posterior arm, the posterior cabin for receiving a second auxiliary blade, the posterior cabin having an extension, such that the second auxiliary blade is positionable anterior to the posterior blade, the second auxiliary blade being substantially identical to the first auxiliary blade, wherein each of the first auxiliary blade and the second auxiliary blade is adjustable in length and in angle in at least two planes, and wherein the distal ends of the first auxiliary blade and the second auxiliary blade are angled outwardly relative to each other.

Embodiment 46. The retractor of Embodiment 45, wherein the sheath of the first auxiliary blade comprises an engagement mechanism at the proximal end, the engagement mechanism for attaching the first auxiliary blade to the anterior cabin.

Embodiment 47. The retractor of Embodiment 45 or Embodiment 45, wherein the at least two planes are orthogonal to each other.

Embodiment 48. The retractor of any one of Embodiments 45 to 47, wherein the first auxiliary blade further comprises a blade arm in connection with the proximal end of the sheath, the blade arm for connecting the first auxiliary blade to the anterior cabin.

Embodiment 49. The retractor of Embodiment 48, wherein the blade arm comprises a plurality of teeth for engaging a gear mechanism of the anterior cabin.

Embodiment 50. The retractor of Embodiment 48 or Embodiment 49, wherein the blade arm comprises a rod for engaging a clamp of the anterior cabin.

Embodiment 51. The retractor of any one of Embodiments 45 to 50, wherein the anterior cabin comprises:

a body defining a channel to receive a portion of the first auxiliary blade;

a hook portion extending from the body towards a center line of the retractor, the hook portion for engaging the anterior arm;

a latch for securing the anterior cabin to the anterior arm; and a gear mechanism for engaging the portion of the first auxiliary blade.

Embodiment 52. A retractor for use in a surgical procedure, the retractor comprising:

a base retractor comprising a rack, an anterior arm connectable to the rack and having an anterior blade, and a posterior arm connectable to the rack and having a posterior blade;

a first cabin connectable to the anterior arm, the first cabin for receiving a first auxiliary blade defining a first axis; and a second auxiliary blade connectable to the posterior arm, the second auxiliary blade defining a second axis, wherein each of the first auxiliary blade and the second auxiliary blade is adjustable in length and angulation, and wherein the first and second axes are not parallel to teach other so that each of the first auxiliary blade and the second auxiliary blade has an outward bias relative to the anterior blade and posterior blade, respectively.

Embodiment 53. The retractor of Embodiment 52, wherein the anterior arm defines a slot for receiving a portion of the first cabin.

Embodiment 54. The retractor of Embodiment 52 or Embodiment 53, further comprising a second cabin for connecting the second auxiliary blade to the posterior arm.

Embodiment 55. The retractor of any one of Embodiments 52 to 54, wherein each of the first auxiliary blade and the second auxiliary blade comprise:

a sheath extending from a proximal end to a distal end; and a blade tip in connection with the sheath, the blade tip being biased in a first position.

Embodiment 56. The retractor of any one of Embodiments 52 to 55, further comprising at least one spring for biasing the blade tip in the first position.

Embodiment 57. The retractor of any one of Embodiments 52 to 56, wherein the blade tip transitions from the first position to a second position relative to the sheath when the blade tip contacts patient anatomy during a surgical procedure.

Embodiment 58. The retractor of any one of Embodiments 52 to 57, wherein the blade tip is pressed inwardly from the outward bias when the blade tip is pressed inwardly by patient anatomy during a surgical procedure, and wherein the blade tip returns to the outward bias when not pressed inwardly by the patient anatomy.

Embodiment 59. A method of creating and/or maintaining an exposure in a surgical procedure, the method comprising:

attaching an anterior cabin to an anterior arm of a base retractor, the anterior arm having an anterior blade;

attaching a posterior cabin to a posterior arm of the base retractor, the posterior arm having a posterior blade, the posterior blade being substantially parallel to the anterior blade; securing a first auxiliary blade to the anterior cabin, the first auxiliary blade oriented orthogonal to the anterior blade and having an outward bias relative to the anterior blade; and securing a second auxiliary blade to the posterior cabin, the second auxiliary blade oriented orthogonal to the posterior blade and having an outward bias relative to the posterior blade, each of the first auxiliary blade and the second auxiliary blade being independently moveable relative to the anterior blade, the posterior blade, and each other.

Embodiment 60. The method of Embodiment 59, wherein attaching an anterior cabin to an anterior arm of a base retractor comprises:

positioning a hook portion of the anterior cabin over the anterior arm;

depressing a latch contained within a distal portion of the anterior cabin; and releasing the latch, such that the hook portion of the anterior cabin is secured to a top surface of the anterior arm and the latch is adjacent a bottom surface of the anterior arm.

Embodiment 61. The method of Embodiment 59 or Embodiment 60, wherein attaching a posterior cabin to a posterior arm of the base retractor comprises:

positioning a hook portion of the posterior cabin over the posterior arm, such that an extension of the posterior cabin extends posteriorly past the posterior blade;

depressing a latch contained within a distal portion of the posterior cabin; and releasing the latch, such that the hook portion of the posterior cabin is secured to a top surface of the posterior arm and the latch is [secured to/adjacent] a bottom surface of the posterior arm.

Embodiment 62. The method of any one of Embodiments 59 to 61, wherein securing a first auxiliary blade to the anterior cabin comprises:

connecting a proximal end of the first auxiliary blade to a first blade arm; and securing the first blade arm to a portion of the anterior cabin.

Embodiment 63. The method of Embodiment 62, wherein securing the first blade arm to a portion of the anterior cabin comprises clamping a portion of the first blade arm within a clamp of the anterior cabin.

Embodiment 64. The method of any one of Embodiments 59 to 63, further comprising:

retracting the first auxiliary blade into the anterior cabin; and retracting the second auxiliary blade into the posterior cabin.

Embodiment 65. A retractor for use in a surgical procedure, the retractor comprising:

a base retractor comprising a rack, an anterior arm connectable to the rack and having an anterior blade, and a posterior arm connectable to the rack and having a posterior blade;

a first cabin connectable to the anterior arm, the first cabin for receiving a first auxiliary blade, the first auxiliary blade comprising:

a sheath extending from a proximal end to a distal end; and a blade tip in connection with the sheath, the blade tip being biased in a first position.

Embodiment 66. A self-adjusting retractor blade comprising:

a sheath extending from a proximal end to a distal end, the sheath comprising:

an engagement portion at the proximal end configured for releasable engagement with a surgical retractor system, a channel extending to the distal end; and a blade tip at least partially contained within the channel, the blade tip configured to slide within the channel; wherein the blade tip is biased in a first position relative to the sheath.

Embodiment 67. The self-adjusting retractor blade of Embodiment 66, wherein the sheath defines a first axis that is not orthogonal to a second axis defined by the engagement portion.

Embodiment 68. The self-adjusting retractor blade of Embodiment 66 or Embodiment 67, wherein the engagement portion comprises a pair of extensions configured to engage a receiving mechanism of the surgical retractor system.

Embodiment 69. The self-adjusting retractor blade of any one of Embodiments 66 to 68, wherein the engagement portion comprises a rod configured to engage a clamping mechanism of the surgical retractor system.

Embodiment 70. The self-adjusting retractor blade of any one of Embodiments 66 to 69, further comprising a depth adjustment mechanism positioned near the proximal end configured to adjust the blade tip relative to the sheath.

Embodiment 71. The self-adjusting retractor blade of any one of Embodiments 66 to 70, further comprising an angular adjustment mechanism positioned near the proximal end configured to adjust the angle of the first axis relative to the second axis.

Embodiment 72. A surgical retractor system comprising:

a base having (i) a first retractor arm mechanically engaged to the base and (ii) a second retractor arm mechanically engaged to the base; the first and second retractor arms independently adjustable relative to the base;

a first self-adjusting retractor blade according to claim 22 releasably secured to the first or second retractor arms.

Embodiment 73. The surgical retractor of Embodiment 72, further comprising a second self-adjusting retractor blade according to embodiment 66 releasably secured to the other of the first or second retractor arms.

Embodiment 74. The surgical retractor of Embodiment 72 or Embodiment 73, wherein: the first retractor arm comprises a first retractor blade defining a first plane; the second retractor arm comprises a second retractor blade defining a second plane that is parallel to the first plane.

Embodiment 75. The surgical retractor of Embodiment 74, wherein the first self-adjusting retractor blade is positioned between the first and second planes.

What is claimed:

1. A retractor for use in a surgical procedure, the retractor comprising:
   a base having (i) an anterior arm connectable to a first end of the base and having an anterior blade, and (ii) a posterior arm connectable to a second end of the base and having a posterior blade;
   an anterior cabin removably connectable to the anterior arm, the anterior cabin for receiving a first auxiliary blade, the first auxiliary blade comprising:
      a sheath extending from a proximal end to a distal end,
      a blade tip at least partially within the sheath and slidable within the sheath,
      an adjustment mechanism configured to translate the blade tip along at least a portion of a length of the sheath, and
      a spring in connection with the blade tip, the spring biasing the blade tip distally relative to the adjustment mechanism; and
   a posterior cabin removably connectable to the posterior arm, the posterior cabin for receiving a second auxiliary blade, the posterior cabin having an extension, such that the second auxiliary blade is positionable anterior to the posterior blade, the second auxiliary blade being substantially identical to the first auxiliary blade,
   wherein each of the first auxiliary blade and the second auxiliary blade is adjustable in length and in angle in at least two planes, and
   wherein the distal ends of the first auxiliary blade and the second auxiliary blade are capable of being angled outwardly relative to each other.

2. The retractor of claim 1, wherein the sheath of the first auxiliary blade comprises an engagement mechanism at the proximal end, the engagement mechanism for attaching the first auxiliary blade to the anterior cabin.

3. The retractor of claim 1, wherein the at least two planes are orthogonal to each other.

4. The retractor of claim 1, wherein the first auxiliary blade further comprises a blade arm in connection with the proximal end of the sheath, the blade arm for connecting the first auxiliary blade to the anterior cabin.

5. The retractor of claim 4, wherein the blade arm comprises a plurality of teeth for engaging a gear mechanism of the anterior cabin.

6. The retractor of claim 4, wherein the blade arm comprises a rod for engaging a clamp of the anterior cabin.

7. The retractor of claim 1, wherein the anterior cabin comprises:
   a body defining a channel to receive a portion of the first auxiliary blade;
   a hook portion extending from the body towards a center line of the retractor, the hook portion for engaging the anterior arm;
   a latch for securing the anterior cabin to the anterior arm; and

a gear mechanism for engaging the portion of the first auxiliary blade.

8. A retractor for use in a surgical procedure, the retractor comprising:
   a base retractor comprising a rack having a first through opening along a first axis and a second through opening along a second axis parallel to the first axis, an anterior arm connectable to the rack through the first through opening and having an anterior blade, and a posterior arm connectable to the rack through the second through opening and having a posterior blade;
   a first cabin connectable to the anterior arm, the first cabin for receiving a first auxiliary blade defining a first axis; and
   a second auxiliary blade connectable to the posterior arm, the second auxiliary blade defining a second axis,
   wherein each of the first auxiliary blade and the second auxiliary blade is adjustable in length and angulation, and
   wherein the first and second axes are not parallel to each other so that each of the first auxiliary blade and the second auxiliary blade has an outward bias relative to the anterior blade and posterior blade, respectively.

9. The retractor of claim 8, wherein the anterior arm defines a slot for receiving a portion of the first cabin.

10. The retractor of claim 8, further comprising a second cabin for connecting the second auxiliary blade to the posterior arm.

11. The retractor of claim 8, wherein each of the first auxiliary blade and the second auxiliary blade comprise:
   a sheath extending from a proximal end to a distal end; and
   a blade tip in connection with the sheath, the blade tip being biased in a first position.

12. The retractor of claim 11, further comprising at least one spring for biasing the blade tip in the first position.

13. The retractor of claim 11, wherein the blade tip transitions from the first position to a second position relative to the sheath when the blade tip contacts patient anatomy during a surgical procedure.

14. The retractor of claim 11, wherein the blade tip is pressed inwardly from the outward bias when the blade tip is pressed inwardly by patient anatomy during a surgical procedure, and wherein the blade tip returns to the outward bias when not pressed inwardly by the patient anatomy.

15. A method of creating and/or maintaining an exposure in a surgical procedure, the method comprising:
   providing the retractor of claim 1;
   attaching the anterior cabin to the anterior arm of the base, the anterior arm having an anterior blade;
   attaching the posterior cabin to the posterior arm of the base, the posterior arm having a posterior blade, the posterior blade being substantially parallel to the anterior blade;
   securing the first auxiliary blade to the anterior cabin, the first auxiliary blade oriented orthogonal to the anterior blade and having an outward bias relative to the anterior blade; and
   securing the second auxiliary blade to the posterior cabin, the second auxiliary blade oriented orthogonal to the posterior blade and having an outward bias relative to the posterior blade,
   each of the first auxiliary blade and the second auxiliary blade being independently moveable relative to the anterior blade, the posterior blade, and each other.

16. The method of claim 15, wherein attaching the anterior cabin to the anterior arm of the base retractor comprises:

positioning a hook portion of the anterior cabin over the anterior arm;

depressing a latch contained within a distal portion of the anterior cabin; and releasing the latch, such that the hook portion of the anterior cabin is secured to a top surface of the anterior arm and the latch is adjacent a bottom surface of the anterior arm.

17. The method of claim 15, wherein attaching the posterior cabin to the posterior arm of the base retractor comprises:

positioning a hook portion of the posterior cabin over the posterior arm, such that an extension of the posterior cabin extends posteriorly past the posterior blade;

depressing a latch contained within a distal portion of the posterior cabin; and releasing the latch, such that the hook portion of the posterior cabin is secured to a top surface of the posterior arm and the latch is [secured to/adjacent] a bottom surface of the posterior arm.

18. The method of claim 15, wherein securing the first auxiliary blade to the anterior cabin comprises:

connecting a proximal end of the first auxiliary blade to a first blade arm; and securing the first blade arm to a portion of the anterior cabin.

19. The method of claim 18, wherein securing the first blade arm to a portion of the anterior cabin comprises clamping a portion of the first blade arm within a clamp of the anterior cabin.

20. The method of claim 15, further comprising:

retracting the first auxiliary blade into the anterior cabin; and retracting the second auxiliary blade into the posterior cabin.

21. A retractor for use in a surgical procedure, the retractor comprising:

a base retractor comprising a rack having a first through opening along a first axis and a second through opening along a second axis parallel to the first axis, an anterior arm connectable to the rack through the first through opening and having an anterior blade, and a posterior arm connectable to the rack through the second through opening and having a posterior blade;

a first cabin connectable to the anterior arm, the first cabin for receiving a first auxiliary blade defining a first axis; and a second auxiliary blade connectable to the posterior arm, the second auxiliary blade defining a second axis;

wherein each of the first auxiliary blade and the second auxiliary blade is adjustable in length and angulation;

wherein the first and second axes are not parallel to each other so that each of the first auxiliary blade and the second auxiliary blade has an outward bias relative to the anterior blade and posterior blade, respectively; and wherein the anterior arm defines a slot for receiving a portion of the first cabin.

22. The retractor of claim 21, further comprising a second cabin for connecting the second auxiliary blade to the posterior arm.

23. The retractor of claim 21, wherein each of the first auxiliary blade and the second auxiliary blade comprise:

a sheath extending from a proximal end to a distal end; and a blade tip in connection with the sheath, the blade tip being biased in a first position.

24. The retractor of claim 23, further comprising at least one spring for biasing the blade tip in the first position.

25. The retractor of claim 23, further comprising a screw-actuated adjustment mechanism configured to translate the blade tip along at least a portion of the sheath.

26. The retractor of claim 25, further comprising at least one spring for biasing the blade tip in the first position.

27. The retractor of claim 23, wherein the blade tip transitions from the first position to a second position relative to the sheath when the blade tip contacts patient anatomy during a surgical procedure.

28. The retractor of claim 23, wherein the blade tip is pressed inwardly from the outward bias when the blade tip is pressed inwardly by patient anatomy during a surgical procedure, and wherein the blade tip returns to the outward bias when not pressed inwardly by the patient anatomy.

* * * * *